US010081634B2

(12) United States Patent
Park et al.

(10) Patent No.: US 10,081,634 B2
(45) Date of Patent: Sep. 25, 2018

(54) HETEROCYCLIC COMPOUND

(71) Applicant: Daewoong Pharmaceutical Co., Ltd., Gyeonggi-do (KR)

(72) Inventors: Joon Seok Park, Gyeonggi-do (KR); Youn Jung Yoon, Gyeonggi-do (KR); Min Jae Cho, Gyeonggi-do (KR); Ho Bin Lee, Seoul (KR); Ja Kyung Yoo, Gyeonggi-do (KR); Yong Lee Bong, Seoul (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 105 days.

(21) Appl. No.: 15/312,192

(22) PCT Filed: Jun. 23, 2015

(86) PCT No.: PCT/KR2015/006377
§ 371 (c)(1),
(2) Date: Nov. 18, 2016

(87) PCT Pub. No.: WO2015/199418
PCT Pub. Date: Dec. 30, 2015

(65) Prior Publication Data
US 2017/0088551 A1 Mar. 30, 2017

(30) Foreign Application Priority Data

Jun. 23, 2014 (KR) .................. 10-2014-0076674

(51) Int. Cl.
| C07D 473/40 | (2006.01) |
| A61K 31/4427 | (2006.01) |
| C07D 235/04 | (2006.01) |
| C07D 401/12 | (2006.01) |
| C07D 401/06 | (2006.01) |
| C07D 471/04 | (2006.01) |

(52) U.S. Cl.
CPC ........ *C07D 473/40* (2013.01); *A61K 31/4427* (2013.01); *C07D 235/04* (2013.01); *C07D 401/06* (2013.01); *C07D 401/12* (2013.01); *C07D 471/04* (2013.01)

(58) Field of Classification Search
None
See application file for complete search history.

(56) References Cited

U.S. PATENT DOCUMENTS

2018/0044322 A1    2/2018    Park et al.

FOREIGN PATENT DOCUMENTS

| CA | 2977752 A1 | 12/2016 |
| WO | WO-2010/019210 A2 | 2/2010 |
| WO | WO-2010/096170 A2 | 8/2010 |
| WO | WO-2013/106702 A1 | 7/2013 |

OTHER PUBLICATIONS

Non-final official action dated Feb. 9, 2018, in U.S. Appl. No. 15/556,352.
Office Action in CA Application No. 2,951,798 dated Dec. 28, 2017, 4 pages.
Opinion of the Scientific Panel on Additives and Products or Substances Used in Animal Feed on a Request From the Commission on the re-Evaluation of Coccidiostat Stenorol in Accordance with Article 9G of Council Directive 70/524/EEC, the EFSA Journal 8, 2003, pp. 1-45.
Linder et al., "(2R,3S)-(+)- and (2S,3R)-(-)-Halofuginone Lactate: Synthesis, Absolute Configuration, and Activity Against Cryptosporidium Parvum", Bioorganic & Medicinal Chemistry Letters 17, 2007, pp. 4140-4143.
Kim et. el., "Aminoacyl-tRNA Synthetases and Tumorigenesis: More Than Housekeeping", Nature Reviews Cancer, vol. 11, Oct. 2011, pp. 708-718.
Cui et al., "Efficient One-Pot Synthesis of 2-substituted Benzimidazoles From Triacyloxyborane Intermediates", Synlett, vol. 23, 2012, pp. 247-250.
Zhou et al., "Proteomic Analysis Reveals Warburg Effect and Anomalous Metabolism of Glutamine in Pancreatic Cancer Cells", J. Proteome Res., vol. 11, 2012, pp. 554-563.
Keller et al., "Halofuginone and Other Febrifugine Derivatives Inhibit Prolyl-tRNA Synthetase", Nature Chemical Biology, vol. 8, No. 3, Mar. 2012, pp. 311-317.
Yao et al., "Coding Region Polyadenylation Generates a Truncated rRNA Snythetase That Counters Translation Repression", Cell 149, Mar. 30, 2012, pp. 88-100.
Zhou et al., "ATP-directed Capture of Bioactive Herbal-Based Medicine on Human tRNA Synthetase", Nature, vol. 494, No. 7435, Feb. 7, 2013, pp. 121-125.
Roy et al., "One-Pot Sequential Syntheses of 1, 2-disubstituted Benzimidazoles Under Metal-Free Conditions", Tetrahedron Letters, vol. 54, No. 38, 2013, pp. 5243-5245.
McLaughlin et al., "The Chemistry and Biology of Febrifugine and halofuginone", Bioorganic & Medicinal Chemistry, vol. 22, 2014, pp. 1993-2004.
Carlson et al., "Halofuginone-induced Amino Acid Starvation Regulates Stat3-dependent Th17 Effector Function and Reduces Established Autoimmune Inflammation", J. Immunol. vol. 192(5), Mar. 1, 2014, pp. 2167-2176.
Park et al., "Halofuginone Ameliorates Autoimmune Arthritis in Mice by Regulating the Balance Between Th17 and Treg Cells and Inhibiting Osteoclastogenesis", Arthritis & Rheumatology, vol. 66, No. 5, May 2014, pp. 1195-1207.
Mark Pines, "Halofuginone for Fibrosis, Regeneration and Cancer in the Gastrointestinal Tract", World Journal of Gastroenterology, vol. 20, Issue 40, Oct. 28, 2014, pp. 14778-14786.
(Continued)

*Primary Examiner* — Nyeemah A Grazier
(74) *Attorney, Agent, or Firm* — Marshall, Gerstein & Borun LLP

(57) ABSTRACT

The present invention relates to a compound represented by chemical formula 1, which can be used for the prevention and treatment of diseases caused by abnormality in a prolyl-tRNA synthetase (PRS) activity, or a pharmaceutically acceptable salt thereof, a method for preparing the same, and a pharmaceutical composition comprising the same.

17 Claims, 2 Drawing Sheets
(2 of 2 Drawing Sheet(s) Filed in Color)

(56) References Cited

OTHER PUBLICATIONS

Jain et al., "Structure of Prolyl-tRNA Synthetase-halofuginone Complex Provides Basis for Development of Drugs Against Malaria and Toxoplasmosis", Structure, vol. 23, No. 5, May 5, 2015, pp. 819-829.

Search Report and Written Opinion in International Application No. PCT/KR2015/006377 dated Feb. 29, 2016, 19 pages (English translation of search report).

[Fig. 1]
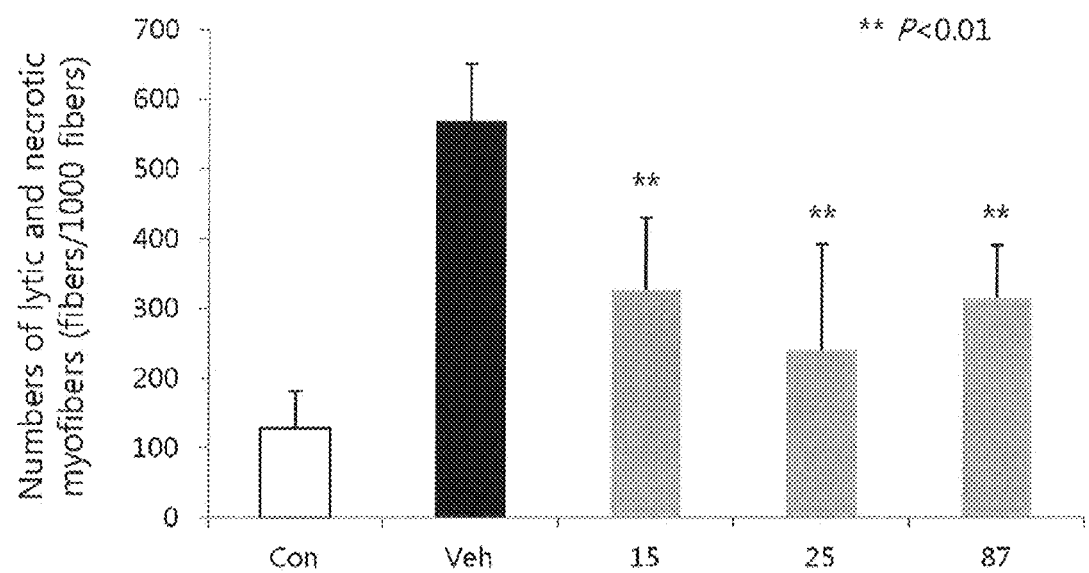
[Fig. 2]
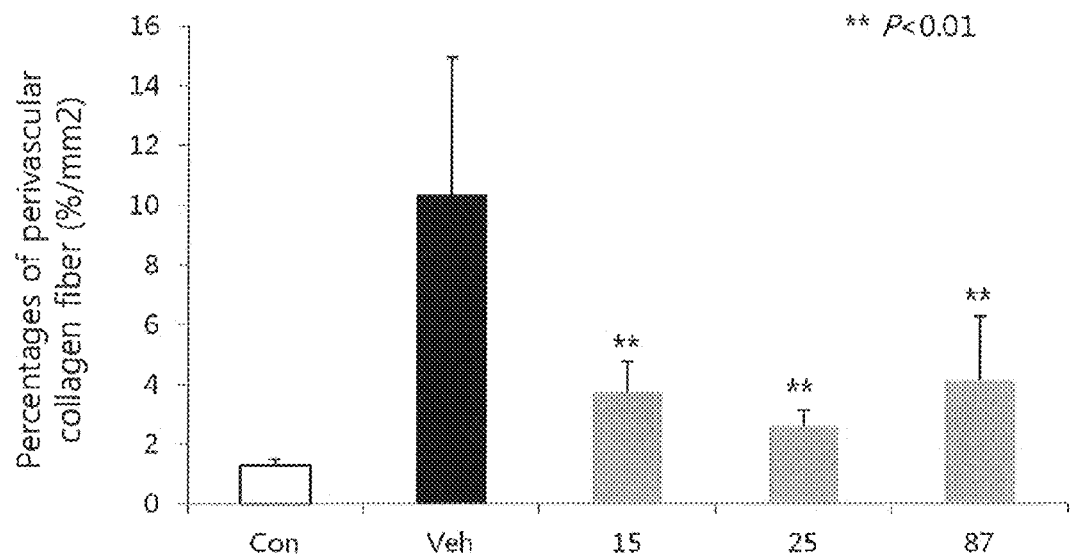

[Fig. 3]
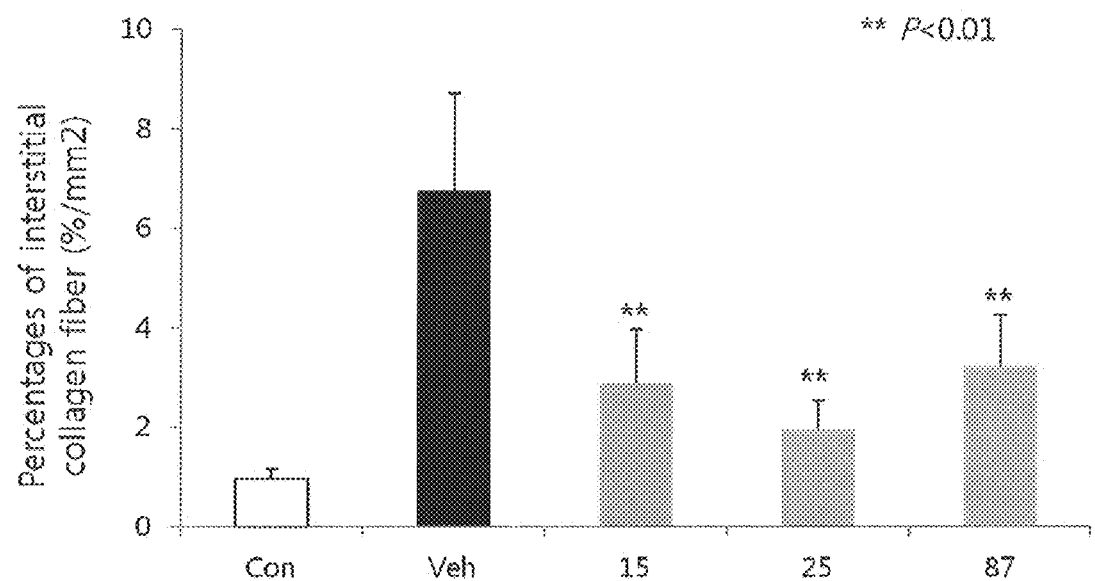
[Fig. 4]
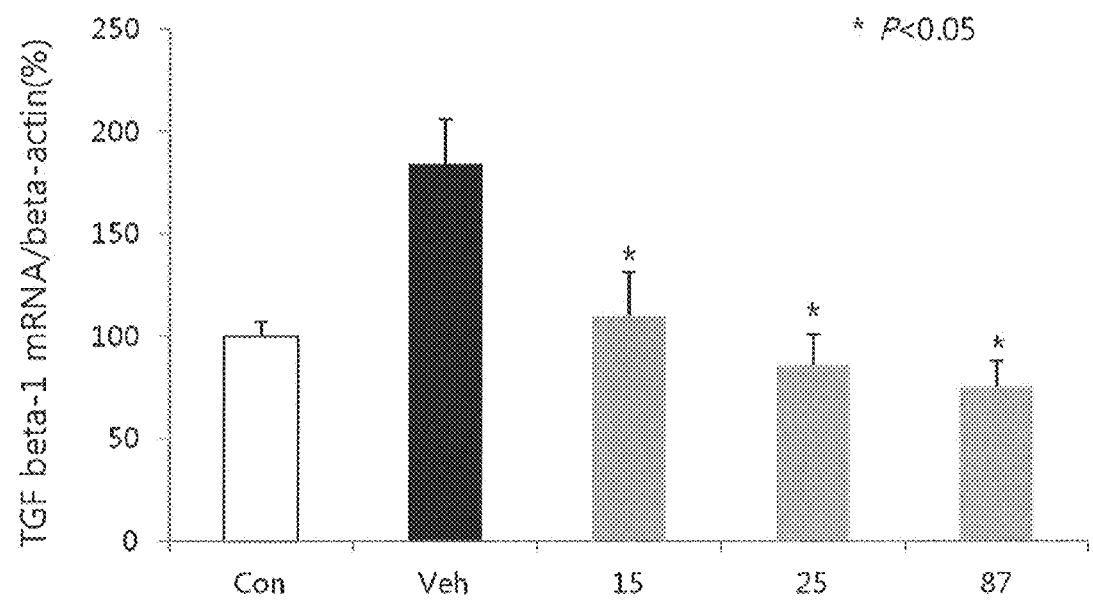

HETEROCYCLIC COMPOUND

TECHNICAL FIELD

The present invention relates to a heterocyclic compound that can be effectively used in the prevention or treatment of a cancer, an inflammatory disease, an autoimmune disease or a fibrosis, a method for preparing the same, and a pharmaceutical composition comprising the same.

BACKGROUND OF ART

PRS (prolyl-tRNA synthetase) is an enzyme group of aminoacyl-tRNA synthetase (ARS) family and serves to activate an amino acid for protein synthesis. That is, ARS performs a translational function to form an aminoacyl adenylate (AA-AMP) and then transfer the activated amino acid to the 3-end of the corresponding tRNA. Since ARS plays an important role in the synthesis of protein, ARS inhibitors suppress the growth of all cells. Thus, ARS has been recognized as a promising target for a therapeutic agent for treating diseases that should suppress antibiotics or cell overexpression (Nature, 2013, 494:121-125).

PRS is present in, or functions as, a multisynthetase complex (MSC) in the form of EPRS (Glutamyl-Prolyl-tRNA Synthetase). In particular, among various MSCs, EPRS has been reported to be closely associated with various solid tumors (see, Nat. Rev. Cancer, 2011, 11, 708-718). In recent years, it has been reported that EPRS is overexpressed in PANC-1 cells which are pancreatic cancer cells (J. Proteome Res, 2012, 11: 554-563).

It has been known that EPRS is separated from MSC through the stimulation of interferon-gamma to form GAIT (Gamma-Interferon Activated Inhibitor of Translation) complex, thereby suppressing the synthesis of different inflammatory protein including Cp (ceruloplasmin) (Cell, 2012, 149: 88-100).

The only substance, known as the PRS inhibitor, is halofuginone. Halofuginone is a derivative of febrifugine derived from natural products and have anti-malarial effects and various anti-inflammatory effects. It can also be used as an animal feed additive. Currently, halofuginone is being clinically studied as anti-cancer agent, an anti-inflammatory agent (J Immunol, 2014, 192(5), 2167-76), therapeutic agents for the treatment of autoimmune diseases (Arthritis Rheumatol, 2014, 66 (5), 1195-207), and therapeutic agents for the treatment of fibrotic diseases (World J Gastroenterol, 2014, 20 (40), 14778-14786) (Bioorg. Med. Chem. 2014, 22, 1993-2004).

However, it has been reported that halofuginone acts on various targets and has a very severe toxicity (Bioorg. Med. Chem. Lett., 2007, 17: 4140-4143), and further there is a risk of genotoxicity (The EFSA Journal, 2003, 8: 1-45). Therefore, discovering PRS inhibitors having higher safety to the human body among substances capable of inhibiting PRS like halofuginone has a significance in terms of developing an anti-cancer agent of the next generation that can be used as an antifibrosis agent, an anti-inflammatory agent, an autoimmune therapeutic agent alone or in combination with an existing targeted anti-cancer agent.

In this regard, the present inventors have conducted numerous studies to develop a novel small molecule compound with reduced toxicity while having a PRS enzyme inhibitory effect, and found that the compound having a novel structure which will be described later selectively inhibits the PRS, thereby completing the present invention.

DETAILED DESCRIPTION OF THE INVENTION

Technical Problem

The present invention provides a novel heterocyclic compound that can be effectively used in the prevention or treatment of a cancer, an inflammatory disease, an autoimmune disease or a fibrosis, a method for preparing the same, and a pharmaceutical composition comprising the same.

Technical Solution

In order to achieve the above objects, the present invention provides a compound represented by the following Chemical Formula 1, or a pharmaceutically acceptable salt thereof:

[Chemical Formula 1]

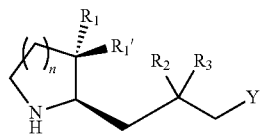

in Chemical Formula 1,
n is 1, or 2,
$R_1$ is hydrogen, or hydroxy,
$R_1'$ is hydrogen,
$R_2$ is hydroxy, halogen, amino, $C_{1-4}$ alkylamino, di($C_{1-4}$ alkyl)amino, or $C_{1-4}$ alkoxy; $R_3$ is hydrogen, halogen, $C_{1-4}$ alkyl, or $C_{1-4}$ haloalkyl; or $R_2$ and $R_3$ together form an oxo (=O), hydroxyimino (=N—OH), or $C_{1-4}$ alkoxyimino (=N—O—($C_{1-4}$ alkyl));
Y is

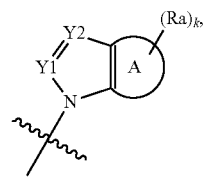

Y1 is N, CH, or $CR_4$,
wherein $R_4$ is $C_{1-4}$ alkyl, $C_{1-4}$ hydroxyalkyl, $C_{1-4}$ alkyl substituted with $C_{1-4}$ alkoxy, $C_{1-4}$ haloalkyl, or —($CH_2$)$_m$ $NR_9R_{10}$, wherein m is an integer of 1 to 4, and $R_9$ and $R_{10}$ are each independently hydrogen, or $C_{1-4}$ alkyl,
Y2 is N, or CH,
A is benzene, heteroaryl having 1 to 4 nitrogen atoms, or cyclohexene, as a six-membered ring,
k is an integer of 0 to 4, and
each of Ra is independently $C_{1-4}$ alkyl, $C_{1-4}$ alkoxy, $C_{1-4}$ haloalkyl, $C_{1-4}$ haloalkoxy, halogen, cyano, or carboxy.

Preferably, $R_2$ is hydroxy, fluoro, amino, methylamino, dimethylamino, or methoxy; $R_3$ is hydrogen, fluoro, methyl, or trifluoromethyl; or $R_2$ and $R_3$ together form oxo (=O), hydroxyimino (=N—OH), or methoxyimino (=N—$OCH_3$).

Also preferably, A is benzene, pyridine, pyrimidine, or cyclohexene.

Also preferably, $R_4$ is methyl, ethyl, hydroxymethyl, hydroxyethyl, 1-hydroxyethyl, trifluoromethyl, methoxymethyl, aminomethyl, or (dimethylamino)methyl.

Also preferably, Y is

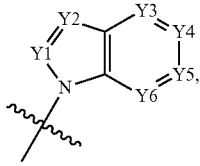

Y3 is N, or C—$R_5$; Y4 is N, or C—$R_6$; Y5 is N, or C—$R_7$; Y6 is N, or C—$R_8$, $R_5$ is hydrogen, $C_{1-4}$ alkyl, $C_{1-4}$ haloalkyl, or halogen; $R_6$ is hydrogen, $C_{1-4}$ alkyl, $C_{1-4}$ alkoxy, $C_{1-4}$ haloalkyl, $C_{1-4}$ haloalkoxy, halogen, cyano, or carboxy; $R_7$ is hydrogen, $C_{1-4}$ alkyl, $C_{1-4}$ alkoxy, $C_{1-4}$ haloalkyl, $C_{1-4}$ haloalkoxy, halogen, or cyano; $R_8$ is hydrogen, $C_{1-4}$ alkyl, $C_{1-4}$ haloalkyl, $C_{1-4}$ haloalkoxy, or halogen. More preferably, $R_5$ is hydrogen, methyl, trifluoromethyl, fluoro, chloro, or bromo; $R_6$ is hydrogen, methyl, trifluoromethyl, trifluoromethoxy, fluoro, chloro, bromo, cyano, or carboxy; $R_7$ is hydrogen, methyl, trifluoromethyl, fluoro, chloro, or bromo; and $R_8$ is hydrogen, methyl, trifluoromethyl, trifluoromethoxy, chloro, or bromo.

Also preferably, Y is

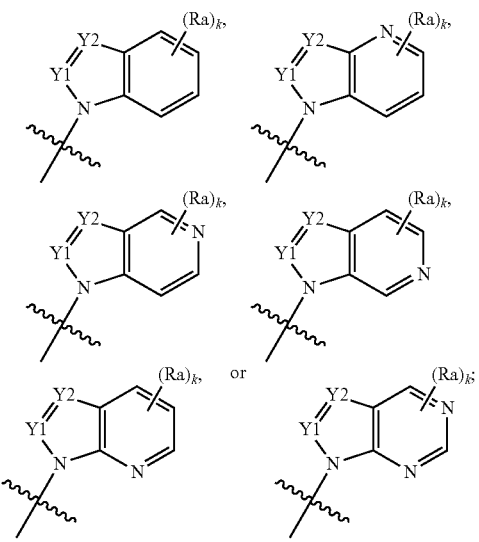

k is an integer of 0 to 2. More preferably, each of Ra is independently $C_{1-4}$ alkyl, $C_{1-4}$ haloalkyl, $C_{1-4}$ haloalkoxy, halogen, cyano, or carboxy. Most preferably, each of Ra is independently methyl, trifluoromethyl, trifluoromethoxy, fluoro, chloro, bromo, cyano, or carboxy.

Also preferably, in Chemical Formula 1,
n is an integer of 1 or 2,
$R_1$ is hydrogen, or hydroxy,
$R_1'$ is hydrogen,
$R_2$ is hydroxy, halogen, $C_{1-4}$ alkylamino, or $C_{1-4}$ alkoxy; $R_3$ is hydrogen, halogen, $C_{1-4}$ alkyl, or $C_{1-4}$ haloalkyl; or $R_2$ and $R_3$ together form an oxo (=O), hydroxyimino (=N—OH), or $C_{1-4}$ alkoxyimino (=N—O—($C_{1-4}$ alkyl));

Y is

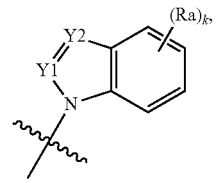

Y1 is CH, or $CR_4$,
wherein $R_4$ is $C_{1-4}$ alkyl, $C_{1-4}$ hydroxyalkyl, $C_{1-4}$ alkyl substituted with $C_{1-4}$ alkoxy, $C_{1-4}$ haloalkyl, $C_{1-4}$ alkyl substituted with amino, or $C_{1-4}$ alkyl substituted with di($C_{1-4}$ alkyl)amino,
Y2 is N,
k is an integer of 0 to 2,
each of Ra is independently $C_{1-4}$ alkyl, $C_{1-4}$ haloalkyl, $C_{1-4}$ haloalkoxy, or halogen.

In addition, preferably, in Chemical Formula 1,
n is 2,
$R_1$ is hydroxy,
$R_1'$ is hydrogen,
$R_2$ is hydroxy; $R_3$ is hydrogen; or $R_2$ and $R_3$ together form an oxo (=O);
Y is

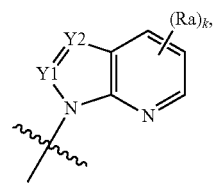

Y1 is CH,
Y2 is N,
k is an integer of 0 to 2,
each of Ra is independently $C_{1-4}$ alkyl, $C_{1-4}$ haloalkyl, halogen, or cyano.

Typical examples of the compounds represented by Chemical Formula 1 or a pharmaceutically acceptable salt thereof are as follows:

1) 1-(1H-benzo[d]imidazol-1-yl)-3-((2R,3S)-3-hydroxypiperidin-2-yl)propan-2-one,
2) 1-(5-chloro-1H-benzo[d]imidazol-1-yl)-3-((2R,3S)-3-hydroxypiperidin-2-yl)propan-2-one,
3) 1-(6-chloro-1H-benzo[d]imidazol-1-yl)-3-((2R,3S)-3-hydroxypiperidin-2-yl)propan-2-one,
4) 1-(5-bromo-1H-benzo[d]imidazol-1-yl)-3-((2R,3S)-3-hydroxypiperidin-2-yl)propan-2-one,
5) 1-(6-bromo-1H-benzo[d]imidazol-1-yl)-3-((2R,3S)-3-hydroxypiperidin-2-yl)propan-2-one,
6) 1-((2R,3S)-3-hydroxypiperidin-2-yl)-3-(5-(trifluoromethyl)-1H-benzo[d]imidazol-1-yl)propan-2-one,
7) 1-((2R,3S)-3-hydroxypiperidin-2-yl)-3-(6-(trifluoromethyl)-1H-benzo[d]imidazol-1-yl)propan-2-one,
8) 1-((2R,3S)-3-hydroxypiperidin-2-yl)-3-(7-(trifluoromethyl)-1H-benzo[d]imidazol-1-yl)propan-2-one,
9) 1-(5,6-dimethyl-1H-benzo[d]imidazol-1-yl)-3-((2R,3S)-3-hydroxypiperidin-2-yl)propan-2-one,
10) 1-(5,6-difluoro-1H-benzo[d]imidazol-1-yl)-3-((2R,3S)-3-hydroxypiperidin-2-yl)propan-2-one, 11) 1-(4,5-difluoro-1H-benzo[d]imidazol-1-yl)-3-((2R,3S)-3-hydroxypiperidin-2-yl)propan-2-one,
12) 1-(4,5-dichloro-1H-benzo[d]imidazol-1-yl)-3-((2R,3S)-3-hydroxypiperidin-2-yl)propan-2-one,
13) 1-(5-fluoro-4-methyl-1H-benzo[d]imidazol-1-yl)-3-((2R,3S)-3-hydroxypiperidin-2-yl)propan-2-one,
14) 1-(5-chloro-4-methyl-1H-benzo[d]imidazol-1-yl)-3-((2R,3S)-3-hydroxypiperidin-2-yl)propan-2-one,
15) 1-(5-bromo-4-methyl-1H-benzo[d]imidazol-1-yl)-3-((2R,3S)-3-hydroxypiperidin-2-yl)propan-2-one,
16) 1-(4,5-dimethyl-1H-benzo[d]imidazol-1-yl)-3-((2R,3S)-3-hydroxypiperidin-2-yl)propan-2-one,
17) 1-(5-fluoro-4-(trifluoromethyl)-1H-benzo[d]imidazol-1-yl)-3-((2R,3S)-3-hydroxypiperidin-2-yl)propan-2-one,
18) 1-(5-bromo-4-(trifluoromethyl)-1H-benzo[d]imidazol-1-yl)-3-((2R,3S)-3-hydroxypiperidin-2-yl)propan-2-one,
19) 1-(4-bromo-5-methyl-1H-benzo[d]imidazol-1-yl)-3-((2R,3S)-3-hydroxypiperidin-2-yl)propan-2-one,
20) 1-(5-bromo-4-fluoro-1H-benzo[d]imidazol-1-yl)-3-((2R,3S)-3-hydroxypiperidin-2-yl)propan-2-one,
21) 1-(4-chloro-5-fluoro-1H-benzo[d]imidazol-1-yl)-3-((2R,3S)-3-hydroxypiperidin-2-yl)propan-2-one,
22) 1-(5-bromo-4-chloro-1H-benzo[d]imidazol-1-yl)-3-((2R,3S)-3-hydroxypiperidin-2-yl)propan-2-one,
23) 1-(6-bromo-4-methyl-1H-benzo[d]imidazol-1-yl)-3-((2R,3S)-3-hydroxypiperidin-2-yl)propan-2-one,
24) 1-(6-chloro-4-methyl-1H-benzo[d]imidazol-1-yl)-3-((2R,3S)-3-hydroxypiperidin-2-yl)propan-2-one,
25) 1-(5,6-dichloro-1H-benzo[d]imidazol-1-yl)-3-((2R,3S)-3-hydroxypiperidin-2-yl)propan-2-one,
26) 1-(6-bromo-5-fluoro-1H-benzo[d]imidazol-1-yl)-3-((2R,3S)-3-hydroxypiperidin-2-yl)propan-2-one,
27) 1-(5,6-dibromo-1H-benzo[d]imidazol-1-yl)-3-((2R,3S)-3-hydroxypiperidin-2-yl)propan-2-one,
28) 1-(6-chloro-7-methyl-1H-benzo[d]imidazol-1-yl)-3-((2R,3S)-3-hydroxypiperidin-2-yl)propan-2-one,
29) 1-(5-bromo-1H-imidazo[4,5-b]pyridin-1-yl)-3-((2R,3S)-3-hydroxypiperidin-2-yl)propan-2-one,
30) 1-((2R,3S)-3-hydroxypiperidin-2-yl)-3-(5-(trifluoromethyl)-1H-imidazo[4,5-b]pyridin-1-yl)propan-2-one,
31) 1-(6-bromo-1H-imidazo[4,5-b]pyridin-1-yl)-3-((2R,3S)-3-hydroxypiperidin-2-yl)propan-2-one,
32) 1-(6-chloro-1H-imidazo[4,5-c]pyridin-1-yl)-3-((2R,3S)-3-hydroxypiperidin-2-yl)propan-2-one,
33) 1-(7-bromo-1H-imidazo[4,5-c]pyridin-1-yl)-3-((2R,3S)-3-hydroxypiperidin-2-yl)propan-2-one,
34) 1-((2R,3S)-3-hydroxypiperidin-2-yl)-3-(3H-imidazo[4,5-b]pyridin-3-yl)propan-2-one,
35) 1-(5-bromo-3H-imidazo[4,5-b]pyridin-3-yl)-3-((2R,3S)-3-hydroxypiperidin-2-yl)propan-2-one,
36) 1-((2R,3S)-3-hydroxypiperidin-2-yl)-3-(5-(trifluoromethyl)-3H-imidazo[4,5-b]pyridin-3-yl)propan-2-one,
37) 1-(6-bromo-3H-imidazo[4,5-b]pyridin-3-yl)-3-((2R,3S)-3-hydroxypiperidin-2-yl)propan-2-one,
38) 3-(3-((2R,3S)-3-hydroxypiperidin-2-yl)-2-oxopropyl)-3H-imidazo[4,5-b]pyridine-6-carbonitrile,
39) 1-(6-chloro-7-methyl-3H-imidazo[4,5-b]pyridin-3-yl)-3-((2R,3S)-3-hydroxypiperidin-2-yl)propan-2-one,
40) 1-(6-bromo-7-methyl-3H-imidazo[4,5-b]pyridin-3-yl)-3-((2R,3S)-3-hydroxypiperidin-2-yl)propan-2-one,
41) 1-(5,7-dichloro-3H-imidazo[4,5-b]pyridin-3-yl)-3-((2R,3S)-3-hydroxypiperidin-2-yl)propan-2-one,
42) 1-(6-bromo-7-chloro-3H-imidazo[4,5-b]pyridin-3-yl)-3-((2R,3S)-3-hydroxypiperidin-2-yl)propan-2-one,
43) 3-(3-((2R,3S)-3-hydroxypiperidin-2-yl)-2-oxopropyl)-3H-imidazo[4,5-c]pyridine-6-carboxylic acid hydrochloride salt,
44) 1-(6-chloro-9H-purin-9-yl)-3-((2R,3S)-3-hydroxypiperidin-2-yl)propan-2-one hydrochloride salt,
45) 1-((2R,3S)-3-hydroxypiperidin-2-yl)-3-(4,5,6,7-tetrahydro-1H-benzo[d]imidazol-1-yl)propan-2-one,
46) 1-(5,6-dichloro-2-methyl-1H-benzo[d]imidazol-1-yl)-3-((2R,3S)-3-hydroxypiperidin-2-yl)propan-2-one,
47) 1-(4,5-difluoro-2-methyl-1H-benzo[d]imidazol-1-yl)-3-((2R,3S)-3-hydroxypiperidin-2-yl)propan-2-one,
48) 1-(5,6-dichloro-2-ethyl-1H-benzo[d]imidazol-1-yl)-3-((2R,3S)-3-hydroxypiperidin-2-yl)propan-2-one,
49) 1-((2R,3S)-3-hydroxypiperidin-2-yl)-3-(2-methyl-1H-imidazo[4,5-b]pyridin-1-yl)propan-2-one,
50) 1-(5,6-dichloro-2-(trifluoromethyl)-1H-benzo[d]imidazol-1-yl)-3-((2R,3S)-3-hydroxypiperidin-2-yl)propan-2-one,
51) 1-(5,6-dichloro-2-((dimethylamino)methyl)-1H-benzo[d]imidazol-1-yl)-3-((2R,3S)-3-hydroxypiperidin-2-yl)propan-2-one,
52) 1-(2-(aminomethyl)-5,6-dichloro-1H-benzo[d]imidazol-1-yl)-3-((2R,3S)-3-hydroxypiperidin-2-yl)propan-2-one,
53) 1-(6-fluoro-2-(2-hydroxyethyl)-1H-benzo[d]imidazol-1-yl)-3-((2R,3S)-3-hydroxypiperidin-2-yl)propan-2-one,
54) 1-(2-((R)-1-hydroxyethyl)-1H-benzo[d]imidazol-1-yl)-3-((2R,3S)-3-hydroxypiperidin-2-yl)propan-2-one,
55) 1-(2-((S)-1-hydroxyethyl)-1H-benzo[d]imidazol-1-yl)-3-((2R,3S)-3-hydroxypiperidin-2-yl)propan-2-one,
56) 1-(2-(hydroxymethyl)-1H-benzo[d]imidazol-1-yl)-3-((2R,3S)-3-hydroxypiperidin-2-yl)propan-2-one,
57) 1-(5-bromo-2-(hydroxymethyl)-1H-benzo[d]imidazol-1-yl)-3-((2R,3S)-3-hydroxypiperidin-2-yl)propan-2-one,
58) 1-(6-bromo-2-(hydroxymethyl)-1H-benzo[d]imidazol-1-yl)-3-((2R,3S)-3-hydroxypiperidin-2-yl)propan-2-one,
59) 1-(2-(hydroxymethyl)-6-(trifluoromethyl)-1H-benzo[d]imidazol-1-yl)-3-((2R,3S)-3-hydroxypiperidin-2-yl)propan-2-one,
60) 1-(2-(hydroxymethyl)-5-(trifluoromethoxy)-1H-benzo[d]imidazol-1-yl)-3-((2R,3S)-3-hydroxypiperidin-2-yl)propan-2-one,
61) 1-(2-(hydroxymethyl)-7-(trifluoromethoxy)-1H-benzo[d]imidazol-1-yl)-3-((2R,3S)-3-hydroxypiperidin-2-yl)propan-2-one,
62) 1-(2-(hydroxymethyl)-4,5-dimethyl-1H-benzo[d]imidazol-1-yl)-3-((2R,3S)-3-hydroxypiperidin-2-yl)propan-2-one,
63) 1-(5,6-dichloro-2-(methoxymethyl)-1H-benzo[d]imidazol-1-yl)-3-((2R,3S)-3-hydroxypiperidin-2-yl)propan-2-one,
64) 1-(5,6-dichloro-1H-benzo[d]imidazol-1-yl)-3-((2R,3S)-3-hydroxypiperidin-2-yl)propan-2-one oxime,
65) 1-(5,6-dichloro-2-(hydroxymethyl)-1H-benzo[d]imidazol-1-yl)-3-((2R,3S)-3-hydroxypiperidin-2-yl)propan-2-one oxime,
66) 1-(6-bromo-1H-imidazo[4,5-b]pyridin-1-yl)-3-((2R,3S)-3-hydroxypiperidin-2-yl)propan-2-one oxime,
67) 1-(5,6-dichloro-1H-benzo[d]imidazol-1-yl)-3-((2R,3S)-3-hydroxypiperidin-2-yl)propan-2-one O-methyl oxime,
68) 1-(2-(hydroxymethyl)-1H-imidazo[4,5-b]pyridin-1-yl)-3-((2R,3S)-3-hydroxypiperidin-2-yl)propan-2-one,
69) (2R,3S)-2-(3-(1H-benzo[d]imidazol-1-yl)-2-hydroxypropyl)piperidin-3-ol,
70) (2R,3S)-2-(3-(5,6-dichloro-1H-benzo[d]imidazol-1-yl)-2-hydroxypropyl)piperidin-3-ol,
71) (2R,3S)-2-(3-(5-bromo-4-chloro-1H-benzo[d]imidazol-1-yl)-2-hydroxypropyl)piperidin-3-ol,
72) (2R,3S)-2-(3-(5-bromo-4-(trifluoromethyl)-1H-benzo[d]imidazol-1-yl)-2-hydroxypropyl)piperidin-3-ol, 73) (2R,3S)-2-(3-(4-bromo-5-methyl-1H-benzo[d]imidazol-1-yl)-2-hydroxypropyl)piperidin-3-ol,
74) (2R,3S)-2-(3-(5-bromo-4-fluoro-1H-benzo[d]imidazol-1-yl)-2-hydroxypropyl)piperidin-3-ol,
75) (2R,3S)-2-(3-(4,5-dichloro-1H-benzo[d]imidazol-1-yl)-2-hydroxypropyl)piperidin-3-ol,
76) (2R,3S)-2-(3-(5-chloro-4-methyl-1H-benzo[d]imidazol-1-yl)-2-hydroxypropyl)piperidin-3-ol,
77) (2R,3S)-2-(3-(6-chloro-7-methyl-3H-imidazo[4,5-b]pyridin-3-yl)-2-hydroxypropyl)piperidin-3-ol,
78) (2R,3S)-2-(3-(6-bromo-7-methyl-3H-imidazo[4,5-b]pyridin-3-yl)-2-hydroxypropyl)piperidin-3-ol,
79) (2R,3S)-2-(3-(6-bromo-7-chloro-3H-imidazo[4,5-b]pyridin-3-yl)-2-hydroxypropyl)piperidin-3-ol,
80) (2R,3S)-2-(3-(1H-benzo[d]imidazol-1-yl)-2-hydroxy-2-methylpropyl)piperidin-3-ol,
81) (2R,3S)-2-(3-(5,6-dichloro-1H-benzo[d]imidazol-1-yl)-2-fluoropropyl)piperidin-3-ol,
82) (2R,3S)-2-(3-(5,6-dichloro-1H-benzo[d]imidazol-1-yl)-2,2-difluoropropyl)piperidin-3-ol,
83) (2R,3S)-2-(3-(5,6-dichloro-1H-benzo[d]imidazol-1-yl)-2-methoxypropyl)piperidin-3-ol,
84) (2R,3S)-2-(3-(5,6-dichloro-1H-benzo[d]imidazol-1-yl)-2-hydroxy-2-methylpropyl)piperidin-3-ol,
85) (2R,3S)-2-(2-((5-bromo-4-methyl-1H-benzo[d]imidazol-1-yl)methyl)-3,3,3-trifluoro-2-hydroxypropyl)piperidin-3-ol,
86) (2R,3S)-2-(3-(5,6-dichloro-1H-benzo[d]imidazol-1-yl)-2-(methylamino)propyl)piperidin-3-ol,
87) 1-(5,6-dichloro-2-(hydroxymethyl)-1H-benzo[d]imidazol-1-yl)-3-((2R,3S)-3-hydroxypiperidin-2-yl)propan-2-one,
88) (2R,3S)-2-(3-(5,6-dichloro-2-(hydroxymethyl)-1H-benzo[d]imidazol-1-yl)-2-hydroxypropyl)piperidin-3-ol,
89) (2R,3S)-2-(3-(5-bromo-4-methyl-1H-benzo[d]imidazol-1-yl)-2-hydroxypropyl)piperidin-3-ol,
90) (S)-1-(5,6-dichloro-1H-benzo[d]imidazol-1-yl)-3-(pyrrolidin-2-yl)propan-2-one,
91) 1-(5-chloro-1H-pyrrolo[2,3-b]pyridin-1-yl)-3-((2R,3S)-3-hydroxypiperidin-2-yl)propan-2-one,
92) 1-(6-bromo-1H-pyrrolo[2,3-b]pyridin-1-yl)-3-((2R,3S)-3-hydroxypiperidin-2-yl)propan-2-one,
93) 1-(7-chloro-1H-pyrrolo[2,3-c]pyridin-1-yl)-3-((2R,3S)-3-hydroxypiperidin-2-yl)propan-2-one,
94) 1-(6-bromo-1H-pyrrolo[3,2-b]pyridin-1-yl)-3-((2R,3S)-3-hydroxypiperidin-2-yl)propan-2-one,
95) 1-(3-((2R,3S)-3-hydroxypiperidin-2-yl)-2-oxopropyl)-4-methyl-1H-pyrrolo[2,3-b]pyridine-5-carbonitrile,
96) 1-(5-chloro-1H-indazol-1-yl)-3-((2R,3S)-3-hydroxypiperidin-2-yl)propan-2-one,
97) 1-(4-bromo-5-methyl-1H-indazol-1-yl)-3-((2R,3S)-3-hydroxypiperidin-2-yl)propan-2-one,
98) 1-(5-chloro-1H-pyrazolo[3,4-b]pyridin-1-yl)-3-((2R,3S)-3-hydroxypiperidin-2-yl)propan-2-one,
99) 1-(5-chloro-1H-benzo[d][1,2,3]triazol-1-yl)-3-((2R,3S)-3-hydroxypiperidin-2-yl)propan-2-one, and
100) 1-(6-chloro-1H-benzo[d][1,2,3]triazol-1-yl)-3-((2R,3S)-3-hydroxypiperidin-2-yl)propan-2-one.

The compound according to the present invention may be present in the form of a salt, particularly a pharmaceutically acceptable salt. As the salt, a salt commonly used in the art, such as an acid addition salt formed with a pharmaceutically acceptable free acid, can be used, without limitation. The term "pharmaceutically acceptable salt" as used herein refers to any organic or inorganic addition salt of the compound of Chemical Formula 1 whose concentration exhibits relatively non-toxic and harmless effective actions to a patient, and whose side effects do not decrease the beneficial efficacy of the above compound.

The acid addition salt may be prepared using a conventional method, for example, by dissolving the compound in an excess of aqueous solution of the acid followed by the precipitation of the resultant salt using a water-miscible organic solvent, such as methanol, ethanol, acetone or acetonitrile. The compound of same molar amount of a compound and an acid or alcohol in water (e.g., glycol monomethyl ether) can be heated and subsequently, the resultant mixture can be dried by evaporation, or precipitated salts can be filtered by suction.

As the free acid, an inorganic acid and an organic acid may be used. Examples of the inorganic acid may include hydrochloric acid, phosphoric acid, sulfuric acid, nitric acid, tartaric acid, and the like. Examples of the organic acid may include methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycollic acid, gluconic acid, galacturonic acid, glutamic acid, glutaric acid, glucuronic acid, aspartic acid, ascorbic acid, carbonic acid, vanillic acid, hydroiodic acid and the like, but are not limited thereto.

The pharmaceutically acceptable salts of the compounds of the present invention include salts of acidic or basic groups which may be present in the compounds of Chemical Formula 1, unless otherwise indicated.

The salts of the heterocyclic compounds of the present invention, which are pharmaceutically acceptable salts, can be used without limitation if they are the salts of heterocyclic compounds that exhibit PRS enzyme inhibitory activities equivalent to the heterocyclic compounds.

The compounds represented by Chemical Formula 1 according to the present invention includes pharmaceutically acceptable salts thereof as well as all possible hydrates, solvates and all possible stereoisomers, which can be prepared therefrom, but are not limited thereto. The solvates and stereoisomers of the compounds represented by Chemical Formula 1 can be prepared from the compounds represented by Chemical Formula 1 using methods known in the art.

Also, the compound represented by Chemical Formula 1 according to the present invention can be prepared in crystalline form or non-crystalline form. When the compound is produced in crystalline form, it may be optionally hydrated or solvated. The present invention may include not only stoichiometric hydrates of the compounds represented by Chemical Formula 1 but also compounds containing a various amount of water. The solvates of the compounds represented by Chemical Formula 1 according to the present invention include both stoichiometric solvates and non-stoichiometric solvates.

The present invention also provides a method for preparing a compound represented by Chemical Formula 1. As an example, it provides a method for preparing a compound represented by Chemical Formula 1 as shown in the following Reaction Scheme 1:

[Reaction Scheme 1]

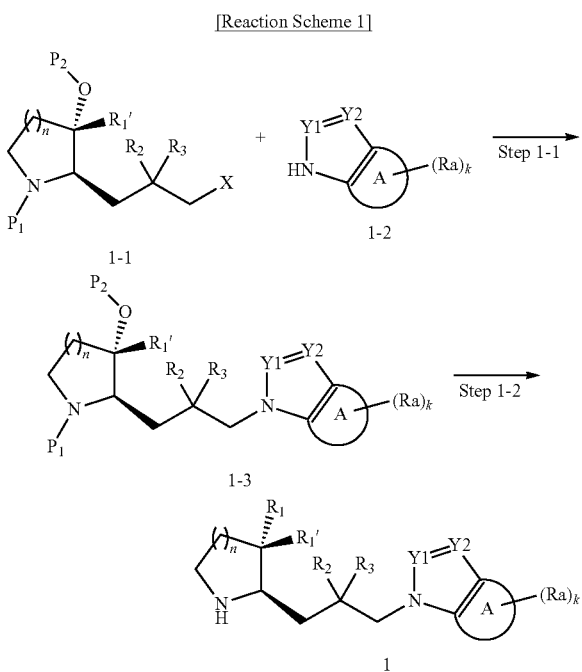

In Reaction Scheme 1, $R_1$, $R_1'$, $R_2$, $R_3$, Y1, Y2, A, Ra and k are as previously defined, $P_1$ and $P_2$ mean each independently a protecting group. However, when $R_1$ is hydrogen, hydrogen is substituted instead of O—$P_2$.

Preferably, $P_1$ is any one protecting group selected from the group consisting of carbobenzyloxy (Cbz), para-methoxybenzyl carbonyl (Moz), tert-butyloxycarbonyl (Boc), 9-fluorenyl methyloxy carbonyl (Fmoc), acetyl (Ac), benzoyl (Bz), benzyl (Bn) and para-methoxybenzyl (PMB). Preferably, $P_2$ is any one protecting group selected from the group consisting of acetyl, benzoyl, benzyl, beta-methoxyethoxy methyl ether (MEM), methoxymethyl ether (MOM), para-methoxybenzyl ether (PMB), methylthiomethyl ether, pivaloyl (Piv), tetrahydropyranyl (THP), trityl (triphenylmethyl, Tr), tert-butyldimethylsilyl (TBDMS), triisopropylsilyl (TIPS) ether, and ethoxyethyl ether (EE).

The step 1-1 is a step of preparing a compound represented by Chemical Formula 1-3 by reacting a compound represented by Chemical Formula 1-1 with a compound represented by Chemical Formula 1-2. The reaction is preferably carried out in the presence of a base. Conventional inorganic bases can be used as the base. Non-limiting examples of the inorganic bases may include potassium carbonate, or cesium carbonate. Also, the reaction may be preferably carried out in a polar solvent such as dimethylformamide, dimethylsulfoxide, dioxane or tetrahydrofuran at 0° C. to 100° C. for 10 minutes to 12 hours.

In addition, the compound represented by Chemical Formula 1-1 is commercially available or may be prepared by using a known method (e.g., McLaughlin, and Evans, J. Org Chem, 2010, 75: 518-521), but are not limited thereto.

The step 1-2 is a step of preparing a compound represented by Chemical Formula 1 according to the present invention by subjecting a compound represented by Chemical Formula 1-3 to a deprotection reaction. The reaction is preferably carried out under acidic conditions. Non-limiting examples of the acids may include hydrochloric acid, bromic acid, hydrofluoric acid, trifluoroacetic acid or the like. Preferably, the reaction solvent may or may not use a polar organic solvent. Preferably, when using a polar organic solvent, dichloromethane, chloroform, toluene, dimethylformamide, dioxane, tetrahydrofuran or the like may be used as the solvent, and the reaction can be carried out at room temperature to 100° C. for 10 minutes to 6 hours.

The above reaction scheme 1 may be modified as needed within the range which does not depart from the purpose of the present invention. For example, when a protecting group is needed depending on the substituents, $R_2$, $R_3$ and/Ra, the substituents thereof can be previously protected with a protecting group up to a final step.

As yet another example, the present invention provides a method for preparing the compounds represented by Chemical Formulae 2-10, 2-11, 2-14 or 2-15 among the compounds represented by Chemical Formula 1, as shown in the following Reaction Scheme 2:

[Reaction Scheme 2]

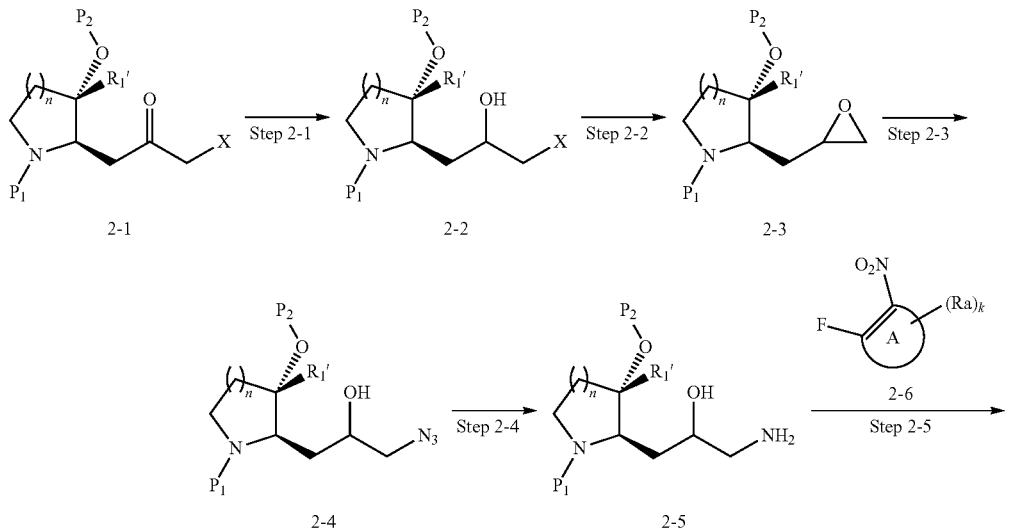

-continued
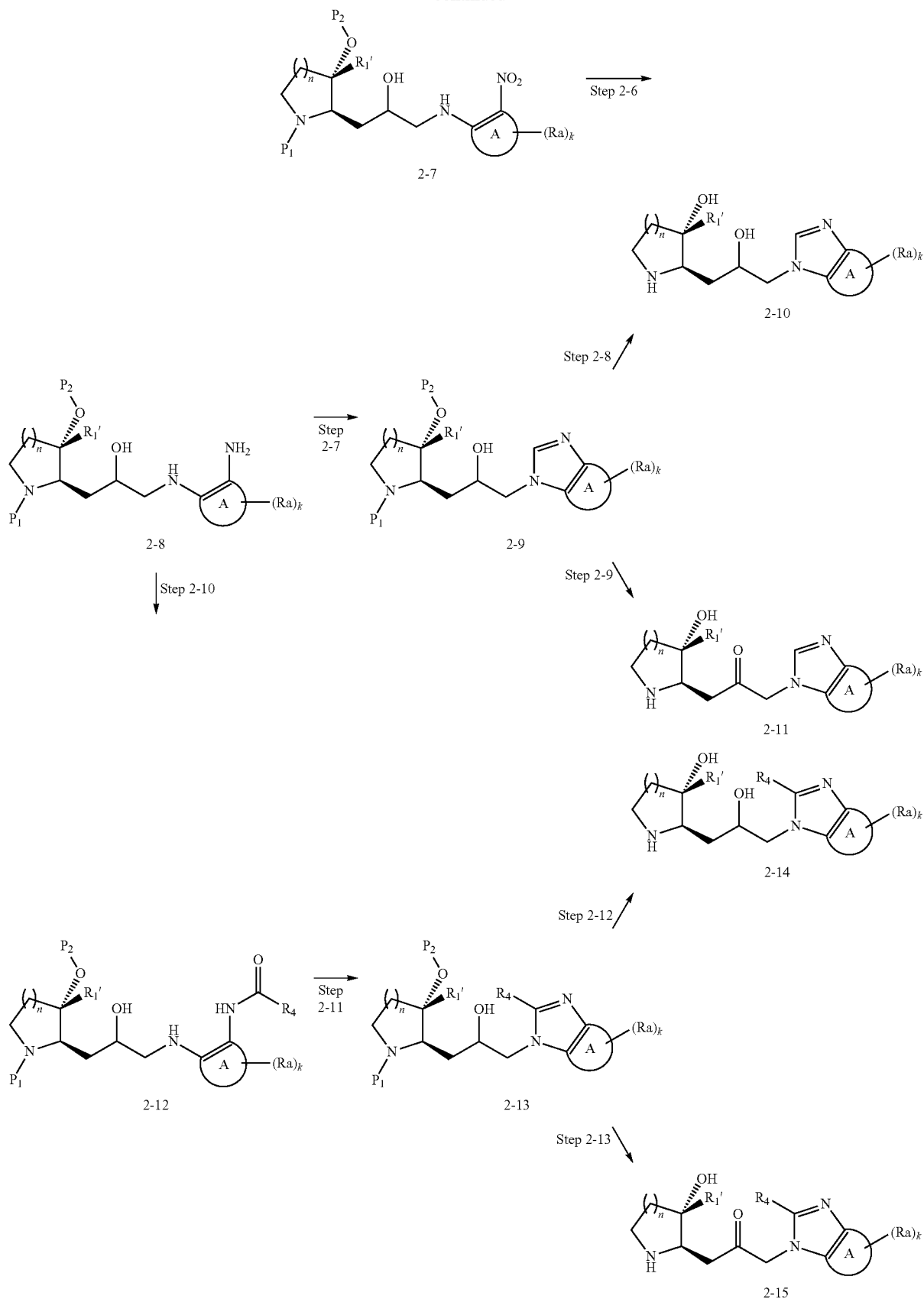

In Reaction Scheme 2, n, $R_1'$, $R_4$, A, Ra and k are as previously defined, $P_1$ and $P_2$ are as defined in Reaction Scheme 1, and X is halogen. Preferably, X is bromo.

The step 2-1 is a step of preparing a compound represented by Chemical Formula 2-2 by reacting a compound represented by Chemical Formula 2-1 in the presence of a base. As the base, a conventional inorganic base can be used, and non-limiting examples thereof may include sodium borohydride, lithium aluminum hydride, sodium carbonate, sodium formate, cerium chloride, or borane-tetrahydrofuran. Further, the reaction may be carried out in a polar solvent such as methanol, ethanol, tetrahydrofuran, acetone, toluene, diethyl ether, or dichloromethane at −78° C. to 20° C. for 10 minutes to 12 hours.

The step 2-2 is a step of preparing a compound represented by Chemical Formula 2-3 by reacting a compound represented by Chemical Formula 2-2 in the presence of a base. As the base, a conventional inorganic base can be used, and non-limiting examples thereof may include potassium hydroxide, lithium hydride, potassium fluoride, sodium hydride, sodium ethoxide, potassium carbonate, or potassium tert-butoxide. In addition, the reaction may be carried out in a polar solvent such as methanol, tetrahydrofuran, acetone, dioxane, diethyl ether, dichloromethane, dimethylformamide, or acetonitrile, at 0° C. to 20° C. for 10 minutes to 24 hours.

The step 2-3 is a step of preparing a compound represented by Chemical Formula 2-4 by reacting a compound represented by Chemical Formula 2-3 under acidic conditions in the presence of sodium azide and/or trimethylsilyl azide. As the acid, a conventional inorganic acid or organic acid can be used, and non-limiting examples thereof may include ammonium chloride, tetrabutyl ammonium chloride, p-toluenesulfonic acid, acetic acid, hydrochloric acid, or sulfuric acid. Further, the reaction can be carried out in a polar solvent such as methanol, ethanol, tert-butanol, acetone, dimethylformamide, acetonitrile, or water at 20° C. to 100° C. for 10 minutes to 48 hours.

The step 2-4 is a step of preparing a compound represented by Chemical Formula 2-5 by reacting a compound represented by Chemical Formula 2-4 in the presence of a base. As the base, a conventional inorganic base can be used, and non-limiting examples thereof may include sodium borohydride, lithium aluminum hydride, palladium, nickel, or triphenylphosphine. Further, the reaction may be carried out in a polar solvent such as methanol, ethanol, tetrahydrofuran, acetone, toluene, dioxane, dimethylformamide, acetonitrile, diethyl ether, dichloromethane, or water at 20° C. to 80° C. for 10 minutes to 18 hours.

The step 2-5 is a step of preparing a compound represented by Chemical Formula 2-7 by reacting a compound represented by Chemical Formula 2-5 and a compound represented by Chemical Formula 2-6 in the presence of a base. As the base, a conventional inorganic base or organic base can be used, and non-limiting examples of the organic base may include diisopropylethylamine or trimethylamine. Non-limiting examples of the inorganic base may include potassium carbonate, sodium carbonate, sodium hydrogen carbonate, cesium carbonate, or calcium carbonate. Further, the reaction may be carried out in a polar solvent such as methanol, ethanol, butanol, tetrahydrofuran, acetone, toluene, dimethylformamide, dimethylformsulfoxide, chloroform, dioxane, acetonitrile, diethyl ether, or dichloromethane at 20° C. to 150° C. for 10 minutes to 24 hours.

The step 2-6 is a step of preparing a compound represented by Chemical Formula 2-8 by reacting a compound represented by Chemical Formula 2-7 in the presence of hydrogen and metal. Non-limiting examples of the metal may include palladium, nickel, or platinum oxide. Further, the reaction can be carried out in a polar solvent such as methanol, ethanol, isopropanol, tetrahydrofuran, dimethylformamide, ethyl acetate, dichloromethane, or water at 5° C. to 50° C. for 10 minutes to 12 hours.

The step 2-7 is a step of preparing a compound represented by Chemical Formula 2-9 by reacting a compound represented by Chemical Formula 2-8 i) in the presence of trimethyl orthoformate or triethyl orthoformate, and para-toluenesulfonic acid or pyridinium para-toluenesulfonate, or ii) in the presence of formic acid. The reaction may be carried out in a polar solvent such as methanol, ethanol, tetrahydrofuran, toluene, dioxane, dimethylformamide, acetone, chloroform, ethyl acetate, dichloromethane, or acetonitrile at 20° C. to 120° C. for 10 minutes to 12 hours.

The step 2-8 is a step of preparing a compound represented by Chemical Formula 2-10 by reacting a compound represented by Chemical Formula 2-9 under acidic conditions. Non-limiting examples of the acid may include hydrochloric acid, bromic acid, hydrofluoric acid, trifluoroacetic acid or the like. Preferably, the reaction solvent may or may not use a polar organic solvent. Preferably, when using a polar organic solvent, dichloromethane, chloroform, toluene, dimethylformamide, dioxane, tetrahydrofuran or the like may be used, and the reaction may be carried out at room temperature to 100° C. for 10 minutes to 6 hours.

The step 2-9 is a step of preparing a compound represented by Chemical Formula 2-11 by i) reacting a compound represented by Chemical Formula 2-9 with an oxidizing agent, and ii) reacting the reaction product in the same manner as in Step 2-8. Non-limiting examples of the oxidizing agent may include Dess-Martin periodinane, hydrogen peroxide, or oxaly chloride. Further, the reaction can be carried out in a polar solvent such as dichloromethane, dimethylformamide, dimethylformsulfoxide, toluene, chloroform, tetrahydrofuran, acetone, acetonitrile diethylether, or ethyl acetate at −78° C. to 30° C. for 10 minutes to 12 hours.

The step 2-10 is a step of preparing a compound represented by Chemical Formula 2-12 by reacting a compound represented by Chemical Formula 2-8 with a $R_4$-substituted carboxylic acid ($R_4$—COOH) in the presence of an amide coupling reagent of bis-(2-oxo-3-oxazolydinyl)phosphoryl hydrochloride, 1-ethyl-(3-(3-dimethylamino)propyl)-carbodiimide hydrochloride, benzotriazol-1-yloxy-tris-(pyrrolidino)phosphonium hexafluorophosphate, benzotriazol-ol, (benzotriazol-1-yloxy)tris(dimethylamino)phosphonium hexafluorophosphate or O-(benzotriazol-1-yl)-N,N,N,N'-tetramethyluronium hexafluorophosphate, and a base of triethylamine, di-isopropyl ethylamine, pyridine, dimethylaniline, dimethylamino pyridine or sodium hydroxide. The reaction may be carried out in a polar solvent such as methanol, ethanol, propanol, tetrahydrofuran, toluene, dioxane, dimethylformamide, dichloromethane, acetonitrile, or acetone at −20° C. to 80° C. for 5 minutes to 18 hours.

The step 2-11 is carried out in the same manner as in the step 2-7, except that the compound represented by Chemical Formula 2-12 is used.

The step 2-12 and step 2-13 are carried out in the same manner as in the step 2-8 and step 2-9, except that the compound represented by Chemical Formula 2-13 is used.

The above reaction scheme 2 may be modified as needed with the range which does not depart from the purpose of the present invention. For example, when a protecting group is needed depending on the substituents, $R_4$ and/or Ra, these substituents can be previously protected with a protecting group up to the final step.

In addition, the present invention provides a compound represented by Chemical Formula 2-9 or a compound represented by Chemical Formula 2-13, as an intermediate which can be used in the preparation of the compound represented by Chemical Formula 1.

[Chemical Formula 2-9]

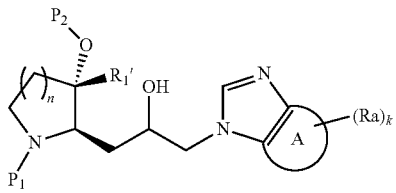

[Chemical Formula 2-13]

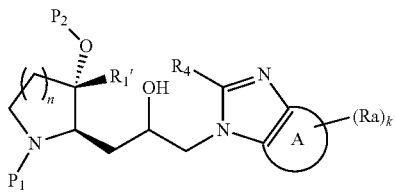

in Chemical Formulae 2-9 and 2-13, $P_1$ and $P_2$ are each independently a protecting group as defined in Reaction Scheme 1, and n, $R_1'$, $R_4$, A, k and Ra are as defined in Chemical Formula 1.

The compound represented by Chemical Formula 2-9 can be prepared by the step 2-5 through step 2-7 of the above-mentioned Reaction Scheme 2. Also, the compound represented by Chemical Formula 2-13 can be prepared by the steps 2-5, 2-6, 2-10 and 2-11 of the above-mentioned Reaction Scheme 2.

In addition, the present invention provides a pharmaceutical composition for the prevention or treatment of cancers, inflammatory diseases, autoimmune diseases or fibrosis, comprising a compound represented by Chemical Formula 1 or a pharmaceutically acceptable salt thereof.

The term "prevention" as used herein refers to any act to delay or inhibit occurrence, spread or recurrence of a cancer, an inflammatory disease, an autoimmune disease or a fibrosis by administration of the composition of the present invention, and "treatment" refers to any act to improve or change the symptoms of the above diseases for the better by administration of the composition of the present invention.

The composition of the present invention can be effectively used in the prevention or treatment of cancer, inflammatory diseases, autoimmune diseases or fibrosis by inhibiting PRS enzymatic activity.

The composition of the present invention can be used in the various forms such as oral dosage forms of powders, granules, tablets, capsules, suspensions, emulsions, syrups, aerosols and injections of a sterile injectable solution, which are formulated by the conventional method according to the purpose of each of the intended use. The composition can be administered through various routes including oral administration or intravenous, intraperitoneal, subcutaneous, rectal and topical administration. Examples of suitable carriers, excipients or diluents which can be included in this composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxy benzoate, propylhydroxy benzoate, talc, magnesium stearate, mineral oil, and the like. In addition, the composition of the present invention may further comprise fillers, anti-coagulants, lubricants, humectants, fragrances, emulsifiers, preservatives, and the like.

A solid formulation for oral administration include tablets, pills, powders, granules, capsules and the like, and such solid dosage forms are formulated by mixing the composition of the present invention with one or more excipients, such as starch, calcium carbonate, sucrose, lactose, gelatin and the like. Also, lubricants such as magnesium stearate and talc can be used other than simple excipients.

A liquid formulation for oral administration can be illustrated as suspensions, solutions, emulsions, syrups and the like, and can include various excipients such as humectants, sweeteners, fragrances, preservatives and the like, in addition to water and liquid paraffin which are commonly used diluents.

A formulation for parenteral administration includes sterilized aqueous solutions, non-aqueous solvents, suspension agents, emulsion agents, lyophilizing agents and suppository agents. Non-aqueous solvent and suspending agent may include propylene glycol, polyethylene glycol, vegetable oil such as olive oil, and injectable esters such as ethyl oleate. As a substrate for the suppository agent, Witepsol, Macrogol, Tween 61, cacao butter, laurin butter, glycerogelatin or the like may be used. On the other hand, injections may include conventional additives such as solubilizing agents, isotonic agents, suspending agents, emulsifiers, stabilizers, or preservatives.

The formulation may be prepared according to conventional mixing, granulation or coating methods, and may contain an active ingredient in the range of about 0.1 to 75% by weight, and preferably about 1 to 50% by weight. The unit formulation for a mammal of about 50 kg to 70 kg contains about 10 mg to 200 mg of an active ingredient.

The composition of the present invention is administrated in a pharmaceutically effective amount. The term "pharmaceutically effective amount" as used herein refers to an amount which is sufficient to treat the disease at a reasonable benefit/risk ratio applicable for any medical treatment, and also which is enough to not cause side effects. The level of effective amount can be determined depending on type and severity of patient's health condition, disease type, severity of the disease, activity of the drug, sensitivity on the drug, administration method, administration time, administration route, excretion rate, treatment duration, combination, factors including other medicines used at the same time and other factors well-known in the medical field. The composition of the present invention may be administered as individual therapy or in combination with other therapies, and it can be administered simultaneously with or sequentially to conventional therapies, and once or multiple times. It is important to administer the minimum amount which can provide the maximum effect without the side effects in consideration of all the above factors, which can be easily determined by those skilled in the art.

A preferred dose of the compound according to the present invention may be varied according to the condition and weight of a patient, the severity of a disease, the type of a drug, and the route and duration of administration, but it may be suitably selected by those skilled in the art. In order to achieve desirable effects, however, the compound of the present invention may be administered daily at a dose of 0.0001 to 100 mg/kg (body weight), and preferably 0.001 to 100 mg/kg (body weight). The administration may be performed once a day or in divided doses each day through an oral or parenteral route.

Furthermore, the present invention provides a method for preventing or treating cancer, inflammatory diseases, autoimmune diseases or fibrosis in a subject, comprising administrating the above-described pharmaceutical composition to a subject in need thereof.

As used herein, the term "subject" refers to an animal comprising human, monkey, cow, horse, sheep, pig, chicken, turkey, quail, cat, dog, mouse, rat, rabbit, or guinea pig, which have the cancer or potentially has the cancer. The above diseases can be effectively prevented or treated by administrating the pharmaceutical composition of the present invention to the subject. The pharmaceutical composition of the present invention can be administered in combination with conventional therapeutic agents.

As used herein, the term "administration" means introduction of a prescribed amount of a substance into a patient in certain appropriate method, and the composition of the present invention can be administrated via any of the general routes as long as it can reach a target tissue. Specifically, a variety of administration modes are contemplated, including intraperitoneally, intravenously, intramuscularly, subcutaneously, intradermally, orally, topically, intranasally, intrapulmonarily and intrarectally, but the present invention is not limited to these exemplified administration modes. Also, the pharmaceutical composition of the present invention can be administered using any device capable of delivering the active ingredients to target cells. Preferable administration mode and formulation are an intravenous injection, a subcutaneous injection, an intradermal injection, an intramuscular injection, instillation, or the like. Injectable formulations may be prepared using saline, aqueous solutions such as Ringer's solution, and non-aqueous solutions, such as vegetable oils, high fatty acid esters (e.g., ethyl oleic acid, etc.), alcohols (e.g., ethanol, benzyl alcohol, propylene glycol, glycerin, etc.). The injectable preparations may comprises pharmaceutical carriers, including a stabilizer for preventing degeneration (e.g., ascorbic acid, sodium hydrogen sulfite, sodium pyrosulfite, BHA, tocopherol, EDTA, etc.), an emulsifier, a buffering agent for pH control, and a preservative for inhibiting microbial growth (e.g., phenylmercuric nitrate, thimerosal, benzalkonium chloride, phenol, cresol, benzylalcohol, etc.).

Advantageous Effects

The novel heterocyclic compound of the present invention can suppress selectively PRS enzymatic activity, and thus it can be effectively used for the prevention and treatment of cancer, inflammatory diseases, autoimmune diseases or fibrosis, which are diseases caused by abnormality in PRS activity.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 illustrates the measured results of the numbers of local lytic and necrotic cardiac muscle fibers per unit number of myofibers of the left ventricle of mouse, which shows the effect of the compound according to one example of the present invention.

FIGS. 2 and 3 illustrate the measured results of percentages of collagen fibers per unit area of mouse, which shows the effect of the compound according to one example of the present invention.

FIG. 4 illustrates the measured results of mRNA expression level of mouse transforming growth factor-beta1 (TGF-ß1), which shows the effect of the compound according to one example of the present invention.

DETAILED DESCRIPTION OF THE EMBODIMENTS

Hereinafter, preferred Examples are provided for better understanding of the invention. However, the following Examples are for illustrative purposes only, and the invention is not intended to be limited by these Examples.

Example 1: Preparation of 1-(1H-benzo[d]imidazol-1-yl)-3-((2R,3S)-3-hydroxypiperidin-2-yl)propan-2-one

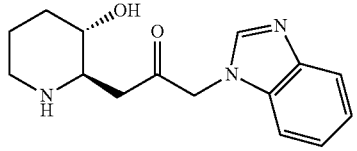 [SMILES: O=C(C[C@H]1NCCC[C@@H]1O)Cn1cnc2ccccc21]

(Step 1-1) Preparation of benzyl (2R,3S)-2-(3-(1H-benzo[d]imidazol-1-yl)-2-oxopropyl)-3-(tert-butyldimethylsilyloxy)piperidin-1-carboxylate 1H-benzo[d]imidazole (50 mg, 0.42 mmol) was dissolved in N,N-dimethylformamide (2 mL) to which potassium carbonate (120 mg, 0.85 mmol) was added and stirred at room temperature for 10 minutes. Then, benzyl (2R,3S)-2-(3-bromo-2-oxopropyl)-3-(tert-butyldimethylsilyloxy)piperidin-1-carboxylate (210 mg, 0.42 mmol) was added thereto and stirred at room temperature for 3 hours. When the reaction was completed, the solvent was removed, and the resulting mixture was diluted with ethyl acetate and then washed with saturated sodium chloride solution. The organic layer was collected, dried over magnesium sulfate, filtered and concentrated under reduced pressure, and then purified by column chromatography (dichloromethane:methanol=10:1) to obtain the title compound (180 mg, yield: 80%).

(Step 1-2) Preparation of 1-(1H-benzo[d]imidazol-1-yl)-3-((2R,3S)-3-hydroxypiperidin-2-yl)propan-2-one Benzyl (2R,3S)-2-(3-(1H-benzo[d]imidazol-1-yl)-2-oxopropyl)-3-(tert-butyldimethylsilyloxy)piperidin-1-carboxylate (180 mg, 0.34 mmol) obtained from Step 1-1 was dissolved in 6N hydrochloric acid solution (4 mL) and then stirred under reflux for 1 hour. When the reaction was completed, the reaction solution was cooled to 0° C., neutralized with potassium carbonate (pH 7), and extracted with a mixed solution of chloroform and a small amount of acetone. The organic layer was collected, dried over magnesium sulfate, filtered and concentrated under reduced pressure, and then recrystallized with diethyl ether to obtain the title compound (66 mg, yield: 70%).

$^1$H-NMR (500 MHz, DMSO-d$_6$): δ 8.18 (s, 1H), 7.64 (d, 1H), 7.45 (d, 1H), 7.18 (m, 2H), 5.32 (s, 2H), 4.83 (m, 1H), 3.00 (m, 1H), 2.94 (dd, 1H), 2.83 (d, 1H), 2.69 (m, 1H), 2.42 (m, 2H), 1.89 (m, 1H), 1.49 (m, 1H), 1.35 (m, 1H), 1.25 (m, 1H).

Example 2: Preparation of 1-(5-chloro-1H-benzo[d]imidazol-1-yl)-3-((2R,3S)-3-hydroxypiperidin-2-yl)propan-2-one

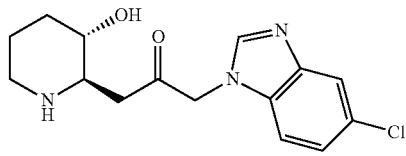 [SMILES: O=C(C[C@H]1NCCC[C@@H]1O)Cn1cnc2cc(Cl)ccc21]

(Step 2-1) Preparation of benzyl (2R,3S)-3-(tert-butyldimethylsilyloxy)-2-(3-(5-chloro-1H-benzo[d]imidazol-1-yl)-2-oxopropyl)-piperidin-1-carboxylate The compound, which was obtained in the same manner as in Step 1-1 of Example 1 except that 5-chloro-1H-benzo[d]imidazole was used instead of 1H-benzo[d]imidazole, was separated via supercritical fluid chromatography to obtain the title compound (38 mg, yield: 41%) (separation condition: carbon dioxide/ethanol/diethanolamine=70/30/0.1 (v/v/v), flow rate: 2.5 mL/min, temperature: 35° C., compound peak retention time=8.5 min).

$^1$H-NMR (400 MHz, DMSO-d$_6$): δ 8.14 (s, 1H), 7.75 (s, 1H), 7.48 (dd, 1H), 7.29 (m, 6H), 5.34 (t, 1H), 5.18-5.00 (m, 2H), 4.61 (t, 1H), 3.95 (m, 1H), 3.79 (dd, 1H), 3.12 (dd, 1H), 2.96-2.85 (m, 2H), 1.78 (m, 2H), 1.52 (d, 1H), 1.37 (m, 1H), 0.82 (d, 9H), 0.02 (m, 6H).

(Step 2-2) Preparation of 1-(5-chloro-1H-benzo[d]imidazol-1-yl)-3-((2R,3S)-3-hydroxypiperidin-2-yl)propan-2-one The reaction was carried out in the same manner as in Step 1-2 of Example 1, except that benzyl (2R,3S)-3-(tert-butyldimethylsilyloxy)-2-(3-(5-chloro-1H-benzo[d]imidazol-1-yl)-2-oxopropyl)-piperidin-1-carboxylate obtained from Step 2-1 was used instead of benzyl (2R,3S)-2-(3-(1H-benzo[d]imidazol-1-yl)-2-oxopropyl)-3-(tert-butyldimethylsilyloxy)piperidin-1-carboxylate, thereby obtaining the title compound (15 mg, yield: 85%).

$^1$H-NMR (500 MHz, DMSO-d$_6$): δ 8.08 (s, 1H), 7.66 (dd, 2H), 7.20 (dd, 1H), 5.33 (dd, 2H), 4.82 (d, 1H), 3.01 (m, 1H), 2.95 (dd, 1H), 2.83 (d, 1H), 2.66 (m, 1H), 2.41 (m, 2H), 2.13 (s, 1H), 1.90 (dd, 1H), 1.59 (d, 1H), 1.35 (m, 1H), 1.25 (m, 1H).

Example 3: Preparation of 1-(6-chloro-1H-benzo[d]imidazol-1-yl)-3-((2R,3S)-3-hydroxypiperidin-2-yl)propan-2-one

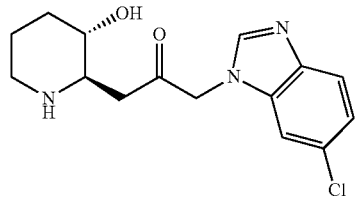

(Step 3-1) Preparation of benzyl (2R,3S)-3-(tert-butyldimethylsilyloxy)-2-(3-(6-chloro-1H-benzo[d]imidazol-1-yl)-2-oxopropyl)-piperidin-1-carboxylate The compound was obtained from Step 2-1 of Example 2 was separated via supercritical fluid chromatography (compound peak retention time=8.09 min) under the same separation conditions as Step 2-1 of Example 2, thereby obtaining the title compound (35 mg, yield: 38%).

$^1$H-NMR (500 MHz, DMSO-d$_6$): δ 8.07 (s, 1H), 7.66-7.59 (m, 2H), 7.30-7.19 (m, 6H), 5.29 (m, 1H), 5.16-4.97 (m, 2H), 4.60 (t, 1H), 3.90 (m, 1H), 3.76 (dd, 1H), 3.10 (m, 1H), 2.88 (m, 2H), 1.75 (m, 2H), 1.49 (d, 1H), 1.34 (m, 1H), 0.78 (d, 9H), −0.02 (m, 6H).

(Step 3-2) Preparation of 1-(6-chloro-1H-benzo[d]imidazol-1-yl)-3-((2R,3S)-3-hydroxypiperidin-2-yl)propan-2-one The reaction was carried out in the same manner in Step 1-2 of Example 1, 1-2 of Example 1, except that benzyl (2R,3S)-3-(tert-butyldimethylsilyloxy)-2-(3-(6-chloro-1H-benzo[d]imidazol-1-yl)-2-oxopropyl)-piperidin-1-carboxylate was used instead of benzyl (2R,3S)-2-(3-(1H-benzo[d]imidazol-1-yl)-2-oxopropyl)-3-(tert-butyldimethylsilyloxy)piperidin-1-carboxylate, thereby obtaining the title compound (17 mg, yield: 81%).

$^1$H-NMR (500 MHz, DMSO-d$_6$): δ 8.11 (s, 1H), 7.70 (d, 1H), 7.50 (d, 1H), 7.25 (dd, 1H), 5.34 (dd, 2H), 4.82 (d, 1H), 3.01 (m, 1H), 2.93 (dd, 1H), 2.81 (d, 1H), 2.66 (m, 1H), 2.38 (m, 2H), 2.08 (s, 1H), 1.90 (d, 1H), 1.58 (d, 1H), 1.34 (m, 1H), 1.24 (m, 1H).

Example 4: Preparation of 1-(5-bromo-1H-benzo[d]imidazol-1-yl)-3-((2R,3S)-3-hydroxypiperidin-2-yl)propan-2-one

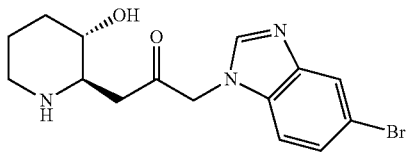

(Step 4-1) Preparation of benzyl (2R,3S)-2-(3-bromo-2-hydroxypropyl)-3-(tert-butyldimethylsilyloxy)piperidin-1-carboxylate Benzyl (2R,3S)-2-(3-bromo-2-oxopropyl)-3-(tert-butyldimethylsilyloxy)piperidin-1-carboxylate (5.0 g, 10.3 mmol) was dissolved a mixed solvent of methanol and tetrahydrofuran (1:1) (20 mL) and then cooled to 0° C. Then, sodium borohydride (390 mg, 10.3 mmol) was added thereto and stirred at 0° C. for 30 minutes. The temperature was raised to room temperature and the mixture was further stirred for 12 hours. When the reaction was completed, subsequent reactions were carried out without purification procedures.

(Step 4-2) Preparation of benzyl (2R,3S)-3-(tert-butyldimethylsilyloxy)-2-(oxirane-2-ylmethyl)piperidin-1-carboxylate Potassium hydroxide (200 mg, 3.6 mmol) dissolved in a small amount of water was added to benzyl (2R,3S)-2-(3-bromo-2-hydroxypropyl)-3-(tert-butyldimethylsilyloxy)piperidin-1-carboxylate reaction solution obtained from Step 4-1, and then stirred at room temperature for 1 hour. When the reaction was completed, the solvent was removed, and the resulting mixture was diluted with ethyl acetate and then washed with saturated sodium chloride solution. The organic layer was collected, dried over magnesium sulfate, filtered and concentrated under reduced pressure, and then purified by column chromatography (hexane:ethyl acetate=4:1) to obtain the title compound (3.4 g, two step yield: 81%).

(Step 4-3) Preparation of benzyl (2R,3S)-2-(-3-azido-2-hydroxypropyl)-3-(tert-butyldimethylsilyloxy)piperidin-1-carboxylate Benzyl (2R,3S)-3-(tert-butyldiemthylsilyl)oxy)-2-(oxiran-2-ylmethyl)piperidin-1-carboxylate (3.4 g, 8.4 mmol) obtained from Step 4-2 was dissolved in a mixed solvent of methanol and water (8:1) (90 mL), to which sodium azide (2.7 g, 41 mmol) and ammonium chloride (1.3 g, 25 mmol) were added, and then stirred under reflux at 70° C. for 6 hours. When the reaction was completed, the reaction mixture was diluted with ethyl acetate and then washed with saturated sodium chloride solution. The organic layer was collected, dried over magnesium sulfate, filtered and then concentrated under reduced pressure, and then purified by column chromatography (hexane:ethyl acetate=3:1) to obtain the title compound (3.8 g, yield: 98%).

(Step 4-4) Preparation of benzyl (2R,3S)-2-(-3-amino-2-hydroxypropyl)-3-(tert-butyldimethylsilyloxy)piperidin-1-carboxylate Benzyl (2R,3S)-2-((S)3-azido-2-hydroxypropyl)-3-(tert-butyldimethylsilyloxy)piperidin-1-carboxylate (1.5 g, 3.3 mmol) obtained from Step 4-3 was dissolved in a mixed solvent of tetrahydrofuran and water (8:2)(50 mL) to which triphenyl phosphine (1.8 g, 6.7 mmol) was added and then stirred at room temperature for 6 hours. When the reaction was completed, the reaction mixture was diluted with ethyl acetate and washed with saturated sodium chloride solution. The organic layer was collected, dried over magnesium sulfate, filtered and concentrated under reduced pressure, and then purified by column chromatography (dichloromethane:methanol=9:1) to obtain the title compound (1.2 g, yield: 81%).

(Step 4-5) Preparation of benzyl (2R,3S)-2-(-3-((4-bromo-2-nitrophenyl)amino)-2-hydroxypropyl)-3-(tert-butyldimethylsilyloxy)piperidin-1-carboxylate Benzyl (2R,3S)-2-(-3-amino-2-hydroxypropyl)-3-(tert-butyldimethylsilyloxy)piperidin-1-carboxylate (120 mg, 0.27 mmol) obtained from Step 4-4 was dissolved in N,N-dimethylformamide (1 mL) to which 4-bromo-1-fluoro-2-nitrobenzene (59 mg, 0.27 mmol) and diisopropyl ethylamine (94 mg, 0.54 mmol) were added and then stirred under reflux at 80° C. for 6 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=2:1) to obtain the title compound (120 mg, yield: 71%).

(Step 4-6) Preparation of benzyl (2R,3S)-2-(3-((2-amino-4-bromophenyl)amino)-2-hydroxypropyl)-3-(tert-butyldimethylsilyloxy)piperidin-1-carboxylate Benzyl (2R,3S)-2-(-3-((4-bromo-2-nitrophenyl)amino)-2-hydroxypropyl)-3-(tert-butyldimethylsilyloxy)piperidin-1-carboxylate (120 mg, 0.19 mmol) obtained from Step 4-5 was dissolved in methanol (6 mL) to which an appropriate amount of Raney nickel was added. After connecting a hydrogen balloon, the mixture was stirred at room temperature for 1 hour. When the reaction was completed, the reaction solution was filtered through celite and concentrated under reduced pressure. Subsequent reactions were carried out without purification procedure.

(Step 4-7) Preparation of benzyl (2R,3S)-2-(-3-(5-bromo-1H-benzo[d]imidazol-1-yl)-2-hydroxypropyl)-3-(tert-butyldimethylsilyloxy)piperidin-1-carboxylate Benzyl (2R,3S)-2-(-3-((2-amino-4-bromophenyl)amino)-2-hydroxypropyl)-3-(tert-butyldimethylsilyloxy)piperidin-1-carboxylate (120 mg, 0.20 mmol) obtained from Step 4-6 was dissolved in toluene (1 mL) to which papa-toluene sulfonic acid (7 mg, 0.04 mmol) and triethylorthoformate (100 uL, 0.42 mmol) were added and then stirred at 40° C. for 12 hours. When the reaction was completed, the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=1:2) to obtain the title compound (64 mg, two step yield: 55%).

(Step 4-8) Preparation of benzyl (2R,3S)-2-(3-(5-bromo-1H-benzo[d]imidazol-1-yl)-2-oxopropyl)-3-((tert-butyldimethylsilyloxy)piperidin-1-carboxylate Benzyl (2R,3S)-2-(3-(5-bromo-1H-benzo[d]imidazol-1-yl)-2-oxopropyl)-3-(tert-butyldimethylsilyloxy)piperidin-1-carboxylate (64 mg, 0.11 mmol) obtained from Step 4-7 was dissolved in dichloromethane (1 mL) to which 1,1,1-triacetoxy-1,1-dihydro-1,2-benziodoxol-3(1H)-one (54 mg, 0.13 mmol) was added and then stirred at room temperature for 3 hours. When the reaction was completed, the resulting mixture was diluted with ethyl acetate and washed with saturated sodium chloride solution. The organic layer was collected, dried over magnesium sulfate, filtered and concentrated under reduced pressure, and then purified by column chromatography (dichloromethane:methanol=15:1) to obtain the title compound (49 mg, yield: 77%).

Step 4-9: Preparation of 1-(5-bromo-1H-benzo[d]imidazol-1-yl)-3-((2R,3S)-3-hydroxypiperidin-2-yl)propan-2-one Benzyl (2R,3S)-2-(tert-butyldimethylsilyloxy)-2-(2-oxo-3-(4-phenyl-1H-benzo[d]imidazole-1-yl)propyl)piperidin-1-carboxylate (49 mg, 0.08 mmol) obtained from Step 4-8 was dissolved in 6N hydrochloric acid solution (2 mL) and then stirred under reflux for 1 hour. When the reaction was completed, the reaction solution was cooled to 0° C., neutralized (pH 7) with potassium carbonate and then extracted with a mixed solution of chloroform and a small amount of acetone. The organic layer was collected, dried over magnesium sulfate, filtered and concentrated under reduced pressure, and then recrystallized with diethylether to obtain the title compound (20 mg, yield: 70%).

$^1$H-NMR (500 MHz, DMSO-d$_6$): δ 8.09 (s, 1H), 7.84 (d, 1H), 7.36 (dd, 1H), 5.33 (dd, 2H), 4.82 (d, 1H), 2.98 (m, 1H), 2.92 (dd, 1H), 2.82 (d, 1H), 2.67 (m, 1H), 2.39 (m, 1H), 1.90 (m, 1H), 1.59 (d, 1H), 1.35 (m, 1H), 1.22 (m, 1H).

Example 5: Preparation of 1-(6-bromo-1H-benzo[d]imidazol-1-yl)-3-((2R,3S)-3-hydroxypiperidin-2-yl)propan-2-one

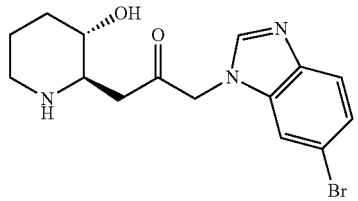 [SMILES: O=C(C[C@H]1NCCC[C@@H]1O)Cn1cnc2ccc(Cl)cc21]

The reaction was carried out in the same manner as in Step 4-1 to Step 4-9 of Example 4, except that 4-bromo-2-fluoro-1-nitrobenzene was used instead of 4-bromo-1-fluoro-2-nitrobenzene in Step 4-5 of Example 4, thereby obtaining the title compound (8 mg, yield: 61%).

$^1$H-NMR (500 MHz, DMSO-d$_6$): δ 8.05 (s, 1H), 7.79 (d, 1H), 7.58 (s, 1H), 7.29 (dd, 1H), 5.33 (m, 2H), 4.84 (d, 1H), 3.02 (m, 1H), 2.93 (dd, 1H), 2.84 (m, 1H), 2.67 (m, 2H), 2.39 (m, 1H), 2.11 (s, 1H), 1.92 (m, 1H), 1.59 (m, 1H), 1.39 (m, 1H), 1.28 (m, 1H).

Example 6: Preparation of 1-((2R,3S)-3-hydroxypiperidin-2-yl)-3-(5-(trifluoromethyl)-1H-benzo[d]imidazol-1-yl)propan-2-one

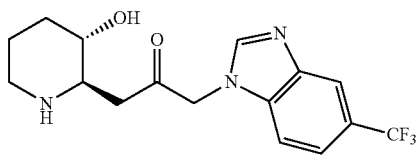 [SMILES: O=C(C[C@H]1NCCC[C@@H]1O)Cn1cnc2cc(C(F)(F)F)ccc21]

The reaction was carried out in the same manner as in Step 4-1 to Step 4-9 of Example 4, except that 1-fluoro-2-nitro-4-(trifluoromethyl)benzene was used instead of 4-bromo-1-fluoro-2-nitrobenzene in Step 4-5 of Example 4, thereby obtaining the title compound (9 mg, yield: 47%).

$^1$H-NMR (500 MHz, DMSO-d$_6$): δ 8.26 (s, 1H), 8.03 (s, 1H), 7.79 (d, 1H), 7.56 (d, 1H), 5.42 (m, 2H), 4.85 (d, 1H), 3.03 (m, 1H), 2.94 (dd, 1H), 2.82 (m, 1H), 2.67 (m, 1H), 2.44 (m, 1H), 2.37 (m, 1H), 1.91 (m, 1H), 1.59 (m, 1H), 1.37 (m, 1H), 1.23 (m, 1H).

Example 7: Preparation of 1-((2R,3S)-3-hydroxypiperidin-2-yl)-3-(6-(trifluoromethyl)-1H-benzo[d]imidazol-1-yl)propan-2-one

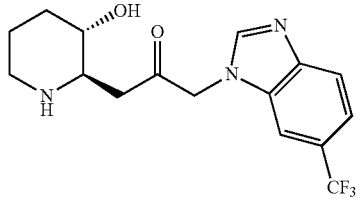 [SMILES: O=C(C[C@H]1NCCC[C@@H]1O)Cn1cnc2ccc(C(F)(F)F)cc21]

The reaction was carried out in the same manner as in Step 4-1 to Step 4-9 of Example 4, except that 2-fluoro-1-nitro-4-(trifluoromethyl)benzene was used instead of 4-bromo-1-fluoro-2-nitrobenzene in Step 4-5 of Example 4, thereby obtaining the title compound (15 mg, yield: 58%).

$^1$H-NMR (500 MHz, DMSO-d$_6$): δ 8.28 (s, 1H), 8.26 (s, 1H), 7.85 (d, 1H), 7.51 (d, 1H), 5.44 (m, 2H), 4.82 (d, 1H), 3.03 (m, 1H), 2.96 (dd, 1H), 2.83 (d, 1H), 2.68 (m, 1H), 2.45 (m, 1H), 2.39 (m, 1H), 1.92 (m, 1H), 1.60 (m, 1H), 1.38 (m, 1H), 1.24 (m, 1H).

Example 8: Preparation of 1-((2R,3S)-3-hydroxypiperidin-2-yl)-3-(7-(trifluoromethyl)-1H-benzo[d]imidazol-1-yl)propan-2-one

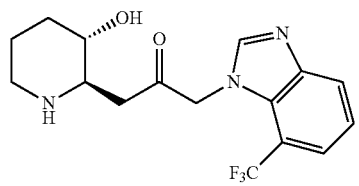 [SMILES: O=C(C[C@H]1NCCC[C@@H]1O)Cn1cnc2cccc(C(F)(F)F)c21]

The reaction was carried out in the same manner as in Step 4-1 to Step 4-9 of Example 4, except that 2-fluoro-1-nitro-3-(trifluoromethyl)benzene was used instead of 4-bromo-1-fluoro-2-nitrobenzene in Step 4-5 of Example 4, thereby obtaining the title compound (14 mg, yield: 70%).

$^1$H-NMR (500 MHz, DMSO-d$_6$): δ 8.28 (s, 1H), 8.26 (s, 1H), 7.85 (d, 1H), 7.51 (d, 1H), 5.44 (m, 2H), 4.82 (d, 1H), 3.03 (m, 1H), 2.96 (dd, 1H), 2.83 (d, 1H), 2.68 (m, 1H), 2.45 (m, 1H), 2.39 (m, 1H), 1.92 (m, 1H), 1.60 (m, 1H), 1.38 (m, 1H), 1.24 (m, 1H).

Example 9: Preparation of 1-(5,6-dimethyl-1H-benzo[d]imidazol-1-yl)-3-((2R,3S)-3-hydroxypiperidin-2-yl)propan-2-one

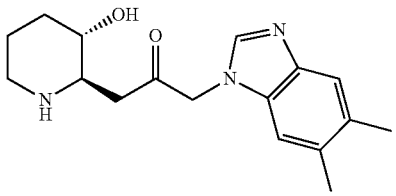 [SMILES: Cc1cc2ncn(CC(=O)C[C@H]3NCCC[C@@H]3O)c2cc1C]

The reaction was carried out in the same manner as in Step 1-1 and Step 1-2 of Example 1, except that 5,6-dimethyl-1H-benzo[d]imidazole was used instead of 1H-benzo[d]imidazole, thereby obtaining the title compound (25 mg, yield: 63%).

$^1$H-NMR (500 MHz, CDCl$_3$-d): δ 7.70 (s, 1H), 7.53 (s, 1H), 6.97 (s, 1H), 3.15-3.20 (m, 1H), 2.96 (dd, 1H), 2.91 (m, 1H), 2.79 (m, 1H), 2.53 (m, 1H), 2.39 (m, 1H), 2.31 (d, 6H), 2.01 (m, 2H), 1.69 (m, 2H), 1.46 (m, 2H).

Example 10: Preparation of 1-(5,6-difluoro-1H-benzo[d]imidazol-1-yl)-3-((2R,3S)-3-hydroxypiperidin-2-yl)propan-2-one

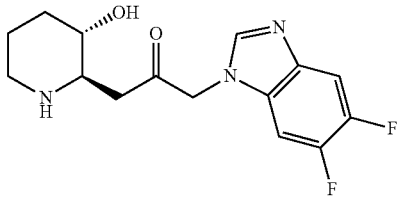 [SMILES: O=C(C[C@H]1NCCC[C@@H]1O)Cn1cnc2cc(F)c(F)cc21]

The reaction was carried out in the same manner as in Step 1-1 and Step 1-2 of Example 1, except that 5,6-difluoro-1H-benzo[d]imidazole was used instead of 1H-benzo[d]imidazole, thereby obtaining the title compound (11 mg, yield: 64%).

$^1$H-NMR (500 MHz, CDCl$_3$-d): δ 7.70 (s, 1H), 7.57 (s, 1H), 7.07 (s, 1H), 3.15-3.20 (m, 1H), 2.96 (dd, 1H), 2.91 (m, 1H), 2.79 (m, 1H), 2.53 (m, 1H), 2.39 (m, 1H), 2.31 (d, 6H), 2.01 (m, 2H), 1.69 (m, 2H), 1.46 (m, 2H).

Example 11: Preparation of 1-(4,5-difluoro-1H-benzo[d]imidazol-1-yl)-3-((2R,3S)-3-hydroxypiperidin-2-yl)propan-2-one

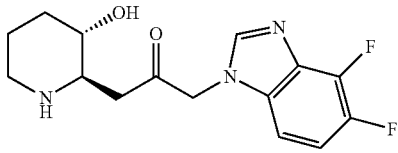 [SMILES: O=C(C[C@H]1NCCC[C@@H]1O)Cn1cnc2c(F)c(F)ccc21]

The reaction was carried out in the same manner as in Step 1-1 and Step 1-2 of Example 1, except that 4,5-difluoro-1H-benzo[d]imidazole was used instead of 1H-benzo[d]imidazole, thereby obtaining the title compound (30 mg, yield: 60%).

$^1$H-NMR (500 MHz, DMSO-d$_6$): δ 8.16 (s, 1H), 7.22-7.5 (m, 2H), 5.77 (m, 2H), 4.82 (d, 1H), 3.00 (m, 1H), 2.98 (m, 1H), 2.81 (m, 1H), 2.66 (m, 1H), 2.35-2.42 (m, 2H), 1.91 (m, 1H), 1.58 (m, 1H), 1.35 (m, 1H), 1.26 (m, 1H).

Example 12: Preparation of 1-(4,5-dichloro-1H-benzo[d]imidazol-1-yl)-3-((2R,3S)-3-hydroxypiperidin-2-yl)propan-2-one

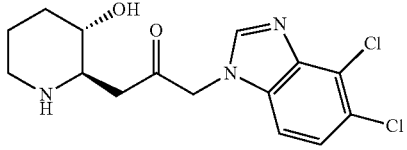 [SMILES: O=C(C[C@H]1NCCC[C@@H]1O)Cn1cnc2c(Cl)c(Cl)ccc21]

The reaction was carried out in the same manner as in Step 1-1 and Step 1-2 of Example 1, except that 4,5-chloro-1H-benzo[d]imidazole was used instead of 1H-benzo[d]imidazole, thereby obtaining the title compound (32 mg, yield: 70%).

$^1$H-NMR (500 MHz, DMSO-d$_6$): δ 8.20 (s, 1H), 7.51 (d, 1H), 7.44 (d, 1H), 5.39 (dd, 2H), 5.02 (s, 1H), 3.11 (m, 1H), 2.98 (dd, 1H), 2.90 (d, 1H), 2.81 (m, 1H), 1.91 (m, 1H), 1.64 (d, 1H), 1.43 (m, 1H), 1.29 (m, 1H).

Example 13: Preparation of 1-(5-fluoro-4-methyl-1H-benzo[d]imidazol-1-yl)-3-((2R,3S)-3-hydroxypiperidin-2-yl)propan-2-one

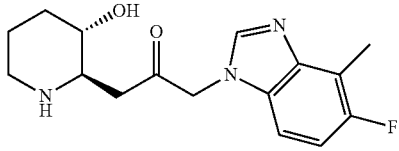 [SMILES: Cc1c(F)ccc2c1ncn2CC(=O)C[C@H]1NCCC[C@@H]1O]

The reaction was carried out in the same manner as in Step 1-1 and Step 1-2 of Example 1, except that 5-fluoro-4-methyl-1H-benzo[d]imidazole was used instead of 1H-benzo[d]imidazole, thereby obtaining the title compound (15 mg, yield: 55%).

$^1$H-NMR (500 MHz, DMSO-d$_6$): δ 8.05 (s, 1H), 7.25 (m, 1H), 7.02 (t, 1H), 5.28 (dd, 2H), 4.79 (d, 1H), 2.99 (m, 1H), 2.89 (m, 1H), 2.79 (d, 1H), 2.64 (m, 1H), 2.50 (s, 3H), 2.41 (m, 1H), 2.05 (m, 1H), 1.88 (d, 1H), 1.55 (d, 1H), 1.33 (m, 1H), 1.25 (m, 1H).

Example 14: Preparation of 1-(5-chloro-4-methyl-1H-benzo[d]imidazol-1-yl)-3-((2R,3S)-3-hydroxypiperidin-2-yl)propan-2-one

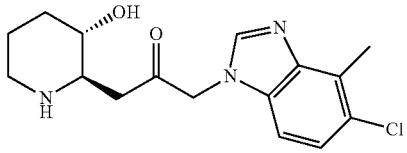 [SMILES: Cc1c(Cl)ccc2c1ncn2CC(=O)C[C@H]1NCCC[C@@H]1O]

The reaction was carried out in the same manner as in Step 1-1 and Step 1-2 of Example 1, except that 5-chloro- 4-methyl-1H-benzo[d]imidazole was used instead of 1H-benzo[d]imidazole, thereby obtaining the title compound (17 mg, yield: 60%).

¹H-NMR (500 MHz, DMSO-d₆): δ 8.06 (s, 1H), 7.30 (d, 1H), 7.22 (d, 1H), 5.30 (s, 2H), 4.79 (m, 1H), 2.99 (m, 1H), 2.88 (m, 1H), 2.78 (d, 1H), 2.64 (m, 1H), 2.49 (s, 3H), 2.36 (m, 2H), 1.88 (m, 1H), 1.58 (m, 1H), 1.34 (m, 1H), 1.23 (m, 1H).

Example 15: Preparation of 1-(5-bromo-4-methyl-1H-benzo[d]imidazol-1-yl)-3-((2R,3S)-3-hydroxypiperidin-2-yl)propan-2-one

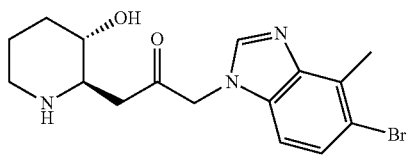 [SMILES: Cc1c(Br)ccc2c1ncn2CC(=O)C[C@H]1NCCC[C@@H]1O]

The reaction was carried out in the same manner as in Step 1-1 and Step 1-2 of Example 1, except that 5-bromo-4-methyl-1H-benzo[d]imidazole was used instead of 1H-benzo[d]imidazole, thereby obtaining the title compound (29 mg, yield: 91%).

¹H-NMR (500 MHz, DMSO-d₆): δ 8.06 (s, 1H), 7.38 (d, 1H), 7.27 (d, 1H), 5.32 (m, 2H), 5.81 (d, 1H), 3.00 (m, 1H), 2.91 (dd, 1H), 2.81 (d, 1H), 2.66 (m, 1H), 2.59 (s, 3H), 2.41 (m, 2H), 1.90 (m, 1H), 1.58 (m, 1H), 1.34 (m, 1H), 1.25 (m, 1H).

Example 16: Preparation of 1-(4,5-dimethyl-1H-benzo[d]imidazol-1-yl)-3-((2R,3S)-3-hydroxypiperidin-2-yl)propan-2-one

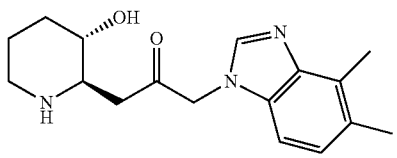 [SMILES: Cc1ccc2c(ncn2CC(=O)C[C@H]2NCCC[C@@H]2O)c1C]

The reaction was carried out in the same manner as in Step 1-1 and Step 1-2 of Example 1, except that 4,5-dimethyl-1H-benzo[d]imidazole was used instead of 1H-benzo[d]imidazole, thereby obtaining the title compound (33 mg, yield: 72%).

¹H-NMR (500 MHz, DMSO-d₆): δ 7.93 (s, 1H), 7.13 (d, 1H), 7.00 (d, 1H), 5.24 (dd, 2H), 4.79 (d, 1H), 3.00 (m, 1H), 2.90 (dd, 1H), 2.81 (d, 1H), 2.64 (m, 1H), 2.46 (s, 3H), 2.39 (m, 2H), 2.32 (s, 3H), 1.90 (m, 1H), 1.58 (m, 1H), 1.33 (m, 1H), 1.21 (m, 1H).

Example 17: Preparation of 1-(5-fluoro-4-(trifluoromethyl)-1H-benzo[d]imidazol-1-yl)-3-((2R,3S)-3-hydroxypiperidin-2-yl)propan-2-one

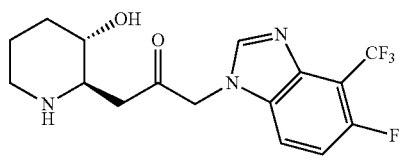

The reaction was carried out in the same manner as in Step 1-1 and Step 1-2 of Example 1, except that 5-fluoro-4-(trifluoromethyl)-1H-benzo[d]imidazole was used instead of 1H-benzo[d]imidazole, thereby obtaining the title compound (20 mg, yield: 67%).

¹H-NMR (500 MHz, DMSO-d₆): δ 8.27 (s, 1H), 7.81 (m, 1H), 7.32 (m, 1H), 5.41 (d, 2H), 4.83 (d, 1H), 2.94 (m, 1H), 2.91 (m, 1H), 2.80 (d, 1H), 2.67 (m, 1H), 2.42 (m, 1H), 2.36 (m, 1H), 1.90 (d, 1H), 1.57 (d, 1H), 1.35 (m, 1H), 1.23 (m, 1H).

Example 18: Preparation of 1-(5-bromo-4-(trifluoromethyl)-1H-benzo[d]imidazol-1-yl)-3-((2R,3S)-3-hydroxypiperidin-2-yl)propan-2-one

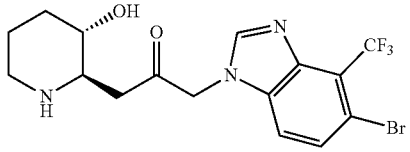

The reaction was carried out in the same manner as in Step 1-1 and Step 1-2 of Example 1, except that 5-bromo-4-(trifluoromethyl)-1H-benzo[d]imidazole was used instead of 1H-benzo[d]imidazole, thereby obtaining the title compound (20 mg, yield: 67%).

¹H-NMR (500 MHz, DMSO-d₆): δ 8.26 (s, 1H), 7.72 (d, 1H), 7.65 (d, 1H), 5.42 (d, 2H), 4.85 (s, 1H), 3.02 (m, 1H), 2.93 (d, 1H), 2.83 (d, 1H), 2.68 (m, 1H), 2.42 (m, 2H), 1.91 (m, 1H), 1.58 (m, 1H), 1.36 (m, 1H), 1.24 (m, 1H).

Example 19: Preparation of 1-(4-bromo-5-methyl-1H-benzo[d]imidazol-1-yl)-3-((2R,3S)-3-hydroxypiperidin-2-yl)propan-2-one

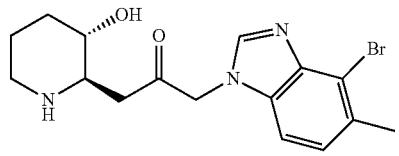 [SMILES: Cc1ccc2c(ncn2CC(=O)C[C@H]2NCCC[C@@H]2O)c1Br]

The reaction was carried out in the same manner as in Step 1-1 and Step 1-2 of Example 1, except that 5-methyl-4-bromo-1H-benzo[d]imidazole was used instead of 1H-benzo[d]imidazole, thereby obtaining the title compound (18 mg, yield: 63%).

¹H-NMR (500 MHz, DMSO-d₆): δ 8.07 (s, 1H), 7.36 (d, 1H), 7.18 (d, 1H), 5.32 (d, 2H), 4.81 (m, 1H), 2.99 (m, 1H), 2.90 (d, 1H), 2.80 (d, 1H), 2.66 (m, 1H), 2.42 (s, 3H), 2.34 (m, 2H), 1.89 (d, 1H), 1.57 (d, 1H), 1.33 (m, 1H), 1.25 (m, 1H).

Example 20: Preparation of 1-(5-bromo-4-fluoro-1H-benzo[d]imidazol-1-yl)-3-((2R,3S)-3-hydroxypiperidin-2-yl)propan-2-one

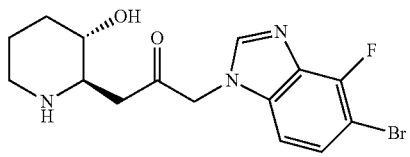 [SMILES: O=C(C[C@H]1NCCC[C@@H]1O)Cn1cnc2c(F)c(Br)ccc21]

The reaction was carried out in the same manner as in Step 1-1 and Step 1-2 of Example 1, except that 5-bromo-4-fluoro-1H-benzo[d]imidazole was used instead of 1H-benzo[d]imidazole, thereby obtaining the title compound (15 mg, yield: 61%).

$^1$H-NMR (500 MHz, DMSO-d$_6$): δ 8.14 (s, 1H), 7.45 (m, 1H), 7.32 (d, 1H), 5.37 (m, 2H), 4.82 (m, 1H), 2.99 (m, 1H), 2.90 (d, 1H), 2.80 (m, 1H), 2.65 (m, 1H), 2.37 (m, 2H), 1.89 (m, 1H), 1.59 (m, 1H), 1.34 (m, 1H), 1.22 (m, 1H).

Example 21: Preparation of 1-(4-chloro-5-fluoro-1H-benzo[d]imidazol-1-yl)-3-((2R,3S)-3-hydroxypiperidin-2-yl)propan-2-one

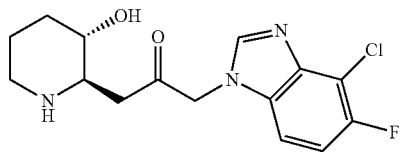 [SMILES: O=C(C[C@H]1NCCC[C@@H]1O)Cn1cnc2c(Cl)c(F)ccc21]

The reaction was carried out in the same manner as in Step 1-1 and Step 1-2 of Example 1, except that 4-chloro-5-fluoro-1H-benzo[d]imidazole was used instead of 1H-benzo[d]imidazole, thereby obtaining the title compound (22 mg, yield: 75%).

$^1$H-NMR (500 MHz, DMSO-d$_6$): δ 8.14 (d, 1H), 7.81 (dd, 1H), 7.60 (dd, 1H), 5.33-5.29 (m, 2H), 4.81 (t, 1H), 3.30-2.99 (m, 1H), 2.93-2.88 (m, 1H), 2.80 (s, 1H), 2.66-2.62 (m, 1H), 2.43-2.34 (m, 1H), 1.88 (d, 1H), 1.56 (d, 1H), 1.26-1.21 (m, 1H).

Example 22: Preparation of 1-(5-bromo-4-chloro-1H-benzo[d]imidazol-1-yl)-3-((2R,3S)-3-hydroxypiperidin-2-yl)propan-2-one

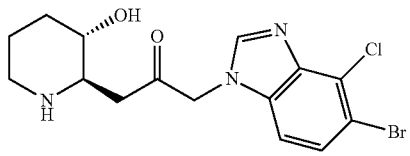 [SMILES: O=C(C[C@H]1NCCC[C@@H]1O)Cn1cnc2c(Cl)c(Br)ccc21]

The reaction was carried out in the same manner as in Step 1-1 and Step 1-2 of Example 1, except that 5-bromo-4-chloro-1H-benzo[d]imidazole was used instead of 1H-benzo[d]imidazole, thereby obtaining the title compound (22 mg, yield: 75%).

$^1$H-NMR (500 MHz, DMSO-d$_6$): δ 8.17 (s, 1H), 7.56 (d, 1H), 7.45 (d, 1H), 5.37 (dd, 2H), 4.87 (d, 1H), 3.03 (m, 1H), 2.94 (dd, 1H), 2.84 (d, 1H), 2.70 (m, 1H), 2.42 (m, 2H), 1.91 (m, 1H), 1.60 (d, 1H), 1.34 (m, 1H), 1.25 (m, 1H).

Example 23: Preparation of 1-(6-bromo-4-methyl-1H-benzo[d]imidazol-1-yl)-3-((2R,3S)-3-hydroxypiperidin-2-yl)propan-2-one

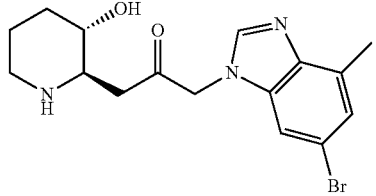 [SMILES: Cc1cc(Br)cc2c1ncn2CC(=O)C[C@H]1NCCC[C@@H]1O]

The reaction was carried out in the same manner as in Step 1-1 and Step 1-2 of Example 1, except that 6-bromo-4-methyl-1H-benzo[d]imidazole was used instead of 1H-benzo[d]imidazole, thereby obtaining the title compound (10 mg, yield: 40%).

$^1$H-NMR (500 MHz, DMSO-d$_6$): δ 8.14 (s, 1H), 7.83 (d, 1H), 7.62 (d, 1H), 5.30 (m, 2H), 4.84 (s, 1H), 3.02 (m, 1H), 2.94 (m, 1H), 2.82 (m, 1H), 2.68 (m, 1H), 2.43 (m, 1H), 2.39 (m, 1H), 1.91 (m, 1H), 1.59 (m, 1H), 1.36 (m, 1H), 1.26 (m, 1H).

Example 24: Preparation of 1-(6-chloro-4-methyl-1H-benzo[d]imidazol-1-yl)-3-((2R,3S)-3-hydroxypiperidin-2-yl)propan-2-one

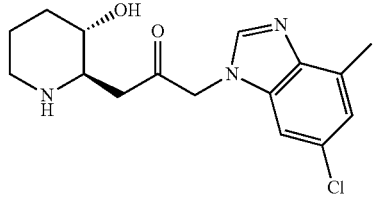 [SMILES: Cc1cc(Cl)cc2c1ncn2CC(=O)C[C@H]1NCCC[C@@H]1O]

The reaction was carried out in the same manner as in Step 1-1 and Step 1-2 of Example 1, except that 6-chloro-4-methyl-1H-benzo[d]imidazole was used instead of 1H-benzo[d]imidazole, thereby obtaining the title compound (10 mg, yield: 36%).

$^1$H-NMR (500 MHz, DMSO-d$_6$): δ 8.16 (s, 1H), 7.87 (d, 1H), 7.70 (d, 1H), 5.30 (m, 2H), 4.84 (s, 1H), 3.02 (m, 1H), 2.94 (m, 1H), 2.82 (m, 1H), 2.68 (m, 1H), 2.43 (m, 1H), 2.39 (m, 1H), 1.91 (m, 1H), 1.59 (m, 1H), 1.36 (m, 1H), 1.26 (m, 1H).

Example 25: Preparation of 1-(5,6-dichloro-1H-benzo[d]imidazol-1-yl)-3-((2R,3S)-3-hydroxypiperidin-2-yl)propan-2-one

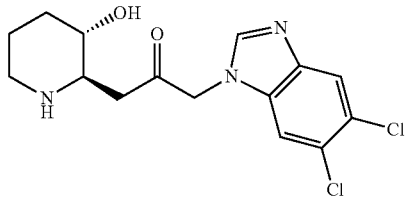 [SMILES: O=C(C[C@H]1NCCC[C@@H]1O)Cn1cnc2cc(Cl)c(Cl)cc21]

The reaction was carried out in the same manner as in Step 1-1 and Step 1-2 of Example 1, except that 5,6-dichloro-1H-benzo[d]imidazole was used instead of 1H-benzo[d]imidazole, thereby obtaining the title compound (20 mg, yield: 70%).

$^1$H-NMR (500 MHz, DMSO-$d_6$): δ 8.16 (s, 1H), 7.93 (d, 2H), 5.34 (dd, 2H), 4.82 (d, 1H), 3.00 (m, 1H), 2.94 (dd, 1H), 2.83 (d, 1H), 2.66 (m, 1H), 2.39 (m, 2H), 1.91 (d, 1H), 1.58 (d, 1H), 1.33 (m, 1H), 1.22 (m, 1H).

Example 26: Preparation of 1-(6-bromo-5-fluoro-1H-benzo[d]imidazol-1-yl)-3-((2R,3S)-3-hydroxypiperidin-2-yl)propan-2-one

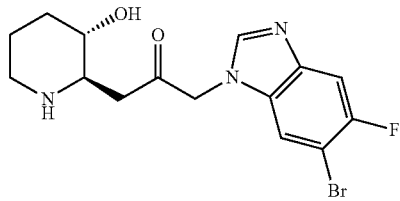 [SMILES: O=C(C[C@H]1NCCC[C@@H]1O)Cn1cnc2cc(F)c(Br)cc21]

The reaction was carried out in the same manner as in Step 1-1 and Step 1-2 of Example 1, except that 6-bromo-5-fluoro-1H-benzo[d]imidazole was used instead of 1H-benzo[d]imidazole, thereby obtaining the title compound (14 mg, yield: 65%).

$^1$H-NMR (500 MHz, DMSO-$d_6$): δ 8.13 (s, 1H), 7.83 (d, 1H), 7.64 (d, 1H), 5.30 (m, 2H), 4.82 (s, 1H), 3.00 (m, 1H), 2.91 (dd, 1H), 2.81 (d, 1H), 2.65 (m, 1H), 2.41 (m, 1H), 2.35 (m, 1H), 2.08 (s, 1H), 1.89 (d, 1H), 1.59 (m, 1H), 1.39-1.21 (m, 2H).

Example 27: Preparation of 1-(5,6-dibromo-1H-benzo[d]imidazol-1-yl)-3-((2R,3S)-3-hydroxypiperidin-2-yl)propan-2-one

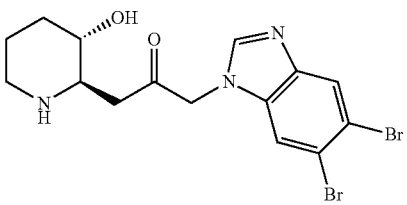 [SMILES: O=C(C[C@H]1NCCC[C@@H]1O)Cn1cnc2cc(Br)c(Br)cc21]

The reaction was carried out in the same manner as in Step 1-1 and Step 1-2 of Example 1, except that 5,6-dibromo-1H-benzo[d]imidazole was used instead of 1H-benzo[d]imidazole, thereby obtaining the title compound (22 mg, yield: 75%).

$^1$H-NMR (500 MHz, DMSO-$d_6$): δ 8.13 (s, 1H), 8.06 (d, 2H), 5.34 (dd, 2H), 4.82 (d, 1H), 3.00 (m, 1H), 2.94 (dd, 1H), 2.84 (d, 1H), 2.66 (m, 1H), 2.39 (m, 2H), 1.91 (d, 1H), 1.60 (d, 1H), 1.33 (m, 1H), 1.22 (m, 1H).

Example 28: Preparation of 1-(6-chloro-7-methyl-1H-benzo[d]imidazol-1-yl)-3-((2R,3S)-3-hydroxypiperidin-2-yl)propan-2-one

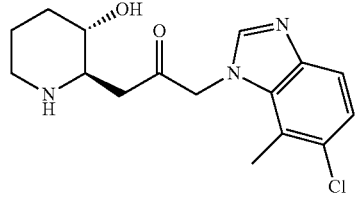 [SMILES: Cc1c(Cl)ccc2ncn(CC(=O)C[C@H]3NCCC[C@@H]3O)c12]

The reaction was carried out in the same manner as in Step 4-1 to Step 4-9 of Example 4, except that 1-chloro-3-fluoro-2-methyl-4-nitrobenzene was used instead of 4-bromo-1-fluoro-2-nitrobenzene in Step 4-5 of Example 4, thereby obtaining the title compound (40 mg, yield: 70%).

$^1$H-NMR (500 MHz, DMSO-$d_6$): δ 8.00 (s, 1H), 7.49 (d, 1H), 7.23 (d, 1H), 5.52 (dd, 2H), 4.78 (d, 1H), 2.97 (m, 2H), 2.80 (d, 1H), 2.65 (m, 1H), 2.44 (m, 1H), 2.34 (t, 1H), 1.89 (m, 1H), 1.58 (d, 1H), 1.33 (m, 1H), 1.22 (m, 1H).

Example 29: Preparation of 1-(5-bromo-1H-imidazo[4,5-b]pyridin-1-yl)-3-((2R,3S)-3-hydroxypiperidin-2-yl)propan-2-one

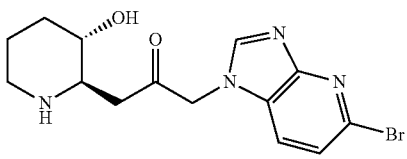 [SMILES: O=C(C[C@H]1NCCC[C@@H]1O)Cn1cnc2nc(Br)ccc21]

The reaction was carried out in the same manner as in Step 1-1 and Step 1-2 of Example 1, except that 5-bromo-1H-imidazo[4,5-b]pyridine was used instead of 1H-benzo[d]imidazole, thereby obtaining the title compound (20 mg, yield: 68%).

$^1$H-NMR (500 MHz, DMSO-$d_6$): δ 8.31 (s, 1H), 8.08 (d, 1H), 7.48 (d, 1H), 5.32 (dd, 2H), 4.80 (d, 1H), 3.00 (m, 2H), 2.81 (d, 1H), 2.67 (m, 1H), 2.37 (m, 1H), 1.90 (d, 1H), 1.58 (d, 1H), 1.34 (m, 1H), 1.23 (m, 1H).

Example 30: Preparation of 1-((2R,3S)-3-hydroxypiperidin-2-yl)-3-(5-(trifluoromethyl)-1H-imidazo[4,5-b]pyridin-1-yl)propan-2-one

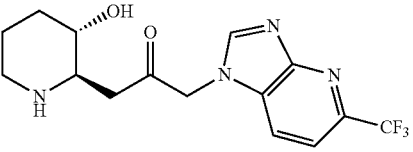 [SMILES: O=C(C[C@H]1NCCC[C@@H]1O)Cn1cnc2nc(C(F)(F)F)ccc21]

The reaction was carried out in the same manner as in Step 1-1 of Example 1, except that 5-(trifluoromethyl)-3H-imidazo[4,5-b]pyridine was used instead of 1H-benzo[d]imidazole, and then separated by column chromatography (hexane:ethyl acetate=1:4), thereby obtaining an intermediate (38 mg, yield: 30%). Subsequently, the reaction was carried out in the same manner as in Step 1-2 of Example 1, thereby obtaining the title compound (12 mg, yield: 56%).

$^{1}$H-NMR (500 MHz, DMSO-d$_{6}$): δ 8.53 (s, 1H), 8.16 (d, 1H), 7.76 (d, 1H), 5.44 (d, 2H), 4.82 (s, 1H), 2.94 (m, 1H), 2.91 (m, 1H), 2.79 (d, 1H), 2.66 (m, 1H), 2.45 (m, 1H), 2.36 (m, 1H), 1.89 (d, 1H), 1.56 (d, 1H), 1.34 (m, 1H), 1.23 (m, 1H).

Example 31: Preparation of 1-(6-bromo-1H-imidazo[4,5-b]pyridin-1-yl)-3-((2R,3S)-3-hydroxypiperidin-2-yl)propan-2-one

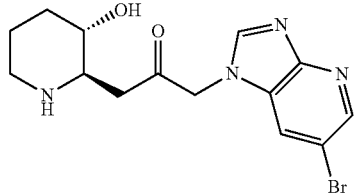 [SMILES: O=C(C[C@H]1NCCC[C@@H]1O)Cn1cnc2ncc(Br)cc21]

The reaction was carried out in the same manner as in Step 1-1 and Step 1-2 of Example 1, except that 6-bromo-1H-imidazo[4,5-b]pyridine was used instead of 1H-benzo[d]imidazole, thereby obtaining the title compound (22 mg, yield: 75%).

$^{1}$H-NMR (500 MHz, DMSO-d$_{6}$): δ 8.48 (d, 1H), 8.33 (s, 1h), 8.29 (s, 1H), 5.37 (dd, 2H), 4.86 (d, 1H), 3.03 (m, 1H), 2.96 (dd, 1H), 2.84 (d, 1H), 2.70 (m, 1H), 2.43 (m, 1H), 1.90 (m, 1H), 1.60 (d, 1H), 1.36 (m, 1H), 1.26 (m, 1H).

Example 32: Preparation of 1-(6-chloro-1H-imidazo[4,5-c]pyridin-1-yl)-3-((2R,3S)-3-hydroxypiperidin-2-yl)propan-2-one

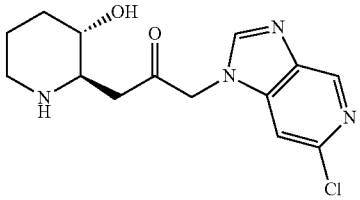 [SMILES: O=C(C[C@H]1NCCC[C@@H]1O)Cn1cnc2cnc(Cl)cc21]

The reaction was carried out in the same manner as in Step 1-1 and Step 1-2 of Example 1, except that 6-chloro-1H-imidazo[4,5-b]pyridine was used instead of 1H-benzo[d]imidazole, thereby obtaining the title compound (20 mg, yield: 72%).

$^{1}$H-NMR (500 MHz, DMSO-d$_{6}$): δ 8.76 (s, 1H), 8.24 (s, 1H), 7.72 (s, 1H), 5.39 (dd, 2H), 5.10 (brs 1H), 3.18 (m, 1H), 3.01 (m, 1H), 2.92 (m, 2H), 2.55 (m, 2H), 1.90 (m, 1H), 1.67 (d, 1H), 1.43 (m, 1H), 1.32 (m, 1H).

Example 33: Preparation of 1-(7-bromo-1H-imidazo[4,5-c]pyridin-1-yl)-3-((2R,3S)-3-hydroxypiperidin-2-yl)propan-2-one

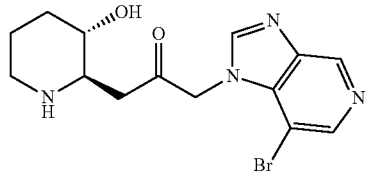 [SMILES: O=C(C[C@H]1NCCC[C@@H]1O)Cn1cnc2cncc(Br)c21]

The reaction was carried out in the same manner as in Step 1-1 and Step 1-2 of Example 1, except that 7-bromo-1H-imidazo[4,5-b]pyridine was used instead of 1H-benzo[d]imidazole, thereby obtaining the title compound (15 mg, yield: 51%).

$^{1}$H-NMR (500 MHz, CDCl$_{3}$-d$_{6}$): δ 8.88 (s, 1H), 8.64 (s, 1H), 8.03 (s, 1H), 5.24 (m, 1H), 5.11 (m, 1H), 4.41 (d, 1H), 3.27 (m, 1H), 2.99-3.08 (m, 2H), 2.59 (m, 1H), 2.09 (m, 1H), 1.75 (m, 1H).

Example 34: Preparation of 1-((2R,3S)-3-hydroxypiperidin-2-yl)-3-(3H-imidazo[4,5-b]pyridin-3-yl)propan-2-one

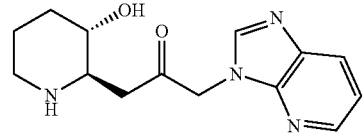 [SMILES: O=C(C[C@H]1NCCC[C@@H]1O)Cn1cnc2cccnc21]

The reaction was carried out in the same manner as in Step 1-1 and Step 1-2 of Example 1, except that 3H-imidazo[4,5-b]pyridine was used instead of 1H-benzo[d]imidazole, thereby obtaining the title compound (17 mg, yield: 65%).

$^{1}$H-NMR (500 MHz, CDCl$_{3}$-d$_{6}$): δ 8.35 (d, 1H), 8.09 (dd, 1H), 8.06 (s, 1H), 5.19 (s, 2H), 3.28 (m, 1H), 3.09 (dd, 1H), 2.97 (m, 1H), 2.88 (m, 1H), 2.60 (m, 2H), 2.08 (m, 1H), 1.73 (m, 1H), 1.51 (m, 1H), 1.34 (m, 1H).

Example 35: Preparation of 1-(5-bromo-3H-imidazo[4,5-b]pyridin-3-yl)-3-((2R,3S)-3-hydroxypiperidin-2-yl)propan-2-one

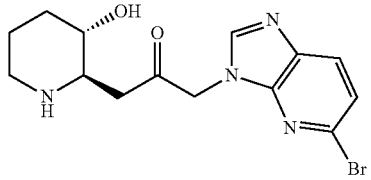 [SMILES: O=C(C[C@H]1NCCC[C@@H]1O)Cn1cnc2ccc(Br)nc21]

The reaction was carried out in the same manner as in Step 1-1 and Step 1-2 of Example 1, except that 5-bromo-3H-imidazo[4,5-b]pyridine was used instead of 1H-benzo[d]imidazole, thereby obtaining the title compound (19 mg, yield: 65%).

$^{1}$H-NMR (500 MHz, DMSO-d$_{6}$): δ 8.33 (s, 1H), 7.91 (d, 1H), 7.47 (d, 1H), 5.39 (dd, 2H), 4.85 (d, 1H), 3.01 (m, 1H), 2.92 (dd, 1H), 2.66 (m, 1H), 2.37 (m, 2H), 1.90 (m, 1H), 1.58 (d, 1H), 1.36 (m, 1H), 1.24 (m, 1H).

Example 36: Preparation of 1-((2R,3S)-3-hydroxypiperidin-2-yl)-3-(5-(trifluoromethyl)-3H-imidazo[4,5-b]pyridin-3-yl)propan-2-one

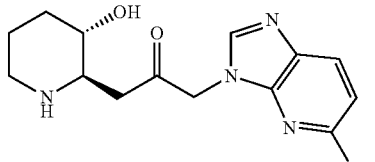

The reaction was carried out in the same manner as in Step 1-1 of Example 1, except that 5-(trifluoromethyl)-3H-imidazo[4,5-b]pyridine was used instead of 1H-benzo[d]imidazole, and then separated by column chromatography (hexane:ethyl acetate=1:4), thereby obtaining an intermediate (59 mg, yield: 47%). Subsequently, the reaction was carried out in the same manner as in Step 1-2 of Example 1, thereby obtaining the title compound (21 mg, yield: 63%).

$^1$H-NMR (500 MHz, DMSO-$d_6$): δ 8.55 (s, 1H), 8.36 (d, 1H), 7.78 (d, 1H), 5.39 (d, 2H), 4.77 (d, 1H), 3.00 (m, 2H), 2.79 (d, 1H), 2.66 (m, 1H), 2.36 (m, 1H), 2.02 (s, 1H), 1.89 (d, 1H), 1.56 (d, 1H), 1.35 (m, 1H), 1.22 (m, 1H).

Example 37: Preparation of 1-(6-bromo-3H-imidazo[4,5-b]pyridin-3-yl)-3-((2R,3S)-3-hydroxypiperidin-2-yl)propan-2-one

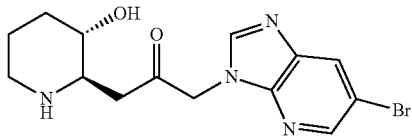 [SMILES: O=C(C[C@H]1NCCC[C@@H]1O)Cn1cnc2cc(Br)cnc21]

The reaction was carried out in the same manner as in Step 1-1 and Step 1-2 of Example 1, except that 6-bromo-3H-imidazo[4,5-b]pyridine was used instead of 1H-benzo[d]imidazole, thereby obtaining the title compound (21 mg, yield: 71%).

$^1$H-NMR (500 MHz, DMSO-$d_6$): δ 8.43 (d, 1H), 8.40 (d, 1H), 8.35 (s, 1H), 5.32 (dd, 2H), 4.77 (d, 1H), 2.97 (m, 2H), 2.80 (d, 1H), 2.65 (m, 1H), 2.45 (m, 1H), 2.36 (t, 1H), 1.90 (m, 1H), 1.58 (d, 1H), 1.33 (m, 1H), 1.26 (m, 1H).

Example 38: Preparation of 3-(3-((2R,3S)-3-hydroxypiperidin-2-yl)-2-oxopropyl)-3H-imidazo[4,5-b]pyridine-6-carbonitrile

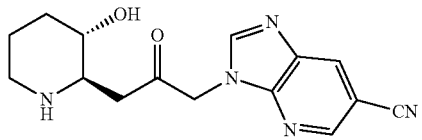 [SMILES: N#Cc1cnc2c(c1)ncn2CC(=O)C[C@H]1NCCC[C@@H]1O]

The reaction was carried out in the same manner as in Step 1-1 and Step 1-2 of Example 1, except that 3H-imidazo[4,5-b]pyridin-carbonitrile was used instead of 1H-benzo[d]imidazole, thereby obtaining the title compound (11 mg, yield: 48%).

$^1$H-NMR (500 MHz, DMSO-$d_6$): δ 8.72 (d, 2H), 8.52 (s, 1H), 5.38-5.5.30 (m, 2H), 4.82 (d, 1H), 3.33 (s, 1H), 2.96 (d, 1H), 2.84 (d, 2H), 2.81 (s, 2H), 2.06 (s, 1H), 1.90 (d, 1H), 1.58 (d, 1H), 1.38-1.26 (m, 1H).

Example 39: Preparation of 1-(6-chloro-7-methyl-3H-imidazo[4,5-b]pyridin-3-yl)-3-((2R,3S)-3-hydroxypiperidin-2-yl)propan-2-one

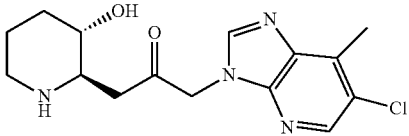 [SMILES: Cc1c(Cl)cnc2c1ncn2CC(=O)C[C@H]1NCCC[C@@H]1O]

The reaction was carried out in the same manner as in Step 1-1 and Step 1-2 of Example 1, except that 6-chloro-7-methyl-3H-imidazo[4,5-b]pyridine was used instead of 1H-benzo[d]imidazole, thereby obtaining the title compound (25 mg, yield: 77%).

$^1$H-NMR (500 MHz, DMSO-$d_6$): δ 8.31 (m, 2H), 5.29 (d, 2H), 4.75 (d, 1H), 2.96 (m, 2H), 2.78 (d, 1H), 2.62 (s, 3H), 2.42 (m, 1H), 2.32 (m, 1H), 1.99 (m, 1H), 1.88 (d, 1H), 1.57 (d, 1H), 1.37 (m, 1H), 1.28 (m, 1H).

Example 40: Preparation of 1-(6-bromo-7-methyl-3H-imidazo[4,5-b]pyridin-3-yl)-3-((2R,3S)-3-hydroxypiperidin-2-yl)propan-2-one

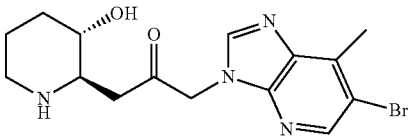 [SMILES: Cc1c(Br)cnc2c1ncn2CC(=O)C[C@H]1NCCC[C@@H]1O]

The reaction was carried out in the same manner as in Step 1-1 and Step 1-2 of Example 1, except that 6-bromo-7-methyl-3H-imidazo[4,5-b]pyridine was used instead of 1H-benzo[d]imidazole, thereby obtaining the title compound (27 mg, yield: 75%).

$^1$H-NMR (500 MHz, DMSO-$d_6$): δ 8.28 (m, 2H), 5.27 (d, 2H), 4.75 (d, 1H), 2.94 (m, 2H), 2.77 (d, 1H), 2.43 (m, 1H), 2.33 (m, 1H), 1.98 (m, 1H), 1.88 (m, 1H), 1.53 (m, 1H), 1.31 (m, 1H), 1.25 (m, 1H).

Example 41: Preparation of 1-(5,7-dichloro-3H-imidazo[4,5-b]pyridin-3-yl)-3-((2R,3S)-3-hydroxypiperidin-2-yl)propan-2-one

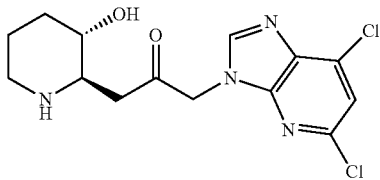 [SMILES: O=C(C[C@H]1NCCC[C@@H]1O)Cn1cnc2c(Cl)cc(Cl)nc21]

The reaction was carried out in the same manner as in Step 1-1 and Step 1-2 of Example 1, except that 5,7-dichloro-3H-imidazo[4,5-b]pyridine was used instead of 1H-benzo[d]imidazole, thereby obtaining the title compound (20 mg, yield: 70%).

$^1$H-NMR (500 MHz, DMSO-d$_6$): δ 8.42 (s, 1H), 7.64 (s, 1H), 5.34 (dd, 2H), 4.77 (d, 1H), 2.99 (m, 2H), 2.81 (d, 1H), 2.65 (m, 1H), 2.46 (m, 1H), 2.36 (m, 1H), 1.90 (m, 1H), 1.58 (d, 1H), 1.33 (m, 1H), 1.23 (m, 1H).

Example 42: Preparation of 1-(6-bromo-7-chloro-3H-imidazo[4,5-b]pyridin-3-yl)-3-((2R,3S)-3-hydroxypiperidin-2-yl)propan-2-one

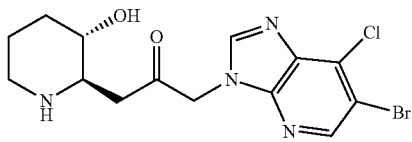 [SMILES: O=C(C[C@H]1NCCC[C@@H]1O)Cn1cnc2c(Cl)c(Br)cnc21]

The reaction was carried out in the same manner as in Step 1-1 and Step 1-2 of Example 1, except that 6-bromo-7-chloro-3H-imidazo[4,5-b]pyridine was used instead of 1H-benzo[d]imidazole, thereby obtaining the title compound (22 mg, yield: 70%).

$^1$H-NMR (500 MHz, DMSO-d$_6$): δ 8.57 (s, 1H), 8.42 (s, 1H), 5.34 (d, 2H), 4.75 (d, 1H), 2.96 (m, 2H), 2.77 (d, 1H), 2.63 (m, 1H), 2.43 (m, 1H), 2.35 (m, 1H), 1.88 (d, 1H), 1.55 (d, 1H), 1.33 (m, 1H), 1.24 (m, 1H).

Example 43: Preparation of 3-(3-((2R,3S)-3-hydroxypiperidin-2-yl)-2-oxopropyl)-3H-imidazo[4,5-c]pyridine-6-carboxylic acid hydrochloride salt

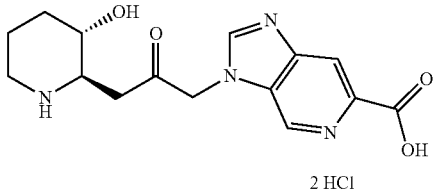 [SMILES: O=C(C[C@H]1NCCC[C@@H]1O)Cn1cnc2cc(C(=O)O)ncc21]

(Step 43-1) Preparation of methyl 3-(3-((2R,3S)-1-((benzyloxy)carbonyl)-3-(tert-butyldimethylsilyloxy)piperidin-2-yl)-2-oxopropyl)-3H-imidazo[4,5-c]pyridin-6-carboxylate Methyl 3H-imidazo[4,5-c]pyridin-6-carboxylate (44 mg, 0.25 mmol) was dissolved in N,N-dimethylformamide (2 mL) to which potassium carbonate (69 mg, 0.50 mmol) was added and then stirred at room temperature for 10 minutes. Then, benzyl (2R,3S)-2-(3-bromo-2-oxopropyl)-3-(tert-butyldimethylsilyloxy)piperidin-1-carboxylate (120 mg, 0.25 mmol) was added thereto and stirred at room temperature for 3 hours. When the reaction is completed, the solvent was removed, and the resulting mixture was diluted with ethyl acetate and then washed with saturated sodium chloride solution. The organic layer was collected, dried over magnesium sulfate, filtered and concentrated under reduced pressure, and then purified by column chromatography (dichloromethane:methanol=10:1), thereby obtaining the title compound (110 mg, yield: 79%).

(Step 43-2) Preparation of 3-(3-((2R,3S)-3-hydroxypiperidin-2-yl)-2-oxo-propyl)-3H-imidazo[4,5-c]pyridin-6-carboxylic acid hydrochloride Methyl 3-(3-((2R,3S)-1-((benzyloxy)carbonyl)-3-(tert-butyldimethylsilyloxy)piperidin-2-yl)-2-oxopropyl)-3H-imidazo[4,5-c]pyridin-6-carboxylate (88 mg, 0.15 mmol) obtained from Step 43-1 was dissolved in 6N hydrochloric acid solution (2 mL) and then stirred under reflux for 1 hour. When the reaction was completed, the reaction solution was cooled to room temperature and the solvent was removed. The resulting product was recrystallized in acetone and washed with diethyl ether, thereby obtaining the title compound (48 mg, yield: 53%).

$^1$H-NMR (500 MHz, DMSO-d$_6$): δ 8.76-8.67 (d, 2H), 7.93 (s, 1H), 5.71 (d, 2H), 3.28 (s, 1H), 3.27-3.14 (m, 2H), 2.99-2.94 (m, 1H), 2.81 (d, 1H), 2.71 (s, 1H), 2.19 (s, 1H), 1.93-1.89 (s, 1H), 1.76-1.68 (m, 2H), 1.46-1.40 (m, 1H).

Example 44: Preparation of 1-(6-chloro-9H-purin-9-yl)-3-((2R,3S)-3-hydroxypiperidin-2-yl)propan-2-one hydrochloride salt

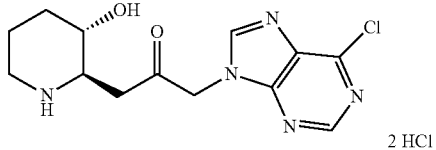 [SMILES: O=C(C[C@H]1NCCC[C@@H]1O)Cn1cnc2c(Cl)ncnc21]

The reaction was carried out in the same manner as in Step 43-1 and Step 43-2 of Example 43, except that 6-chloro-9H-purine was used instead of methyl 3H-imidazo[4,5-c]pyridin-6-carboxylate, thereby obtaining the title compound (19 mg, yield: 36%).

$^1$H-NMR (500 MHz, DMSO-d$_6$): δ 8.60 (d, 1H), 8.26 (s, 1H), 5.06 (s, 2H), 3.53 (s, 1H), 3.29-3.16 (m, 3H), 2.99-2.92 (m, 1H), 2.85-2.73 (m, 1H), 2.06 (s, 1H), 1.90 (d, 1H), 1.88 (d, 1H), 1.75 (d, 1H), 1.63 (d, 1H).

Example 45: Preparation of 1-((2R,3S)-3-hydroxypiperidin-2-yl)-3-(4,5,6,7-tetrahydro-1H-benzo[d]imidazol-1-yl)propan-2-one

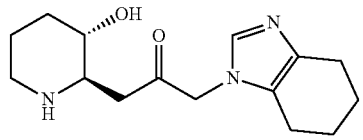 [SMILES: O=C(C[C@H]1NCCC[C@@H]1O)Cn1cnc2c1CCCC2]

The reaction was carried out in the same manner as in Step 1-1 and Step 1-2 of Example 1, except that 4,5,6,7-tetrahydro-1H-benzo[d]imidazole was used instead of 1H-benzo[d]imidazole, thereby obtaining the title compound (17 mg, yield: 67%).

$^1$H-NMR (500 MHz, DMSO-d$_6$): δ 7.33 (s, 1H), 5.15 (d, 2H), 4.75 (d, 1H), 2.97 (m, 2H), 2.75 (d, 1H), 2.70 (m, 2H), 2.66 (m, 2H), 2.40 (m, 1H), 2.37 (m, 1H), 1.99 (m, 1H), 1.91 (m, 2H), 1.87 (m, 1H), 1.85 (m, 2H), 1.55 (m, 1H), 1.33 (m, 1H), 1.21 (m, 1H).

Example 46: Preparation of 1-(5,6-dichloro-2-methyl-1H-benzo[d]imidazol-1-yl)-3-((2R,3S)-3-hydroxypiperidin-2-yl)propan-2-one

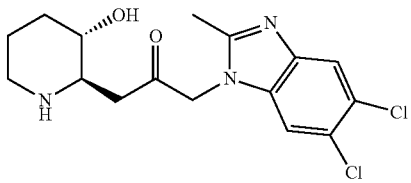 [SMILES: Cc1nc2cc(Cl)c(Cl)cc2n1CC(=O)C[C@H]1NCCC[C@@H]1O]

The reaction was carried out in the same manner as in Step 1-1 and Step 1-2 of Example 1, except that 5,6-dichloro-2-methyl-1H-benzo[d]imidazole was used instead of 1H-benzo[d]imidazole, thereby obtaining the title compound (82 mg, yield: 87%).

$^1$H-NMR (500 MHz, DMSO-d$_6$): δ 7.82 (s, 1H), 7.77 (s, 1H), 5.30 (dd, 2H), 4.84 (d, 1H), 3.00 (m, 1H), 2.93 (dd, 1H), 2.82 (d, 1H), 2.67 (m, 1H), 2.43 (m, 1H), 2.38 (s, 3H), 1.90 (m, 1H), 1.58 (d, 1H), 1.34 (m, 1H), 1.23 (m, 1H).

Example 47: Preparation of 1-(4,5-difluoro-2-methyl-1H-benzo[d]imidazol-1-yl)-3-((2R,3S)-3-hydroxypiperidin-2-yl)propan-2-one

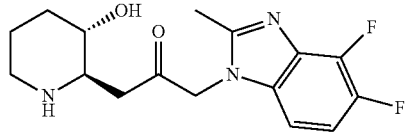 [SMILES: Cc1nc2c(F)c(F)ccc2n1CC(=O)C[C@H]1NCCC[C@@H]1O]

The reaction was carried out in the same manner as in Step 1-1 and Step 1-2 of Example 1, except that 4,5-difluoro-2-methyl-1H-benzo[d]imidazole was used instead of 1H-benzo[d]imidazole, thereby obtaining the title compound (10 mg, yield: 40%).

$^1$H-NMR (500 MHz, DMSO-d$_6$): δ 7.15-7.36 (m, 2H), 5.33 (m, 2H), 4.84 (d, 1H), 3.02 (m, 1H), 2.97 (dd, 1H), 2.82 (m, 1H), 2.69 (m, 1H), 2.43 (m, 5H), 1.9 (m, 1H), 1.59 (m, 1H), 1.35 (m, 1H), 1.24 (m, 1H).

Example 48: Preparation of 1-(5,6-dichloro-2-ethyl-1H-benzo[d]imidazol-1-yl)-3-((2R,3S)-3-hydroxypiperidin-2-yl)propan-2-one

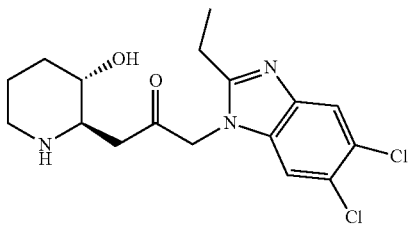 [SMILES: CCc1nc2cc(Cl)c(Cl)cc2n1CC(=O)C[C@H]1NCCC[C@@H]1O]

The reaction was carried out in the same manner as in Step 1-1 and Step 1-2 of Example 1, except that 5,6-dichloro-2-ethyl-1H-benzo[d]imidazole was used instead of 1H-benzo[d]imidazole, thereby obtaining the title compound (28 mg, yield: 83%).

$^1$H-NMR (500 MHz, DMSO-d$_6$): δ 7.82 (d, 2H), 5.30 (dd, 2H), 4.82 (d, 1H), 3.00 (m, 1H), 2.94 (dd, 1H), 2.70 (q, 2H), 2.66 (m, 1H), 2.41 (dd, 1H), 2.37 (m, 1H), 1.89 (d, 1H), 1.60 (d, 1H), 1.34 (m, 1H), 1.23 (m, 4H).

Example 49: Preparation of 1-((2R,3S)-3-hydroxypiperidin-2-yl)-3-(2-methyl-1H-imidazo[4,5-b]pyridin-1-yl)propan-2-one

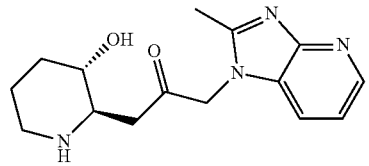 [SMILES: Cc1nc2ncccc2n1CC(=O)C[C@H]1NCCC[C@@H]1O]

The reaction was carried out in the same manner as in Step 1-1 and Step 1-2 of Example 1, except that 2-methyl-1H-imidazo[4,5-b]pyridine was used instead of 1H-benzo[d]imidazole, thereby obtaining the title compound (12 mg, yield: 66%).

$^1$H-NMR (500 MHz, DMSO-d$_6$): δ 8.20 (d, 1H), 7.93 (d, 1H), 7.21 (m, 1H), 5.30 (m, 2H), 4.78 (m, 1H), 2.98 (m, 1H), 2.80 (m, 1H), 2.66 (m, 1H), 2.39 (m, 2H), 2.01 (m, 1H), 1.90 (m, 1H), 1.58 (d, 1H), 1.34 (m, 1H), 1.22 (m, 1H).

Example 50: Preparation of 1-(5,6-dichloro-2-(trifluoromethyl)-1H-benzo[d]imidazol-1-yl)-3-((2R,3S)-3-hydroxypiperidin-2-yl)propan-2-one

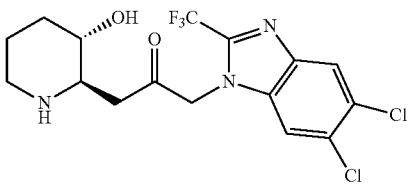 [SMILES: O=C(C[C@H]1NCCC[C@@H]1O)Cn1c(C(F)(F)F)nc2cc(Cl)c(Cl)cc21]

The reaction was carried out in the same manner as in Step 1-1 and Step 1-2 of Example 1, except that 5,6-dichloro-2-(trifluoromethyl)-1H-benzo[d]imidazole was used instead of 1H-benzo[d]imidazole, thereby obtaining the title compound (28 mg, yield: 80%).

$^1$H-NMR (500 MHz, DMSO-d$_6$): δ 8.20 (d, 2H), 5.55 (dd, 2H), 4.82 (d, 1H), 3.00 (m, 2H), 2.84 (d, 1H), 2.65 (m, 1H), 2.37 (dd, 1H), 1.91 (d, 1H), 1.60 (d, 1H), 1.37 (m, 1H), 1.25 (m, 1H).

Example 51: Preparation of 1-(5,6-dichloro-2-((dimethylamino)methyl)-1H-benzo[d]imidazol-1-yl)-3-((2R,3S)-3-hydroxypiperidin-2-yl)propan-2-one

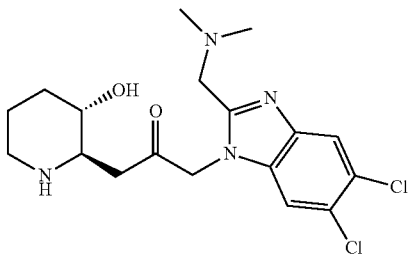 [SMILES: CN(C)Cc1nc2cc(Cl)c(Cl)cc2n1CC(=O)C[C@H]1NCCC[C@@H]1O]

(Step 51-1) Preparation of N-(2-amino-4,5-dichlorophenyl)-2-(dimethylamino)acetamide Dimethylglycine (58 mg, 0.57 mmol) was dissolved in N,N-dimethylformamide (2 mL) to which 4,5-dichlorobenzene-1,2-diamine (100 mg, 0.57 mmol), O-(benzotriazol-1-yl)-N,N,N',N'-tetramethyluronium hexafluorophosphate (320 mg, 0.85 mmol) and N,N-diisopropylethylamine (200 µL, 1.1 mmol) were added and then stirred at room temperature for 3 hours. When the reaction was completed, the solvent was removed, and the resulting mixture was diluted with ethyl acetate and then washed with saturated sodium chloride solution. The organic layer was collected, dried over magnesium sulfate, filtered and concentrated under reduced pressure, and then purified by column chromatography (dichloromethane:methanol=10:1), thereby obtaining the title compound (130 mg, yield: 87%).

(Step 51-2) Preparation of 1-(5,6-dichloro-1H-benzo[d]imidazol-2-yl)-N,N-dimethylmethanamine N-(2-amino-4,5-dichlorophenyl)-2-(dimethylamino)acetamide (130 mg, 0.50 mmol) obtained from Step 51-1 was dissolved in acetic acid (10 mL) and then stirred with heating at 65° C. for 1 hour. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethyl acetate=1:1) to obtain the title compound (115 mg, yield: 95%).

(Step 51-3) Preparation of benzyl (2R,3S)-3-(tert-butyldimethylsilyloxy)-2-(3-(5,6-dichloro-2-((dimethylamino)methyl)-1H-benzo[d]imidazol-1-yl)-2-oxopropyl)piperidin-1-carboxylate 1-(5,6-dichloro-1H-benzo[d]imidazol-2-yl)-N,N-dimethylmethanamine (115 mg, 0.47 mmol) obtained from Step 51-2 was dissolved in N,N-dimethylformamide (2 mL) to which potassium carbonate (130 mg, 0.94 mmol) was added and stirred at room temperature for 10 minutes. Then, benzyl (2R,3S)-2-(3-bromo-2-oxopropyl)-3-(tert-butyldimethylsilyloxy)piperidin-1-carboxylate (140 mg, 0.56 mmol) was added and then stirred at room temperature for 3 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethyl acetate=3:1) to obtain the title compound (130 mg, yield: 84%).

(Step 51-4) Preparation of 1-(5,6-dichloro-2-((dimethylamino)methyl)-1H-benzo[d]imidazol-1-yl)-3-((2R,3S)-3-hydroxypiperidin-2-yl)propan-2-one Benzyl (2R,3S)-3-(tert-butyldimethylsilyloxy)-2-(3-(5,6-dichloro-2-((dimethylamino)methyl)-1H-benzo[d]imidazol-1-yl)-2-oxopropyl)piperidin-1-carboxylate (130 mg, 0.20 mmol) obtained from Step 51-3 was dissolved in 6N hydrochloric acid solution (5 mL) and then stirred under reflux for 1 hour. When the reaction was completed, the reaction solution was cooled to 0° C., neutralized (pH 7) with potassium carbonate and then extracted with a mixed solution of chloroform and a small amount of acetone. The organic layer was collected, dried over magnesium sulfate, filtered and concentrated under reduced pressure, and then recrystallized with diethyl ether to obtain the title compound (61 mg, yield: 76%).
$^1$H-NMR (500 MHz, DMSO-$d_6$): δ 7.87 (d, 2H), 5.34 (dd, 2H), 4.79 (d, 1H), 3.59 (s, 2H), 2.97 (m, 1H), 2.94 (dd, 1H), 2.84 (d, 1H), 2.66 (m, 1H), 2.38 (m, 3H), 2.10 (s, 6H), 1.90 (m, 1H), 1.59 (d, 1H), 1.38 (m, 1H), 1.25 (m, 1H).

Example 52: Preparation of 1-(2-(aminomethyl)-5,6-dichloro-1H-benzo[d]imidazol-1-yl)-3-((2R,3S)-3-hydroxypiperidin-2-yl)propan-2-one

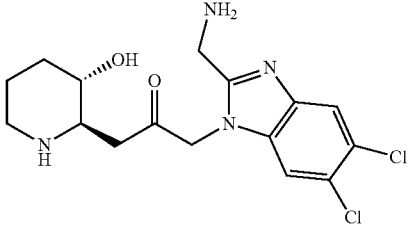 [SMILES: NCc1nc2cc(Cl)c(Cl)cc2n1CC(=O)C[C@H]1NCCC[C@@H]1O]

(Step 52-2) Preparation of 1-(2-(aminomethyl)-5,6-dichloro-1H-benzo[d]imidazol-1-yl)-3-((2R,3S)-3-hydroxypiperidin-2-yl)propan-2-one (Tert-butoxycarbonyl)glycine (300 mg, 1.7 mmol) was dissolved in N,N-dimethylformamide (10 mL) to which 4,5-dichlorobenzene-1,2-diamine (300 mg, 1.7 mmol), O-(benzotriazol-1-yl)-N,N,N',N'-tetramethyluronium hexafluorophosphate (970 mg, 2.6 mmol), and N,N-diisopropylethylamine (600 µL, 3.4 mmol) were added and then stirred at room temperature for 3 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethyl acetate=1:1) to obtain the title compound (480 mg, yield: 85%).

(Step 52-2) Preparation of 11-(2-(aminomethyl)-5,6-dichloro-1H-benzo[d]imidazol-1-yl)-3-((2R,3S)-3-hydroxypiperidin-2-yl)propan-2-one The reaction was carried out in the same manner as in Step 51-2 to Step 51-4 of Example 51, except that tert-butyl (2-((2-amino-4,5-dichlorophenyl)amino)-2-oxoethyl)carbamate obtained from Step 52-1 was used instead of N-(2-amino-4,5-dichlorophenyl)-2-(dimethylamino)acetamide, thereby obtaining the title compound (120 mg, yield: 80%).

¹H-NMR (500 MHz, DMSO-d₆): δ 7.87 (d, 2H), 4.96 (s, 1H), 4.85 (m, 2H), 3.09 (m, 1H), 3.01 (d, 1H), 2.82 (d, 1H), 2.71 (s, 1H), 2.41 (m, 1H), 2.26 (dd, 1H), 1.95 (dd, 1H), 1.61 (d, 1H), 1.39 (m, 1H), 1.26 (m, 2H).

Example 53: Preparation of 1-(6-fluoro-2-(2-hydroxyethyl)-1H-benzo[d]imidazol-1-yl)-3-((2R,3S)-3-hydroxypiperidin-2-yl)propan-2-one

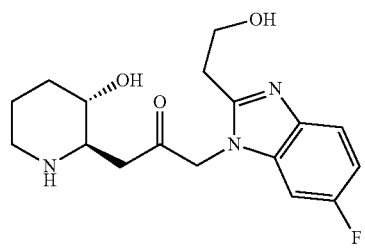 [SMILES: O=C(C[C@H]1NCCC[C@@H]1O)Cn1c(CCO)nc2ccc(F)cc21]

The reaction was carried out in the same manner as in Step 1-1 and Step 1-2 of Example 1, except that 2-(2-((tert-butyldiphenylsilyl)oxy)ethyl)-6-fluoro-1H-benzo[d]imidazole was used instead of 1H-benzo[d]imidazole, thereby obtaining the title compound (15 mg, yield: 75%).

¹H-NMR (500 MHz, DMSO-d₆): δ 7.52 (m, 1H), 7.31 (m, 1H), 6.98 (m, 1H), 5.32 (m, 2H), 4.81 (m, 2H), 3.77 (s, 2H), 3.01 (m, 1H), 2.95 (dd, 1H), 2.85 (m, 3H), 2.67 (m, 1H), 2.42 (m, 2H), 1.91 (d, 1H), 1.59 (m, 1H), 1.36 (m, 1H), 1.25 (m, 1H).

Example 54: Preparation of 1-(2-((R)-1-hydroxyethyl)-1H-benzo[d]imidazol-1-yl)-3-((2R,3S)-3-hydroxypiperidin-2-yl)propan-2-one

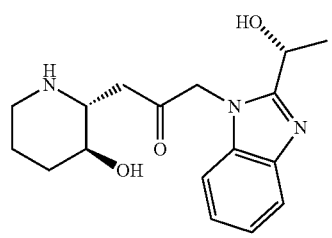 [SMILES: C[C@@H](O)c1nc2ccccc2n1CC(=O)C[C@H]1NCCC[C@@H]1O]

The reaction was carried out in the same manner as in Step 1-1 and Step 1-2 of Example 1, except that (R)-2-(1-((tert-butyldiphenylsilyl)oxy)ethyl)-1H-benzo[d]imidazole was used instead of 1H-benzo[d]imidazole, thereby obtaining the title compound (15 mg, yield: 77%).

¹H-NMR (500 MHz, DMSO-d₆): δ 7.59 (d, 1H), 7.40 (d, 1H), 7.20 (m, 2H), 5.40 (dd, 2H), 4.87 (m, 1H), 4.81 (d, 1H), 2.97 (m, 2H), 2.83 (d, 1H), 2.70 (m, 1H), 2.42 (m, 2H), 1.90 (m, 1H), 1.60 (m, 1H), 1.52 (d, 3H), 1.37 (m, 1H), 1.23 (m, 1H).

Example 55: Preparation of 1-(2-((S)-1-hydroxyethyl)-1H-benzo[d]imidazol-1-yl)-3-((2R,3S)-3-hydroxypiperidin-2-yl)propan-2-one

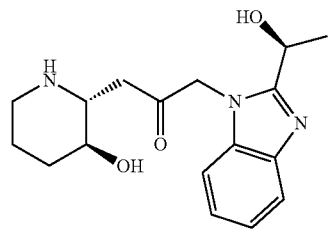 [SMILES: C[C@H](O)c1nc2ccccc2n1CC(=O)C[C@H]1NCCC[C@@H]1O]

The reaction was carried out in the same manner as in Step 1-1 and Step 1-2 of Example 1, except that (S)-2-(1-((tert-butyldiphenylsilyl)oxy)ethyl)-1H-benzo[d]imidazole was used instead of 1H-benzo[d]imidazole, thereby obtaining the title compound (15 mg, yield: 77%).

¹H-NMR (500 MHz, DMSO-d₆): δ 7.59 (d, 1H), 7.40 (d, 1H), 7.20 (m, 2H), 5.40 (dd, 2H), 4.87 (m, 1H), 4.81 (d, 1H), 2.97 (m, 2H), 2.83 (d, 1H), 2.70 (m, 1H), 2.42 (m, 2H), 1.90 (m, 1H), 1.60 (m, 1H), 1.52 (d, 3H), 1.37 (m, 1H), 1.23 (m, 1H).

Example 56: Preparation of 1-(2-(hydroxymethyl)-1H-benzo[d]imidazol-1-yl)-3-((2R,3S)-3-hydroxypiperidin-2-yl)propan-2-one

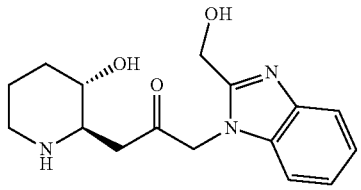 [SMILES: O=C(C[C@H]1NCCC[C@@H]1O)Cn1c(CO)nc2ccccc21]

(Step 56-1) Preparation of 2-((tert-butyldimethylsilyloxy) methyl)-1H-benzo[d]imidazole (1H-benzo[d]imidazol-2-yl)methanol (150 mg, 1.0 mmol) was dissolved in N,N-dimethylformamide (10 mL) to which triethylamine (420 μL, 3.0 mmol) was added and stirred at room temperature for 10 minutes. Then, tert-butylchlorodimethylsilane (270 mg, 1.8 mmol) was added thereto and stirred at room temperature for 3 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethyl acetate=3:1) to obtain the title compound (240 mg, yield: 90%).

(Step 56-2) Preparation of benzyl (2R,3S)-3-(tert-butyldimethylsilyloxy)-2-(3-(2-((tert-butyldimethylsilyloxy)methyl)-1H-benzo[d]imidazol-1-yl)-2-oxopropyl)piperidin-1-carboxylate 2-((tert-butyldimethylsilyloxy)methyl)-1H-benzo[d]imidazole (38 mg, 0.14 mmol) obtained from Step 56-1 was dissolved in N,N-dimethylformamide (2 mL) to which potassium carbonate (40 mg, 0.29 mmol) was added and stirred at room temperature for 10 minutes. Then, benzyl (2R,3S)-2-(3-bromo-2-oxopropyl)-3-(tert-butyldimethylsilyloxy)piperidin-1-carboxylate (70 mg, 0.14 mmol) was added and stirred at room temperature for 3 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (dichloromethane:methanol=10:1) to obtain the title compound (86 mg, yield: 90%).

(Step 56-3) Preparation of 1-(2-(hydroxymethyl)-1H-benzo[d]imidazol-1-yl)-3-((2R,3S)-3-hydroxypiperidin-2-yl)propan-2-one Benzyl (2R,3S)-3-(tert-butyldimethylsilyloxy)-2-(3-(2-((tert-butyldimethylsilyloxy)methyl)-1H-benzo[d]imidazol-1-yl)-2-oxopropyl)piperidin-1-carboxylate (86 mg, 0.13 mmol) obtained from Step 56-2 was dissolved in 6N hydrochloric acid solution (3 mL) and then stirred under reflux for 1 hour. When the reaction was completed, the reaction solution was cooled to 0° C., neutralized (pH 7) with potassium carbonate and then extracted with a mixed solution of chloroform and a small amount of acetone. The organic layer was collected, dried over magnesium sulfate, filtered and concentrated under reduced pressure, and then recrystallized with diethyl ether to obtain the title compound (32 mg, yield: 82%).
$^1$H-NMR (500 MHz, DMSO-d$_6$): δ 7.57 (m, 1H), 7.42 (m, 1H), 7.18 (m, 2H), 5.34 (dd, 2H), 4.82 (d, 1H), 4.58 (s, 2H), 2.99 (m, 1H), 2.95 (dd, 1H), 2.68 (m, 1H), 2.39 (m, 2H), 1.90 (d, 1H), 1.58 (d, 1H), 1.34 (m, 1H), 1.22 (m, 1H).

Example 57: Preparation of 1-(5-bromo-2-(hydroxymethyl)-1H-benzo[d]imidazol-1-yl)-3-((2R,3S)-3-hydroxypiperidin-2-yl)propan-2-one

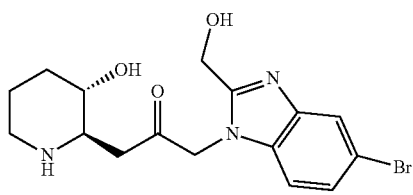 [SMILES: O=C(C[C@H]1NCCC[C@@H]1O)Cn1c(CO)nc2cc(Br)ccc21]

(Step 57-1) Preparation of benzyl (2R,3S)-3-(tert-butyldimethylsilyloxy)-2-(oxirane-2-ylmethyl)piperidin-1-carboxylate Benzyl (2R,3S)-2(3-bromo-2-oxopropyl)-3-(tert-butyldimethylsilyloxy)piperidin-1-carboxylate (7 g, 14 mmol) was dissolved in a mixed solvent of methanol and tetrahydrofuran (1:1) (30 mL) to which sodium borohydride (550 mg, 14 mmol) was added and stirred at 0° C. for 30 minutes. Then, the mixture was additionally stirred at room temperature for 12 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure. The concentrate was dissolved in ethanol (150 ml) to which potassium hydroxide (810 mg, 14 mmol) was added and then stirred at room temperature for 3 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=3:1) to obtain the title compound (4.7 mg, yield: 80%).

(Step 57-2) Preparation of benzyl (2R,3S)-2-(3-azido-2-hydroxypropyl)-3-(tert-butyldimethylsilyloxy)piperidin-1-carboxylate Benzyl (2R,3S)-3-(tert-butyldimethylsilyloxy)-2-(oxirane-2-ylmethyl)piperidin-1-carboxylate (3.0 g, 7.4 mmol) obtained from Step 57-1 was dissolved in a mixed solvent of methanol and water (8:1). Sodium azide (2.4 g, 37 mmol) and ammonium chloride (1.2 g, 22 mmol) were added thereto, heated and stirred at 50° C. for 12 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=3:1) to obtain the title compound (3.3 mg, yield: 99%).

(Step 57-3) Preparation of benzyl (2R,3S)-2-(3-amino-2-hydroxypropyl)-3-(tert-butyldimethylsilyloxy)piperidin-1-carboxylate Benzyl (2R,3S)-2-(3-azido-2-hydroxypropyl)-3-(tert-butyldimethylsilyloxy)piperidin-1-carboxylate (2.8 g, 5.8 mmol) obtained from Step 57-2 was dissolved in tetrahydrofuran (130 mL) to which triphenylphosphine (3.0 g, 12 mmol) and water (0.13 mL) were added and then stirred at room temperature for 6 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (dichloromethane:methanol=10:1+1% triethylamine) to obtain the title compound (2.0 g, yield: 80%).

(Step 57-4) Preparation of benzyl (2R,3S)-2-(3-((4-bromo-2-nitrophenyl)amino)-2-hydroxypropyl)-3-(tert-butyldimethylsilyloxy)piperidin-1-carboxylate Benzyl (2R,3S)-2-(3-amino-2-hydroxypropyl)-3-(tert-butyldimethylsilyloxy)piperidin-1-carboxylate (980 mg, 2.2 mmol) obtained from Step 57-3 was dissolved in N,N-dimethylformamide (10 mL) to which N,N-diisopropylethylamine (0.77 mL, 4.4 mmol) and 4-bromo-1-fluoro-2-nitrobenzene (490 mg, 2.2 mmol) were added and stirred at 50° C. for 6 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=3:1) to obtain the title compound (580 mg, yield: 42%).

(Step 57-5) Preparation of benzyl (2R,3S)-2-(3-((4-bromo-2-((tert-butyldiphenylsilyl)oxy)acetamido)phenyl)amino)-2-hydroxypropyl)-3-(tert-butyldimethylsilyloxy)piperidin-1-carboxylate Benzyl (2R,3S)-2-(3-((4-bromo-2-nitrophenyl)amino)-2-hydroxypropyl)-3-(tert-butyldimethylsilyloxy)piperidin-1-carboxylate (550 mg, 0.88 mmol) obtained from Step 57-4 was dissolved in methanol (6 mL) to which Raney nickel (1 mL) was added, filled with hydrogen gas and then stirred at room temperature. When the reaction was completed, the organic layer was dried and then dissolved in N,N-dimethylformamide (10 mL) to which 2-((tert-butyldiphenylsilyl)oxy)acetic acid (280 mg, 0.88 mmol) and diisopropylethylamine (0.38 mL, 2.2 mmol) were added and then stirred at room temperature for 3 hours. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=3:1) to obtain the title compound (360 mg, yield: 46%).

(Step 55-6) Preparation of benzyl (2R,3S)-2-(3-(5-bromo-2-(((tert-butyldiphenylsilyl)oxy)methyl)-1H-benzo[d]imidazol-1-yl)-2-hydroxypropyl)-3-(tert-butyldimethylsilyloxy)piperidin-1-carboxylate Benzyl (2R,3S)-2-(3-((4-bromo-2-(2-((tert-butyldiphenylsilyl)oxy)acetamido)phenyl)amino)-2-hydroxypropyl)-3-((tert-butyldimethylsilyloxy)piperidin-1-carboxylate (160 mg, 0.18 mmol) obtained from Step 57-5 was added and dissolved in acetic acid (6 mL) and then stirred at 65° C. for 3 hours. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=3:1) to obtain the title compound (140 mg, yield: 92%).

(Step 55-7) Preparation of benzyl (2R,3S)-2-(3-(5-bromo-2-(((tert-butyldiphenylsily)oxy)methyl)-1H-benzo[d]imidazol-1-yl)-2-oxopropyl)-3-((tert-butyldimethylsilyl)oxy)piperidin-1-carboxylate Benzyl (2R,3S)-2-(3-(5-bromo-2-(((tert-butyldiphenylsilyl)oxy)methyl)-1H-benzo[d]imidazol-1-yl)-2-hydroxypropyl)-3-((tert-butyldimethylsilyloxy)piperidin-1-carboxylate (140 mg, 0.17 mmol) obtained from Step 57-6 was dissolved in dichloromethane (5 mL) to which 1,1,1-triacetoxy-1,1-dihydro-1,2-benziodoxol-3(1H)-one (110 mg, 0.25 mmol) was added at 0° C. and stirred at the same temperature for 1 hour, followed by stirring at room temperature for 3 hours. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=3:1) to obtain the title compound (120 mg, yield: 88%).

(Step 55-8) Preparation of 1-(5-bromo-2-(hydroxymethyl)-1H-benzo[d]imidazol-1-yl)-3-((2R,3S)-3-hydroxypiperidin-2-yl)propan-2-one Benzyl (2R,3S)-2-(3-(5-bromo-2-(((tert-butyldiphenylsilyl)oxy)methyl)-1H-benzo[d]imidazol-1-yl)-2-oxopropyl)-3-((tert-butyldimethylsilyloxy)piperidin-1-carboxylate (40 mg, 0.05 mmol) obtained from Step 57-7 was dissolved in 6N hydrogen chloride solution (4 mL) and then stirred under reflux for 1 hour. When the reaction was completed, the reaction solution was cooled to 0° C., neutralized (pH 7) with potassium carbonate and then extracted with a mixed solution of chloroform and a small amount of acetone. The organic layer was collected, dried over magnesium sulfate, filtered and concentrated under reduced pressure, and then recrystallized with diethyl ether to obtain the title compound (13 mg, yield: 74%).

$^1$H-NMR (500 MHz, DMSO-$d_6$): δ 7.77 (d, 1H), 7.43 (d, 1H), 7.34 (d, 1H), 5.36 (dd, 2H), 4.81 (d, 1H), 4.59 (s, 2H), 3.00 (m, 1H), 2.95 (dd, 1H), 2.81 (d, 1H), 2.66 (m, 1H), 2.38 (m, 2H), 1.90 (m, 1H), 1.59 (d, 1H), 1.34 (m, 1H), 1.24 (m, 1H).

Example 58: Preparation of 1-(6-bromo-2-(hydroxymethyl)-1H-benzo[d]imidazol-1-yl)-3-((2R,3S)-3-hydroxypiperidin-2-yl)propan-2-one

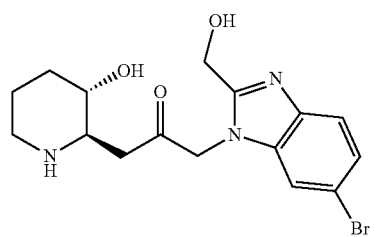 [SMILES: O=C(C[C@H]1NCCC[C@@H]1O)Cn1c(CO)nc2ccc(Br)cc21]

The reaction was carried out in the same manner as in Step 57-1 to Step 57-8 of Example 57, except that 4-bromo-2-fluoro-1-nitrobenzene was used instead of 4-bromo-1-fluoro-2-nitrobenzene in Step 57-4 of Example 57, thereby obtaining the title compound (15 mg, yield: 77%).

$^1$H-NMR (500 MHz, DMSO-$d_6$): δ 7.77 (s, 1H), 7.53 (d, 1H), 7.30 (d, 1H), 5.36 (dd, 2H), 4.82 (d, 1H), 4.58 (s, 2H), 3.00 (m, 1H), 2.96 (dd, 1H), 2.83 (d, 1H), 2.68 (m, 1H), 2.40 (m, 2H), 1.91 (d, 1H), 1.60 (d, 1H), 1.35 (m, 1H), 1.25 (m, 1H).

Example 59: Preparation of 1-(2-(hydroxymethyl)-6-(trifluoromethyl)-1H-benzo[d]imidazol-1-yl)-3-((2R,3S)-3-hydroxypiperidin-2-yl)propan-2-one

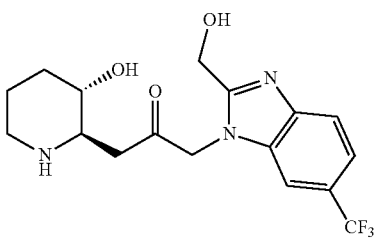 [SMILES: O=C(C[C@H]1NCCC[C@@H]1O)Cn1c(CO)nc2ccc(C(F)(F)F)cc21]

The reaction was carried out in the same manner as in Step 57-1 to Step 57-8 of Example 57, except that 2-fluoro-1-nitro-4-(trifluoromethyl)benzene was used instead of 4-bromo-1-fluoro-2-nitrobenzene in Step 57-4 of Example 57, thereby obtaining the title compound (16 mg, yield: 58%).

¹H-NMR (500 MHz, DMSO-d₆): δ 7.99 (s, 1H), 7.79 (m, 1H), 7.51 (m, 1H), 5.49 (m, 2H), 4.83 (m, 1H), 4.65 (s, 2H), 4.33 (m, 1H), 4.15 (m, 1H), 3.00 (m, 1H), 2.83 (m, 1H), 2.68 (m, 1H), 2.37 (m, 1H), 1.92 (m, 1H), 1.60 (m, 1H), 1.16-1.38 (m, 2H).

Example 60: Preparation of 1-(2-(hydroxymethyl)-5-(trifluoromethoxy)-1H-benzo[d]imidazol-1-yl)-3-((2R,3S)-3-hydroxypiperidin-2-yl)propan-2-one

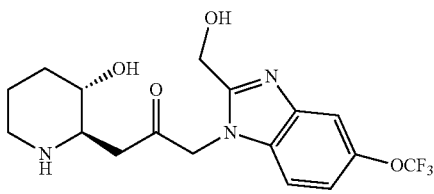 [SMILES: O=C(C[C@H]1NCCC[C@@H]1O)Cn1c(CO)nc2cc(OC(F)(F)F)ccc21]

The reaction was carried out in the same manner as in Step 57-1 to Step 57-8 of Example 57, except that 1-fluoro-2-nitro-4-(trifluoromethoxy)benzene was used instead of 4-bromo-1-fluoro-2-nitrobenzene in Step 57-7 of Example 57, thereby obtaining the title compound (15 mg, yield: 61%).

¹H-NMR (500 MHz, DMSO-d₆): δ 7.59 (m, 2H), 7.22 (m, 1H), 5.39 (m, 2H), 4.83 (d, 1H), 4.61 (s, 2H), 3.01 (m, 1H), 2.96 (dd, 1H), 2.81 (d, 1H), 2.67 (d, 1H), 2.43 (m, 1H), 2.35 (m, 1H), 2.10 (s, 1H), 1.92 (d, 1H), 1.59 (d, 1H), 1.34 (m, 1H), 1.24 (m, 1H).

Example 61: Preparation of 1-(2-(hydroxymethyl)-7-(trifluoromethoxy)-1H-benzo[d]imidazol-1-yl)-3-((2R,3S)-3-hydroxypiperidin-2-yl)propan-2-one

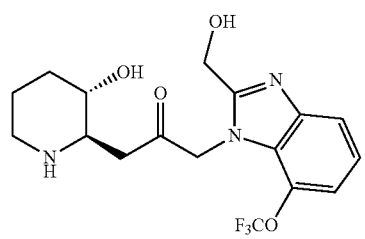 [SMILES: O=C(C[C@H]1NCCC[C@@H]1O)Cn1c(CO)nc2cccc(OC(F)(F)F)c21]

The reaction was carried out in the same manner as in Step 57-1 to Step 57-8 of Example 57, except that 2-fluoro-1-nitro-3-(trifluoromethoxy)benzene was used instead of 4-bromo-1-fluoro-2-nitrobenzene in Step 57-4 of Example 57, thereby obtaining the title compound (8 mg, yield: 46%).

¹H-NMR (500 MHz, DMSO-d₆): δ 7.63 (d, 1H), 7.24 (m, 2H), 5.40 (m, 2H), 4.75 (m, 1H), 4.63 (m, 2H), 4.25 (s, 1H), 3.99 (d, 1H), 2.81 (m, 1H), 2.65 (m, 1H), 2.41 (m, 1H), 2.34 (m, 1H), 1.90 (m, 1H), 1.63 (m, 1H), 1.32 (m, 1H), 1.22 (m, 1H).

Example 62: Preparation of 1-(2-(hydroxymethyl)-4,5-dimethyl-1H-benzo[d]imidazol-1-yl)-3-((2R,3S)-3-hydroxypiperidin-2-yl)propan-2-one

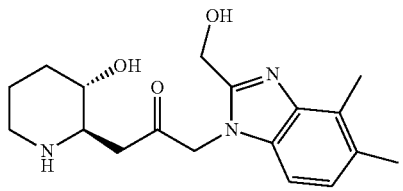 [SMILES: Cc1ccc2c(nc(CO)n2CC(=O)C[C@H]2NCCC[C@@H]2O)c1C]

The reaction was carried out in the same manner as in Step 1-1 and Step 1-2 of Example 1, except that 2-(((tert-butyldiphenylsilyl)oxy)methyl)-4,5-dimethyl-1H-benzo[d]imidazole was used instead of 1H-benzo[d]imidazole, thereby obtaining the title compound (36 mg, yield: 72%).

¹H-NMR (500 MHz, DMSO-d₆): δ 7.11 (d, 1H), 6.98 (d, 1H), 5.27 (dd, 2H), 4.78 (d, 1H), 4.58 (s, 2H), 2.98 (m, 1H), 2.93 (dd, 1H), 2.81 (d, 1H), 2.66 (m, 1H), 2.44 (s, 3H), 2.40 (m, 2H), 2.30 (s, 3H), 1.90 (m, 1H), 1.58 (d, 1H), 1.33 (m, 1H), 1.22 (m, 1H).

Example 63: Preparation of 1-(5,6-dichloro-2-(methoxymethyl)-1H-benzo[d]imidazol-1-yl)-3-((2R,3S)-3-hydroxypiperidin-2-yl)propan-2-one

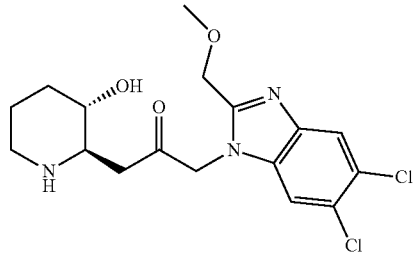 [SMILES: COCc1nc2cc(Cl)c(Cl)cc2n1CC(=O)C[C@H]1NCCC[C@@H]1O]

The reaction was carried out in the same manner as in Step 1-1 and Step 1-2 of Example 1, except that 5,6-dichloro-2-(methoxymethyl)-1H-benzo[d]imidazole was used instead of 1H-benzo[d]imidazole, thereby obtaining the title compound (28 mg, yield: 78%).

¹H-NMR (500 MHz, DMSO-d₆): δ 7.91 (s, 2H), 5.34 (dd, 2H), 4.82 (d, 1H), 4.57 (s, 2H), 3.22 (s, 3H), 3.00 (M, 1H), 2.95 (dd, 1H), 2.84 (d, 1H), 2.65 (m, 1H), 2.38 (m, 2H), 1.91 (m, 1H), 1.59 (d, 1H), 1.35 (m, 1H), 1.23 (m, 1H).

Example 64: Preparation of 1-(5,6-dichloro-1H-benzo[d]imidazol-1-yl)-3-((2R,3S)-3-hydroxypiperidin-2-yl)propan-2-one oxime

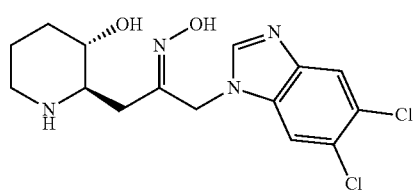 [SMILES: O/N=C(/C[C@H]1NCCC[C@@H]1O)Cn1cnc2cc(Cl)c(Cl)cc21]

1-(5,6-dichloro-1H-benzo[d]imidazol-1-yl)-3-((2R,3S)-3-hydroxypiperidin-2-yl)propan-2-one (50 mg, 0.15 mmol) obtained from Example 25 was dissolved in ethanol (1.5 mL) to which hydroxylamine (20 μL, 0.73 mmol) and sodium acetate (72 mg, 0.88 mmol) were slowly added and then stirred under reflux for 1 hour. When the reaction was completed, the solvent was evaporated under reduced pressure and extracted with ethyl acetate. The extract was dried over magnesium sulfate, filtered and concentrated under reduced pressure, followed by crystallization to obtain the title compound (15 mg, yield: 29%).

$^1$H-NMR (500 MHz, DMSO-d$_6$): δ 11.37 (s, 1H), 8.40 (s, 1H), 7.98 (s, 1H), 5.10 (m, 2H), 4.51 (d, 1H), 2.89-2.96 (m, 1H), 2.74-2.87 (m, 1H), 2.65-2.70 (m, 1H), 2.19-2.28 (m, 2H), 1.83-1.98 (m, 1H), 1.81 (m, 1H), 1.51 (m, 1H), 1.07-1.25 (m, 1H).

Example 65: Preparation of 1-(5,6-dichloro-2-(hydroxymethyl)-1H-benzo[d]imidazol-1-yl)-3-((2R,3S)-3-hydroxypiperidin-2-yl)propan-2-one oxime

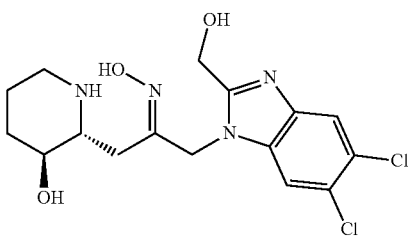 [SMILES: OCc1nc2cc(Cl)c(Cl)cc2n1C/C(C[C@H]1NCCC[C@@H]1O)=N/O]

The reaction was carried out in the same manner as in Example 64, except that 1-(5,6-dichloro-2-(hydroxymethyl)-1H-benzo[d]imidazol-1-yl)-3-((2R,3S)-3-hydroxypiperidin-2-piperidin-2-one was used instead of 1-(5,6-dichloro-1H-benzo[d]imidazol-1-yl)-3-((2R,3S)-3-hydroxypiperidin-2-yl)propan-2-one, thereby obtaining the title compound (35 mg, yield: 71%).

$^1$H-NMR (500 MHz, DMSO-d$_6$): δ 7.80-7.95 (m, 2H), 5.19 (m, 2H), 4.73 (m, 1H), 4.67 (s, 1H), 2.99 (m, 1H), 2.87 (d, 2H), 2.75 (m, 2H), 2.61 (m, 1H), 2.30 (m, 2H), 1.74 (d, 2H), 1.60 (m, 1H).

Example 66: Preparation of 1-(6-bromo-1H-imidazo[4,5-b]pyridin-1-yl)-3-((2R,3S)-3-hydroxypiperidin-2-yl)propan-2-one oxime

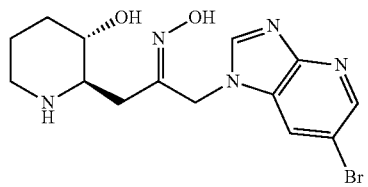 [SMILES: O/N=C(/C[C@H]1NCCC[C@@H]1O)Cn1cnc2ncc(Br)cc21]

The reaction was carried out in the same manner as in Example 64, except that 1-(6-bromo-1H-imidazo[4,5-b]pyridin-1-yl)-3-((2R,3S)-3-hydroxypiperidin-2-yl)propan-2-one was used instead of 1-(5,6-dichloro-1H-benzo[d]imidazol-1-yl)-3-((2R,3S)-3-hydroxypiperidin-2-yl)propan-2-one, thereby obtaining the title compound (20 mg, yield: 38%).

$^1$H-NMR (500 MHz, DMSO-d$_6$): δ 8.36-8.51 (m, 3H), 5.12 (d, 2H), 2.94 (m, 1H), 2.82 (d, 1H), 2.74 (m, 2H), 2.27 (m, 3H), 1.88 (m, 1H), 1.62 (m, 1H), 1.48 9 m, 1H), 1.18-1.39 (m 2H).

Example 67: Preparation of 1-(5,6-dichloro-1H-benzo[d]imidazol-1-yl)-3-((2R,3S)-3-hydroxypiperidin-2-yl)propan-2-one O-methyl oxime

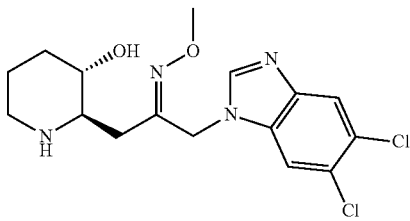 [SMILES: CO/N=C(/C[C@H]1NCCC[C@@H]1O)Cn1cnc2cc(Cl)c(Cl)cc21]

The reaction was carried out in the same manner as in Example 64, except that methyl hydroxylamine was used instead of hydroxylamine, thereby obtaining the title compound (15 mg, yield: 28%).

$^1$H-NMR (500 MHz, DMSO-d$_6$): δ 8.38 (d, 1H), 7.84-7.98 (m, 2H), 5.14 (m, 2H), 4.64 (d, 1H), 4.04 (m, 1H), 3.86 (d, 3H), 2.94 (m, 1H), 2.81 (m, 1H), 2.65 (m. 1H), 2.30 (m, 1H), 2.14 (m, 1H), 1.76 (m, 1H), 1.55 (m, 1H).

Example 68: Preparation of 1-(2-(hydroxymethyl)-1H-imidazo[4,5-b]pyridin-1-yl)-3-((2R,3S)-3-hydroxypiperidin-2-yl)propan-2-one

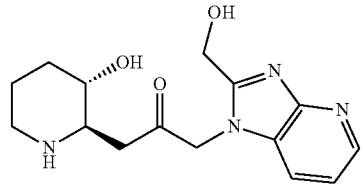 [SMILES: O=C(C[C@H]1NCCC[C@@H]1O)Cn1c(CO)nc2ncccc21]

The reaction was carried out in the same manner as in Step 1-1 and Step 1-2 of Example 1, except that 2-(((tert-butyldiphenylsilyl)oxy)methyl)-1H-imidazo[4,5-d]pryidine was used instead of 1H-benzo[d]imidazole, thereby obtaining the title compound (20 mg, yield: 71%).

$^1$H-NMR (500 MHz, DMSO-d$_6$): δ 8.27 (d, 1H), 8.03 (d, 1H), 7.26 (dd, 1H), 5.37 (dd, 2H), 4.81 (d, 1H), 3.03 (d, 1H), 2.82 (d, 1H), 2.70 (m, 1H), 2.41 (m, 2H), 1.91 (d, 1H), 1.59 (d, 1H), 1.36 (m, 1H), 1.23 (m, 1H

Example 69: Preparation of (2R,3S)-2-(3-(1H-benzo[d]imidazol-1-yl)-2-hydroxypropyl)piperidin-3-ol

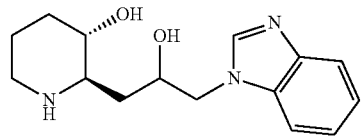 [SMILES: OC(C[C@H]1NCCC[C@@H]1O)Cn1cnc2ccccc21]

(Step 69-1) Preparation of benzyl (2R,3S)-2-(3-(1H-benzo [d]imidazol-1-yl)-2-hydroxypropyl)-3-(tert-butyldimethylsilyloxy)piperidin-1-carboxylate Benzyl (2R,3S)-3-(tert-butyldimethylsilyloxy)-2-(3-(1H-benzo[d]imidazol-1-yl)-2-oxopropyl)piperidin-1-carboxylate (200 mg, 0.34 mmol) was dissolved in methanol (1 mL) and then cooled to 0° C. Sodium borohydride (39 mg, 1.0 mmol) was slowly added thereto. After raising the reaction temperature to room temperature, the mixture was stirred for 1 hour. When the reaction was completed, it was terminated with water, extracted with ethyl acetate. The extract was dried over magnesium sulfate, filtered and concentrated under reduced pressure, and then purified by column chromatography (ethyl acetate) to obtain the title compound (180 mg, yield: 90%).

(Step 69-2) Preparation of (2R,3S)-2-(3-(1H-benzo [d]imidazol-1-yl)-2-hydroxypropyl)piperidin-3-ol The reaction was carried out in the same manner as in Step 1-2 of Example 1, except that benzyl (2R,3S)-2-(3-(1H-benzo[d]imidazol-1-yl)-2-hydroxypropyl)-3-(tert-butyldimethylsilyloxy)piperidin-1-carboxylate obtained from Step 69-1 was used instead of benzyl (2R,3S)-2-(3-(1H-benzo[d]imidazol-1-yl)-2-oxopropyl)-3-(tert-butyldimethylsilyloxy)piperidin-1-carboxylate, thereby obtaining the title compound (24 mg, yield: 78%).

$^1$H-NMR (500 MHz, MeOH-d$_4$): δ 8.23 (s, 1H), 7.68 (m, 2H), 7.34-7.28 (m, 2H), 4.39-4.31 (m, 2H), 3.47-3.45 (m, 1H), 3.23-3.21 (m, 1H), 3.12-3.07 (m, 1H), 2.91 (m, 1H), 2.34-2.31 (m, 1H), 2.06-2.05 (m, 1H), 2.03-1.95 (m, 1H), 1.68-1.51 (m, 4H).

Example 70: Preparation of (2R,3S)-2-(3-(5,6-dichloro-1H-benzo[d]imidazol-1-yl)-2-hydroxypropyl)piperidin-3-ol

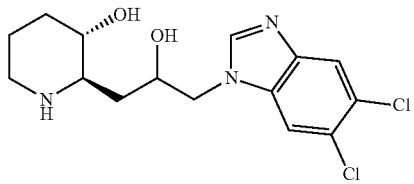 [SMILES: OC(C[C@H]1NCCC[C@@H]1O)Cn1cnc2cc(Cl)c(Cl)cc21]

The reaction was carried out in the same manner as in Step 69-1 and Step 69-2 of Example 69, except that benzyl (2R,3S)-3-(tert-butyldimethylsilyloxy)-2-(3-(5,6-dichloro-1H-benzo[d]imidazol-1-yl)-2-oxopropyl)piperidin-1-carboxylate was used instead of benzyl (2R,3S)-3-(tert-butyldimethylsilyloxy)-2-(3-1H-benzo[d]imidazol-1-yl)-2-oxopropyl)piperidin-1-carboxylate, thereby obtaining the title compound (22 mg, yield: 75%).

$^1$H-NMR (500 MHz, DMSO-d$_6$): δ 8.16 (s, 1H), 7.78 (d, 1H), 7.46 (dd, 1H), 7.30-7.27 (m, 2H), 4.21 (s, 2H), 3.06-3.05 (m, 1H), 2.94-2.92 (m, 1H), 2.36-2.35 (m, 1H), 2.27-2.24 (m, 2H), 2.20-2.17 (m, 2H), 1.74-1.71 (m, 1H), 1.40-1.35 (m, 2H), 1.26-1.23 (m, 1H), 1.22 (s, 3H).

Example 71: Preparation of (2R,3S)-2-(3-(5-bromo-4-chloro-1H-benzo[d]imidazol-1-yl)-2-hydroxypropyl)piperidin-3-ol

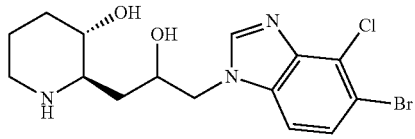

The reaction was carried out in the same manner as in Step 69-1 and Step 69-2 of Example 69, except that benzyl (2R,3S)-2-(3-(5-bromo-4-chloro-1H-benzo[d]imidazol-1-yl)-2-hydroxypropyl)-3-(tert-butyldimethylsilyloxy)piperidin-1-carboxylate was used instead of benzyl (2R,3S)-3-(tert-butyldimethylsilyloxy)-2-(3-1H-benzo[d]imidazol-1-yl)-2-oxopropyl)piperidin-1-carboxylate, thereby obtaining the title compound (28 mg, yield: 75%).

$^1$H-NMR (500 MHz, DMSO-d$_6$): δ 8.26 (s, 1H), 7.61 (d, 1H), 7.56 (d, 1H), 4.61 (d, 1H), 4.30 (d, 1H), 4.13 (m, 1H), 4.02 (s, 1H), 2.90 (m, 1H), 2.76 (d, 1H), 2.33 (m, 1H), 2.03 (d, 1H), 1.86 (d, 1H), 1.54 (d, 1H), 1.33 (m, 1H), 1.20 (m, 1H), 1.05 (m, 1H).

Example 72: Preparation of (2R,3S)-2-(3-(5-bromo-4-(trifluoromethyl)-1H-benzo[d]imidazol-1-yl)-2-hydroxypropyl)piperidin-3-ol

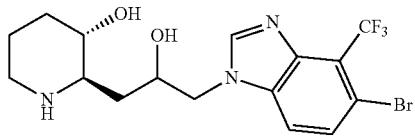

The reaction was carried out in the same manner as in Step 69-1 and Step 69-2 of Example 69, except that benzyl (2R,3S)-3-(tert-butyldimethylsilyloxy)-2-(3-(5-bromo-4-(trifluoromethyl)-1H-benzo[d]imidazol-1-yl)-2-oxopropyl)piperidin-1-carboxylate was used instead of benzyl (2R,3S)-3-(tert-butyldimethylsilyloxy)-2-(3-1H-benzo[d]imidazol-1-yl)-2-oxopropyl)piperidin-1-carboxylate, thereby obtaining the title compound (21 mg, yield: 74%).

$^1$H-NMR (500 MHz, DMSO-d$_6$): δ 8.33 (s, 1H), 7.85 (d, 1H), 7.62 (d, 1H), 5.99 (s, 1H), 4.59 (s, 1H), 4.32 (m, 1H), 4.15 (m, 1H), 4.12 (m, 1H), 2.88 (m, 1H), 2.71 (d, 1H), 2.29 (m, 1H), 2.07 (m, 1H), 1.99 (d, 1H), 1.82 (m, 1H), 1.50 (m, 1H), 1.29 (m, 1H), 1.21 (m, 1H), 1.15 (m, 1H).

Example 73: Preparation of (2R,3S)-2-(3-(4-bromo-5-methyl-1H-benzo[d]imidazol-1-yl)-2-hydroxypropyl)piperidin-3-ol

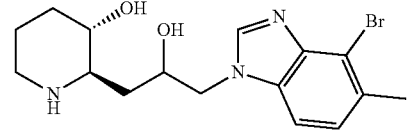 [SMILES: Cc1ccc2c(ncn2CC(O)C[C@H]2NCCC[C@@H]2O)c1Br]

The reaction was carried out in the same manner as in Step 69-1 and Step 69-2 of Example 69, except that benzyl (2R,3S)-3-(tert-butyldimethylsilyloxy)-2-(3-(4-bromo-5-methyl-1H-benzo[d]imidazol-1-yl)-oxopropyl)piperidin-1-carboxylate was used instead of benzyl (2R,3S)-3-(tert-butyldimethylsilyloxy)-2-(3-1H-benzo[d]imidazol-1-yl)-2-oxopropyl)piperidin-1-carboxylate, thereby obtaining the title compound (18 mg, yield: 65%).

$^1$H-NMR (500 MHz, DMSO-$d_6$): δ 8.16 (s, 1H), 7.51 (d, 1H), 7.20 (d, 1H), 4.60 (m, 1H), 4.23 (m, 1H), 4.10 (m, 1H), 4.05 (m, 1H), 2.91 (m, 1H), 2.75 (m, 1H), 2.45 (s, 3H), 2.35 (m, 2H), 2.08 (d, 1H), 1.86 (d, 1H), 1.55 (m, 1H), 1.34 (m, 1H), 1.23 (m, 1H), 1.05 (m, 1H).

Example 74: Preparation of (2R,3S)-2-(3-(5-bromo-4-fluoro-1H-benzo[d]imidazol-1-yl)-2-hydroxypropyl)piperidin-3-ol

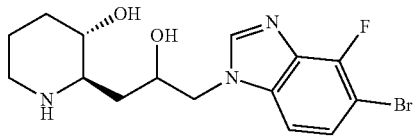

The reaction was carried out in the same manner as in Step 69-1 and Step 69-2 of Example 69, except that benzyl (2R,3S)-3-(tert-butyldimethylsilyloxy)-2-(3-(5-bromo-4-fluoro-1H-benzo[d]imidazol-1-yl)-2-oxopropyl)piperidin-1-carboxylate was used instead of benzyl (2R,3S)-3-(tert-butyldimethylsilyloxy)-2-(3-1H-benzo[d]imidazol-1-yl)-2-oxopropyl)piperidin-1-carboxylate, thereby obtaining the title compound (17 mg, yield: 63%).

$^1$H-NMR (500 MHz, DMSO-$d_6$): δ 8.22 (s, 1H), 7.45 (m, 2H), 7.43 (m, 3H), 4.62 (m, 1H), 4.28 (m, 1H), 4.15 (m, 1H), 4.05 (m, 1H), 2.91 (m, 1H), 2.73 (m, 1H), 2.30 (m, 2H), 2.07 (m, 1H), 1.97 (m, 1H), 1.89 (m, 1H), 1.54 (m, 1H), 1.33 (m, 1H), 1.25 (m, 1H), 1.05 (m, 1H).

Example 75: Preparation of (2R,3S)-2-(3-(4,5-dichloro-1H-benzo[d]imidazol-1-yl)-2-hydroxypropyl)piperidin-3-ol

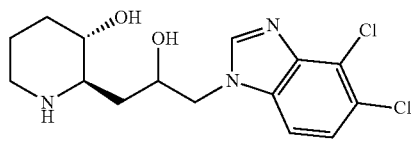

The reaction was carried out in the same manner as in Step 69-1 and Step 69-2 of Example 69, except that benzyl (2R,3S)-3-(tert-butyldimethylsilyloxy)-2-(3-(4,5-dichloro-1H-benzo[d]imidazol-1-yl)-2-oxopropyl)piperidin-1-carboxylate was used instead of benzyl (2R,3S)-2-(3-(5-bromo-4-chloro-1H-benzo[d]imidazol-1-yl)-2-oxopropyl)-3-(tert-butyldimethylsilyloxy)piperidin-1-carboxylate, thereby obtaining the title compound (22 mg, yield: 74%).

$^1$H-NMR (500 MHz, DMSO-$d_6$): δ 8.29 (d, 1H), 7.66 (d, 1H), 7.65 (d, 1H), 4.61 (d, 1H), 4.31 (d, 1H), 4.13 (m, 1H), 4.03 (s, 1H), 2.90 (m, 1H), 2.76 (d, 1H), 2.30 (m, 2H), 2.03 (d, 1H), 1.86 (d, 1H), 1.54 (d, 1H), 1.33 (m, 1H), 1.21 (m, 1H), 1.05 (m, 1H).

Example 76: Preparation of (2R,3S)-2-(3-(5-chloro-4-methyl-1H-benzo[d]imidazol-1-yl)-2-hydroxypropyl)piperidin-3-ol

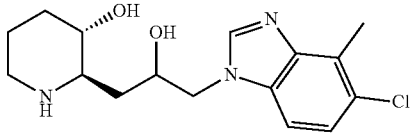 [SMILES: Cc1c(Cl)ccc2c1ncn2CC(O)C[C@H]1NCCC[C@@H]1O]

The reaction was carried out in the same manner as in Step 69-1 and Step 69-2 of Example 69, except that benzyl (2R,3S)-3-(tert-butyldimethylsilyloxy)-2-(3-(5-chloro-4-methyl-1H-benzo[d]imidazol-1-yl)-2-oxopropyl)piperidin-1-carboxylate was used instead of benzyl (2R,3S)-3-(tert-butyldimethylsilyloxy)-2-(3-(1H-benzo[d]imidazol-1-yl)-2-oxopropyl)piperidin-1-carboxylate, thereby obtaining the title compound (22 mg, yield: 71%).

$^1$H-NMR (500 MHz, DMSO-$d_6$): δ 8.17 (s, 1H), 7.46 (d, 1H), 7.25 (d, 1H), 6.01 (m, 1H), 4.60 (m, 1H), 4.23 (m, 1H), 4.10 (m, 1H), 4.02 (m, 1H), 2.91 (m, 1H), 2.75 (m, 1H), 2.29 (m, 1H), 2.10 (m, 1H), 2.02 (m, 1H), 1.85 (m, 1H), 1.53 (m, 1H), 1.33 (m, 1H), 1.24 (m, 1H), 1.12 (m, 1H).

Example 77: Preparation of (2R,3S)-2-(3-(6-chloro-7-methyl-3H-imidazo[4,5-b]pyridin-3-yl)-2-hydroxypropyl)piperidin-3-ol

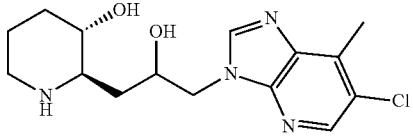 [SMILES: Cc1c(Cl)cnc2c1ncn2CC(O)C[C@H]1NCCC[C@@H]1O]

The reaction was carried out in the same manner as in Step 69-1 and Step 69-2 of Example 69, except that benzyl (2R,3S)-3-(tert-butyldimethylsilyloxy)-2-(3-(6-chloro-7-methyl-3H-imidazo[4,5-b]pyridin-3-yl)-2-hydroxypropyl)piperidin-1-carboxylate was used instead of benzyl (2R,3S)-3-(tert-butyldimethylsilyloxy)-2-(3-(1H-benzo[d]imidazole-1-yl)-oxopropyl)piperidin-1-carboxylate, thereby obtaining the title compound (20 mg, yield: 75%).

$^1$H-NMR (500 MHz, DMSO-$d_6$): δ 8.37 (s, 1H), 8.32 (d, 1H), 4.54 (m, 1H), 4.22 (m, 1H), 4.12 (m, 2H), 2.88 (m, 1H), 2.70 (d, 1H), 2.59 (s, 3H), 2.34 (m, 2H), 1.98 (m, 1H), 1.84 (m, 1H), 1.53 (m, 1H), 1.32 (m, 1H), 1.20 (m, 1H), 1.05 (m, 2H).

Example 78: Preparation of (2R,3S)-2-(3-(6-bromo-7-methyl-3H-imidazo[4,5-b]pyridin-3-yl)-2-hydroxypropyl)piperidin-3-ol

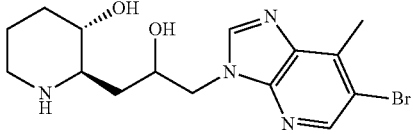 [SMILES: Cc1c(Br)cnc2c1ncn2CC(O)C[C@H]1NCCC[C@@H]1O]

The reaction was carried out in the same manner as in Step 69-1 and Step 69-2 of Example 69, except that benzyl (2R,3S)-3-(tert-butyldimethylsilyloxy)-2-(3-(6-bromo-7-methyl-3H-imidazo[4,5-b]pyridin-3-yl)-2-hydroxypropyl)piperidin-1-carboxylate was used instead of benzyl (2R,3S)-3-(tert-butyldimethylsilyloxy)-2-(3-(1H-benzo[d]imidazol-1-yl)-2-oxopropyl)piperidin-1-carboxylate, thereby obtaining the title compound (27 mg, yield: 77%).

$^1$H-NMR (500 MHz, DMSO-$d_6$): δ 8.42 (s, 1H), 8.36 (s, 1H), 6.02 (s, 1H), 4.55 (d, 1H), 4.23 (m, 1H), 4.13 (m, 2H), 2.89 (m, 1H), 2.77 (m, 1H), 2.60 (s, 3H), 2.27 (m, 1H), 2.17 (m, 1H), 1.98 (d, 1H), 1.83 (d, 1H), 1.52 (d, 1H), 1.31 (m, 1H), 1.27 (m, 1H), 1.18 (m, 1H).

Example 79: Preparation of (2R,3S)-2-(3-(6-bromo-7-chloro-3H-imidazo[4,5-b]pyridin-3-yl)-2-hydroxypropyl)piperidin-3-ol

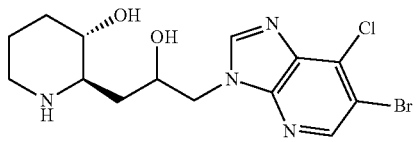 [SMILES: OC(C[C@H]1NCCC[C@@H]1O)Cn1cnc2c(Cl)c(Br)cnc21]

The reaction was carried out in the same manner as in Step 69-1 and Step 69-2 of Example 69, except that benzyl (2R,3S)-3-(tert-butyldimethylsilyloxy)-2-(3-(6-bromo-7-chloro-3H-imidazo[4,5-b]pyridin-3-yl)-2-hydroxypropyl)piperidin-1-carboxylate was used instead of benzyl (2R,3S)-3-(tert-butyldimethylsilyloxy)-2-(3-(1H-benzo[d]imidazol-1-yl)-2-oxopropyl)piperidin-1-carboxylate, thereby obtaining the title compound (20 mg, yield: 70%).

$^1$H-NMR (500 MHz, DMSO-$d_6$): δ 8.59 (s, 1H), 8.50 (s, 1H), 4.56 (m, 1H), 4.27 (m, 1H), 4.13 (m, 2H), 2.88 (m, 1H), 2.75 (m, 1H), 2.33 (m, 2H), 1.99 (d, 1H), 1.84 (m, 1H), 1.53 (m, 2H), 1.32 (m, 1H), 1.20 (m, 1H), 1.07 (m, 1H).

Example 80: Preparation of (2R,3S)-2-(3-(1H-benzo[d]imidazol-1-yl)-2-hydroxy-2-methylpropyl)piperidin-3-ol

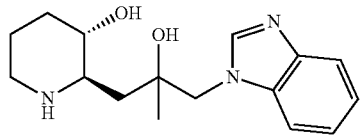 [SMILES: CC(O)(C[C@H]1NCCC[C@@H]1O)Cn1cnc2ccccc21]

(Step 80-1) Benzyl (2R,3S)-2-(3-(1H-benzo[d]imidazol-1-yl)-2-hydroxy-2-methylpropyl)-3-(tert-butyldimethylsilyloxy)piperidin-1-carboxylate Methyl magnesium bromide (420 μL, 0.42 mmol) was dissolved in tetrahydrofuran (2 mL) and cooled to 0° C. Benzyl (2R,3S)-2-(3-(1H-benzo[d]imidazol-1-yl)-2-oxopropyl)-3-(tert-butyldimethylsilyloxy)piperidin-1-carboxylate (89 mg, 0.17 mmol) was dissolved in tetrahydrofuran (1 mL) to which the above solution was slowly added dropwise. After raising the reaction temperature to room temperature, the mixture was stirred for 3 hours. When the reaction was completed, it was terminated with saturated ammonium chloride solution and extracted with ethyl acetate. The extract was dried over magnesium sulfate, filtered and concentrated under reduced pressure, and then purified by column chromatography (ethyl acetate) to obtain the title compound (42 mg, yield: 46%).

(Step 80-2) Preparation of (2R,3S)-2-(3-(1H-benzo[d]imidazol-1-yl)-2-hydroxy-2-methylpropyl)piperidin-3-ol The reaction was carried out in the same manner as in Step 1-2 of Example 1, using benzyl (2R,3S)-2-(3-(1H-benzo[d]imidazol-1-yl)-2-hydroxy-2-methylpropyl)-3-(tert-butyldimethylsilyloxy)piperidin-1-carboxylate obtained from Step 80-1, thereby obtaining the title compound (15 mg, yield: 68%).

$^1$H-NMR (500 MHz, DMSO-$d_6$): δ 8.14 (s, 1H), 7.75 (s, 1H), 7.48 (dd, 1H), 7.29 (m, 6H), 5.34 (t, 1H), 5.18-5.00 (m, 2H), 4.61 (t, 1H), 3.95 (m, 1H), 3.79 (dd, 1H), 3.12 (dd, 1H), 2.96-2.85 (m, 2H), 1.78 (m, 2H), 1.52 (d, 1H), 1.37 (m, 1H), 0.82 (d, 9H), 0.02 (m, 6H).

Example 81: Preparation of (2R,3S)-2-(3-(5,6-dichloro-1H-benzo[d]imidazol-1-yl)-2-fluoropropyl)piperidin-3-ol

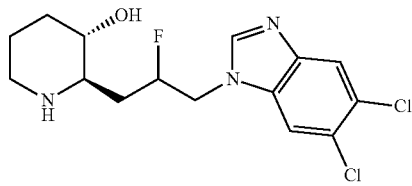 [SMILES: O[C@H]1CCCN[C@@H]1CC(F)Cn1cnc2cc(Cl)c(Cl)cc21]

(Step 81-1) Preparation of benzyl (2R,3S)-3-(tert-butyldimethylsilyloxy)-2-(3-(5,6-dichloro-1H-benzo[d]imidazol-1-yl)-2-fluoropropyl)piperidin-1-carboxylate Benzyl (2R,3S)-3-(tert-butyldimethylsilyloxy)-2-(3-(5,6-dichloro-1H-benzo[d]imidazol-1-yl)-2-hydroxypropyl)piperidin-1-carboxylate (73 mg, 0.12 mmol) obtained from Step 70-1 of Example 70 was dissolved in dichloromethane (1 mL) and cooled to −78° C. Diethylaminotrifluoromethyl sulfide (16 μL, 0.12 mmol) dissolved in dichloromethane (1 mL) was slowly added dropwise thereto, and the mixture was stirred at −78° C. for 30 minutes. When the reaction is completed, it was terminated with saturated sodium hydrogen carbonate solution, and extracted with dichloromethane. The extract was dried over magnesium sulfate, filtered and concentrated under reduced pressure and then purified by column chromatography (ethyl acetate) to obtain the title compound (51 mg, yield: 69%).

(Step 81-2) Preparation of (2R,3S)-2-(3-(5,6-dichloro-1H-benzo[d]imidazol-1-yl)-2-fluoropropyl)piperidin-3-ol The reaction was carried out in the same manner as in Step 1-2 of Example 1, using benzyl (2R,3S)-3-(tert-butyldimethylsilyloxy)-2-(3-(5,6-dichloro-1H-benzo[d]imidazol-1-yl)-2-fluoropropyl)piperidin-1-carboxylate obtained from Step 80-1, thereby obtaining the title compound (24 mg, yield: 64%).

$^1$H-NMR (500 MHz, DMSO-$d_6$): δ 8.29 (s, 1H), 8.09 (s, 1H), 7.93 (s, 1H), 4.57-4.52 (m, 2H), 4.47-4.43 (m, 1H), 4.04 (dd, 1H), 3.29 (m, 1H), 3.15-3.13 (m, 1H), 2.94-2.92 (m, 1H), 1.83-1.82 (m, 1H), 1.59-1.54 (m, 2H), 1.37-1.26 (m, 3H).

Example 82: Preparation of (2R,3S)-2-(3-(5,6-dichloro-1H-benzo[d]imidazol-1-yl)-2,2-difluoropropyl)piperidin-3-ol

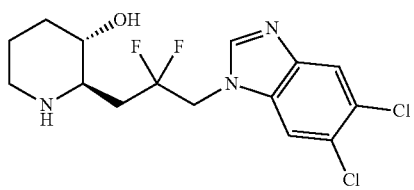 [SMILES: O[C@H]1CCCN[C@@H]1CC(F)(F)Cn1cnc2cc(Cl)c(Cl)cc21]

(Step 82-1) Preparation of benzyl (2R,3S)-3-(tert-butyldimethylsilyloxy)-2-(3-(5,6-dichloro-1H-benzo[d]imidazol-1-yl)-2,2-difluoropropyl)piperidin-1-carboxylate Benzyl (2R,3S)-3-(tert-butyldimethylsilyloxy)-2-(3-(5,6-dichloro-1H-benzo[d]imidazol-1-yl)-2-oxopropyl)piperidin-1-carboxylate (100 mg, 0.17 mmol) was dissolved in dichloromethane (5 mL) and cooled to −78° C. to which diethylaminotrifluoromethyl sulfide (67 μL, 0.51 mmol) was slowly added dropwise. After raising the reaction temperature to room temperature, the mixture was stirred for 12 hours. When the reaction was completed, it was terminated with saturated sodium hydrogen carbonate solution and extracted with dichloromethane. The extract was dried over magnesium sulfate, filtered and concentrated under reduced pressure, and then purified by column chromatography (ethyl acetate:hexane=2:1) to obtain the title compound (42 mg, yield: 41%).

(Step 82-2) Preparation of (2R,3S)-2-(3-(5,6-dichloro-1H-benzo[d]imidazol-1-yl)-2,2-difluoropropyl)piperidin-3-ol The reaction was carried out in the same manner as in Step 1-2 of Example 1, using benzyl (2R,3S)-3-(tert-butyldimethylsilyloxy)-2-(3-(5,6-dichloro-1H-benzo[d]imidazol-1-yl)-2,2-difluoropropyl)piperidin-1-carboxylate obtained from Step 82-1, thereby obtaining the title compound (17 mg, yield: 68%).

$^1$H-NMR (500 MHz, DMSO-$d_6$): δ 8.32 (s, 1H), 7.98 (s, 1H), 7.94 (s, 1H), 4.95-4.83 (m, 2H), 4.74-4.73 (dd, 1H), 2.92-2.89 (m, 1H), 2.81-2.79 (m, 1H), 2.62-2.59 (m, 1H), 2.37-2.33 (m, 1H), 1.84-1.80 (m, 1H), 1.77-1.75 (m, 1H), 1.56-1.54 (m, 1H), 1.34-1.29 (m, 1H), 1.24-1.19 (m, 1H).

Example 83: Preparation of (2R,3S)-2-(3-(5,6-dichloro-1H-benzo[d]imidazol-1-yl)-2-methoxypropyl)piperidin-3-ol

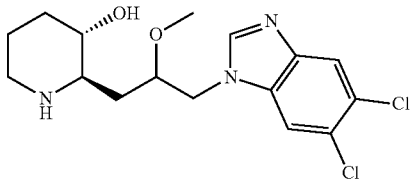 [SMILES: COC(C[C@H]1NCCC[C@@H]1O)Cn1cnc2cc(Cl)c(Cl)cc21]

(Step 83-1) Preparation of benzyl (2R,3S)-3-(tert-butyldimethylsilyloxy)-2-(3-(5,6-dichloro-1H-benzo[d]imidazol-1-yl)-2-hydroxypropyl)piperidin-1-carboxylate Benzyl (2R,3S)-3-(tert-butyldimethylsilyloxy)-2-(3-(5,6-dichloro-1H-benzo[d]imidazol-1-yl)-2-oxopropyl)piperidin-1-carboxylate (200 mg, 0.34 mmol) was dissolved in methanol (1 mL) and then cooled to 0° C. Sodium borohydride (39 mg, 1.0 mmol) was slowly added thereto. After raising the reaction temperature to room temperature, the mixture was stirred for 1 hour. When the reaction was completed, it was terminated with water and extracted with ethyl acetate. The extract was dried over magnesium sulfate, filtered and concentrated under reduced pressure, and then purified by column chromatography (ethyl acetate) to obtain the title compound (180 mg, yield: 90%).

(Step 83-2) Preparation of benzyl (2R,3S)-3-(tert-butyldimethylsilyloxy)-2-(3-(5,6-dichloro-1H-benzo[d]imidazol-1-yl)-2-methoxypropyl)piperidin-1-carboxylate Benzyl (2R,3S)-3-(tert-butyldimethylsilyloxy)-2-(3-(5,6-dichloro-1H-benzo[d]imidazol-1-yl)-2-hydroxypropyl)piperidin-1-carboxylate (100 mg, 0.17 mmol) obtained from Step 83-1 was dissolved in tetrahydrofuran (2 mL) and then cooled to 0° C. Sodium borohydride (39 mg, 1.0 mmol) and methyl iodide (16 μL, 0.25 mmol) were sequentially added slowly thereto. After raising the reaction temperature to room temperature, the mixture was stirred for 3 hour. When the reaction was completed, it was terminated with water and extracted with ethyl acetate. The extract was dried over magnesium sulfate, filtered and concentrated under reduced pressure, and then purified by column chromatography (ethyl acetate 100%) to obtain the title compound (80 mg, yield: 78%).

(Step 83-3) Preparation of (2R,3S)-2-(3-(5,6-dichloro-1H-benzo[d]imidazol-1-yl)-2-methoxypropyl)piperidin-1-carboxylate Benzyl (2R,3S)-3-(tert-butyldimethylsilyloxy)-2-(3-(5,6-dichloro-1H-benzo[d]imidazol-1-yl)-2-methoxypropyl)piperidin-1-carboxylate (50 mg, 0.08 mmol) obtained from Step 83-2 was completely dissolved in 6N hydrochloric acid solution (4 mL) and then stirred at 100° C. for 1 hour. When the reaction was completed, the mixture was cooled up to room temperature, and then adjusted to pH 9 by adding potassium carbonate. The resultant product was diluted with an excess of water and extracted with chloroform. The extract was dried over magnesium sulfate, filtered and concentrated under reduced pressure, and then recrystallized with diethyl ether to obtain the title compound (22 mg, yield: 75%).

¹H-NMR (500 MHz, DMSO-d₆): δ 8.05 (s, 1H), 7.90 (s, 1H), 7.47 (s, 1H), 4.60-4.58 (m, 1H), 4.41-4.31 (m, 2H), 3.41 (s, 3H), 3.29 (m, 1H), 3.05-3.01 (m, 1H), 2.64-2.61 (m, 1H), 2.49-2.46 (m, 1H), 2.24-2.20 (m, 1H), 1.48-1.44 (m, 2H), 1.33-1.25 (m, 2H).

Example 84: Preparation of (2R,3S)-2-(3-(5,6-dichloro-1H-benzo[d]imidazol-1-yl)-2-hydroxy-2-methylpropyl)piperidin-3-ol

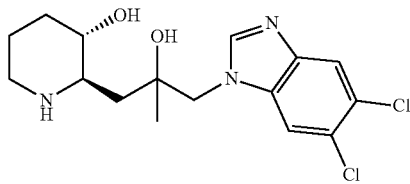 [SMILES: CC(O)(C[C@H]1NCCC[C@@H]1O)Cn1cnc2cc(Cl)c(Cl)cc21]

The reaction was carried out in the same manner as in Step 80-1 and Step 80-2 of Example 80, except that benzyl (2R,3S)-3-(tert-butyldimethylsilyloxy)-2-(3-(5,6-dichloro-1H-benzo[d]imidazol-1-yl)-2-oxopropyl)piperidin-1-carboxylate was used instead of benzyl (2R,3S)-2-(3-(1H-benzo[d]imidazol-1-yl)-2-oxopropyl)-3-(tert-butyldimethylsilyloxy)piperidin-1-carboxylate, thereby obtaining the title compound (22 mg, yield: 71%).

¹H-NMR (500 MHz, CDCl₃-d): δ 8.26 (s, 1H), 8.02 (s, 1H), 7.89 (s, 1H), 4.24 (s, 2H), 2.93 (m, 1H), 2.79-2.77 (m, 1H), 2.38-2.34 (m, 1H), 2.05-1.99 (m, 2H), 1.89-1.87 (m, 1H), 1.58-1.55 (m, 1H), 1.32-1.27 (m, 3H), 0.90 (s, 3H).

Example 85: Preparation of (2R,3S)-2-(2-((5-bromo-4-methyl-1H-benzo[d]imidazol-1-yl)methyl)-3,3,3-trifluoro-2-hydroxypropyl)piperidin-3-ol

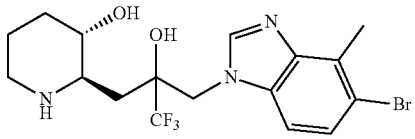 [SMILES: Cc1c(Br)ccc2c1ncn2CC(O)(C[C@H]1NCCC[C@@H]1O)C(F)(F)F]

(Step 85-1) Preparation of benzyl (2R,3S)-2-(2-((5-bromo-4-methyl-1H-benzo[d]imidazol-1-yl)methyl)-3,3,3-trifluoro-2-hydroxypropyl)-3-(tert-butyldimethylsilyloxy)piperidin-1-carboxylate Benzyl (2R,3S)-2-(3-(5-bromo-4-methyl-1H-benzo[d]imidazol-1-yl)-2-oxopropyl)-3-(tert-butyldimethylsilyloxy)piperidin-1-carboxylate (100 mg, 0.16 mmol) was dissolved in tetrahydrofuran (5 mL) to which trimethyl(trifluoromethyl)silane (36 mL, 0.24 mmol) was added at 0° C., followed by slowly adding tertbutylammonium fluoride (190 ml, 0.19 mmol). The mixture was stirred at room temperature for 18 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (dichloromethane:methanol=10:1) to obtain the title compound (61 mg, yield: 55%).

(Step 85-2) Preparation of (2R,3S)-2-(2-((5-bromo-4-methyl-1H-benzo[d]imidazol-1-yl)methyl)-3,3,3-trifluoro-2-hydroxypropyl)piperidin-3-ol Benzyl (2R,3S)-2-(2-((5-bromo-4-methyl-1H-benzo[d]imidazol-1-yl)methyl)-3,3,3-trifluoro-2-hydroxypropyl)-3-(tert-butyldimethylsilyloxy)piperidin-1-carboxylate (60 mg, 0.09 mmol) obtained from Step 85-1 was dissolved in 6N hydrochloric acid solution (3 mL) and then stirred under reflux for 1 hour. When the reaction was completed, the reaction solution was cooled to 0° C., neutralized (pH 7) with potassium carbonate, and extracted with a mixed solution of chloroform and a small amount of acetone. The organic layer was collected, dried over magnesium sulfate, filtered and concentrated under reduced pressure, and then recrystallized with diethyl ether to obtain the title compound (27 mg, yield: 70%).

¹H-NMR (500 MHz, DMSO-d₆): δ 8.97 (s, 1H), 8.24 (d, 1H), 8.20 (d, 1H), 5.59 (s, 1H), 5.20 (dd, 2H), 3.64 (m, 1H), 3.60 (d, 1H), 3.48 (d, 1H), 3.38 (s, 3H), 3.01 (d, 2H), 2.26 (m, 1H), 2.28 (d, 1H), 2.01 (m, 2H), 1.92 (m, 1H).

Example 86: Preparation of (2R,3S)-2-(3-(5,6-dichloro-1H-benzo[d]imidazol-1-yl)-2-(methylamino)propyl)piperidin-3-ol

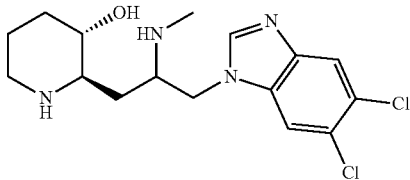 [SMILES: CNC(C[C@H]1NCCC[C@@H]1O)Cn1cnc2cc(Cl)c(Cl)cc21]

1-(5,6-dichloro-1H-benzo[d]imidazol-1-yl)-3-((2R,3S)-3-hydroxypiperidin-2-yl)propan-2-one (20 mg, 0.06 mmol) was dissolved in ethanol (2 mL) to which methylamine hydrochloride (19 mg, 0.29 mmol), titanium(IV) isopropoxide (86 μL, 0.29 mmol) and triethylamine (41 μL, 0.29 mmol) were added and then stirred at room temperature for 8 hours. Sodium borohydride (8 mg, 0.22 mmol) was added thereto and the mixture was further stirred at room temperature in 8 hours. When the reaction was completed, the reaction solution was filtered through celite. The filtrate was concentrated under reduced pressure to remove the solvent, diluted with ethyl acetate and washed with saturated sodium chloride solution. The organic layers were collected, dried over sodium sulfate, filtered, and concentrated under reduced pressure. The concentrate was recrystallized with diethyl ether to obtain the title compound (5 mg, yield: 10%).

¹H-NMR (500 MHz, DMSO-d₆): δ 8.03 (s, 1H), 7.88 (s, 1H), 7.50 (s, 1H), 4.60 (m, 1H), 4.31 (m, 2H), 3.27 (s, 3H), 3.22 (m, 1H), 3.01 (m, 1H), 2.77 (m, 2H), 2.45 (m, 1H), 2.18 (m, 1H), 1.45 (m, 2H), 1.25 (m, 2H).

Example 87: Preparation of 1-(5,6-dichloro-2-(hydroxymethyl)-1H-benzo[d]imidazol-1-yl)-3-((2R,3S)-3-hydroxypiperidin-2-yl)propan-2-one

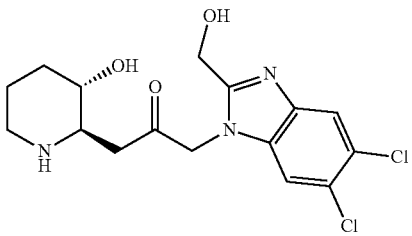 [SMILES: O=C(C[C@H]1NCCC[C@@H]1O)Cn1c(CO)nc2cc(Cl)c(Cl)cc21]

The reaction was carried out in the same manner as in Step 56-1, Step 56-2 and Step 56-3 of Example 56, except that (5,6-dichloro-1H-benzo[d]imidazol-2-yl)methanol was used instead of (1H-benzo[d]imidazol-2-yl)methanol, thereby obtaining the title compound (24 mg, yield: 78%).

$^1$H-NMR (500 MHz, DMSO-$d_6$): δ 7.87 (d, 2H), 5.37 (dd, 2H), 4.82 (d, 1H), 4.59 (s, 2H), 3.00 (m, 1H), 2.95 (dd, 1H), 2.82 (d, 1H), 2.67 (m, 1H), 2.40 (m, 2H), 1.90 (m, 1H), 1.60 (d, 1H), 1.35 (m, 1H), 1.24 (m, 1H).

Example 88: Preparation of (2R,3S)-2-(3-(5,6-dichloro-2-(hydroxymethyl)-1H-benzo[d]imidazol-1-yl)-2-hydroxypropyl)piperidin-3-ol

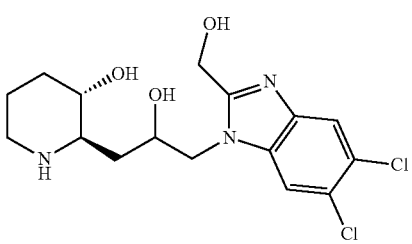 [SMILES: OCc1nc2cc(Cl)c(Cl)cc2n1CC(O)C[C@H]1NCCC[C@@H]1O]

(Step 88-1) Preparation of 2-((tert-butyldimethylsilyloxy)methyl)-5,6-dichloro-1H-benzo[d]imidazole The reaction was carried out in the same manner as in Step 56-1 of Example 56, except that (5,6-dichloro-1H-benzo[d]imidazol-2-yl)methanol was used instead of (1H-benzo[d]imidazol-2-yl)methanol, thereby obtaining the title compound (81 mg, yield: 92%).

(Step 88-2) Preparation of (2R,3S)-benzyl 3-(tert-butyldimethylsilyloxy)-2-(3-(2-((tert-butyldimethylsilyloxy)methyl)-5,6-dichloro-1H-benzo[d]imidazol-1-yl)-2-oxopropyl)piperidin-1-carboxylate 2-((tert-butyldimethylsilyloxy)methyl)-5,6-dichloro-1H-benzo[d]imidazole (75 mg, 0.23 mmol) obtained from Step 88-1 was dissolved in N,N-dimethylformamide (2 mL) to which potassium carbonate (62 mg, 0.45 mmol) was added and stirred at room temperature for 10 minutes. Then, benzyl (2R,3S)-2-(3-bromo-2-oxopropyl)-3-(tert-butyldimethylsilyloxy)piperidin-1-carboxylate (130 mg, 0.27 mmol) was added and stirred at room temperature for 3 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=3:1) to obtain the title compound (160 mg, yield: 93%).

(Step 88-3) Preparation of benzyl (2R,3S)-3-(tert-butyldimethylsilyloxy)-2-(3-(2-((tert-butyldimethylsilyloxy)methyl)-5,6-dichloro-1H-benzo[d]imidazol-1-yl)-2-hydroxypropyl)piperidin-1-carboxylate Benzyl (2R,3S)-3-(tert-butyldimethylsilyloxy)-2-(3-(2-((tert-butyldimethylsilyloxy)methyl)-5,6-dichloro-1H-benzo[d]imidazol-1-yl)-2-oxopropyl)piperidin-1-carboxylate (90 mg, 0.12 mmol) obtained from Step 88-2 was dissolved in methanol (5 mL) to which sodium borohydride (14 mg, 0.37 mmol) was added and the mixture was stirred at room temperature for 2 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=3:1) to obtain the title compound (36 mg, yield: 40%).

(Step 88-4) Preparation of (2R,3S)-2-(3-(5,6-dichloro-2-(hydroxymethyl)-1H-benzo[d]imidazol-1-yl)-2-hydroxypropyl)piperidin-3-ol The reaction was carried out in the same manner as in Step 1-2 of Example 1, except that benzyl (2R,3S)-3-(tert-butyldimethylsilyloxy)-2-(3-(2-((tert-butyldimethylsilyloxy)methyl)-5,6-dichloro-1H-benzo[d]imidazol-1-yl)-2-hydroxypropyl)piperidin-1-carboxylate obtained from Step 88-3 was used instead of benzyl (2R,3S)-2-(3-(1H-benzo[d]imidazol-1-yl)-2-oxopropyl)-3-(tert-butyldimethylsilyloxy)piperidin-1-carboxylate obtained from Step 88-3, thereby obtaining the title compound (15 mg, yield: 84%).

$^1$H-NMR (500 MHz, DMSO-$d_6$): δ 7.93 (s, 1H), 7.84 (s, 1H), 4.77 (m, 3H), 4.32 (dd, 1H), 4.18 (dd, 1H), 4.03 (m, 1H), 2.96 (m, 1H), 2.80 (d, 1H), 2.38 (dt, 1H), 2.30 (m, 1H), 1.87 (m, 2H), 1.56 (d, 1H), 1.41 (m, 1H), 1.30 (m, 1H), 1.22 (m, 1H).

Example 89: Preparation of (2R,3S)-2-(3-(5-bromo-4-methyl-1H-benzo[d]imidazol-1-yl)-2-hydroxypropyl)piperidin-3-ol

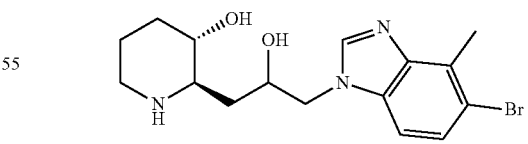

The reaction was carried out in the same manner as in Step 69-1 and Step 69-2 of Example 69, except that benzyl (2R,3S)-2-(3-(5-bromo-4-methyl-1H-benzo[d]imidazol-1-yl)-2-oxopropyl)-(tert-butyldimethylsilyloxy)piperidin-1-carboxylate was used instead of benzyl (2R,3S)-3-(tert-butyldimethylsilyloxy)-2-(3-(1H-benzo[d]imidazol-1-yl)-2-oxopropyl)piperidin-1-carboxylate, thereby obtaining the title compound (2 mg, yield: 22%).

¹H-NMR (500 MHz, DMSO-d₆): δ 8.27 (s, 1H), 8.02 (s, 1H), 7.92 (s, 1H), 4.65 (s, 1H), 4.20 (m, 2H), 2.93 (m, H), 2.78 (d, 1H), 2.37 (m, 2H), 2.09 (d, 1H), 1.86 (d, 1H) 1.79 (m, 1H), 1.55 (m, 1H), 1.38 (m, 1H), 1.20 (m, 1H).

Example 90: Preparation of (S)-1-(5,6-dichloro-1H-benzo[d]imidazol-1-yl)-3-(pyrrolidin-2-yl)propan-2-one

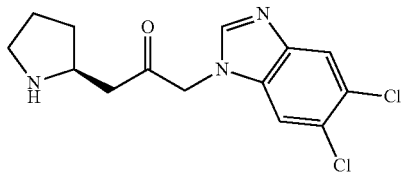 [SMILES: O=C(C[C@@H]1CCCN1)Cn1cnc2cc(Cl)c(Cl)cc21]

The reaction was carried out in the same manner as in Step 1-1 and Step 1-2 of Example 1, except that benzyl (S)-2-(3-bromo-2-oxopropyl)pyrrolidin-1-carboxylate was used instead of benzyl (2R,3S)-2-(3-bromo-2-oxopropyl)-3-(tert-butyldimethylsilyloxy)piperidin-1-carboxylate, thereby obtaining an intermediate (69 mg, yield: 77%) and the title compound (21 mg, yield: 64%) synthesized therefrom.

¹H-NMR (500 MHz, MeOH-d₄): δ 9.49 (s, 1H), 8.35 (s, 1H), 8.10 (s, 1H), 5.82 (m, 2H), 4.03-3.99 (m, 1H), 3.43-3.41 (m, 2H), 3.30-3.26 (m, 2H), 2.32-2.29 (m, 1H), 2.14-2.11 (m, 1H), 2.00-1.97 (m, 1H), 1.86-1.82 (m, 1H).

Example 91: Preparation of 1-(5-chloro-1H-pyrrolo[2,3-b]pyridin-1-yl)-3-((2R,3S)-3-hydroxypiperidin-2-yl)propan-2-one

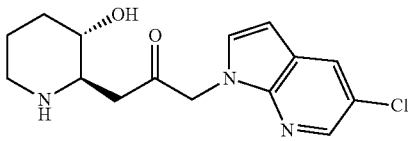 [SMILES: O=C(C[C@H]1NCCC[C@@H]1O)Cn1ccc2cc(Cl)cnc21]

The reaction was carried out in the same manner as in Step 1-1 and Step 1-2 of Example 1, except that 5-chloro-1H-pyrrolo[2,3-b]pyridine was used instead of 1H-benzo[d]imidazole, thereby obtaining the title compound (5 mg, yield: 13%).

¹H-NMR (500 MHz, DMSO-d₆): δ 8.20 (d, 1H), 8.11 (dd, 1H), 7.51 (t, 1H), 6.52 (d, 1H), 5.27 (s, 2H), 5.14 (s, 1H), 3.20 (m, 1H), 3.04 (dd, 1H), 2.93 (m, 3H), 2.59 (m, 3H), 1.90 (m, 1H), 1.68 (d, 1H), 1.47 (m, 1H), 1.32 (m, 1H).

Example 92: Preparation of 1-(6-bromo-1H-pyrrolo[2,3-b]pyridin-1-yl)-3-((2R,3S)-3-hydroxypiperidin-2-yl)propan-2-one

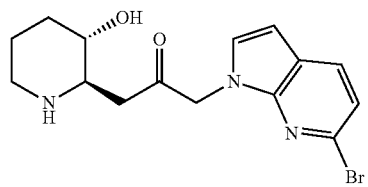 [SMILES: O=C(C[C@H]1NCCC[C@@H]1O)Cn1ccc2ccc(Br)nc21]

The reaction was carried out in the same manner as in Step 1-1 and Step 1-2 of Example 1, except that 6-bromo-1H-pyrrolo[2,3-b]pyridine was used instead of 1H-benzo[d]imidazole, thereby obtaining the title compound (11 mg, yield: 25%).

¹H-NMR (500 MHz, DMSO-d₆): δ 7.92 (d, 1H), 7.38 (d, 1H), 7.22 (d, 1H), 6.50 (d, 1H), 5.17 (d, 2H), 4.70 (d, 1H), 2.91 (m, 2H), 2.76 (m, 1H), 2.61 (m, 1H), 2.38 (m, 1H), 2.33 (m, 1H), 1.95 (m, 1H), 1.53 (m, 1H), 1.32 (m, 1H), 1.15 (m, 1H).

Example 93: Preparation of 1-(7-chloro-1H-pyrrolo[2,3-c]pyridin-1-yl)-3-((2R,3S)-3-hydroxypiperidin-2-yl)propan-2-one

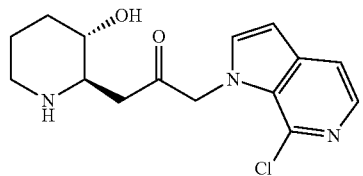 [SMILES: O=C(C[C@H]1NCCC[C@@H]1O)Cn1ccc2ccnc(Cl)c21]

The reaction was carried out in the same manner as in Step 1-1 and Step 1-2 of Example 1, except that 7-chloro-1H-pyrrolo[2,3-b]pyridine was used instead of 1H-benzo[d]imidazole, thereby obtaining the title compound (15 mg, yield: 20%).

¹H-NMR (500 MHz, DMSO-d₆): δ 7.88 (d, 1H), 7.58 (d, 1H), 7.52 (d, 1H), 6.63 (d, 1H), 5.52 (d, 2H), 4.73 (d, 1H), 3.01 (m, 2H), 2.77 (m, 1H), 2.62 (m, 1H), 2.42 (m, 1H), 2.35 (m, 1H), 1.89 (m, 1H), 1.55 (m, 1H), 1.35 (m, 1H), 1.21 (m, 1H).

Example 94: Preparation of 1-(6-bromo-1H-pyrrolo[3,2-b]pyridin-1-yl)-3-((2R,3S)-3-hydroxypiperidin-2-yl)propan-2-one

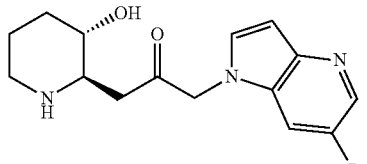

The reaction was carried out in the same manner as in Step 1-1 and Step 1-2 of Example 1, except that 6-bromo-1H-pyrrolo[2,3-b]pyridine was used instead of 1H-benzo[d]imidazole, thereby obtaining the title compound (15 mg, yield: 22%).

¹H-NMR (500 MHz, DMSO-d₆): δ 8.36 (d, 1H), 8.13 (d, 1H), 7.51 (d, 1H), 6.58 (d, 1H), 5.25 (d, 2H), 4.78 (m, 1H), 2.98 (m, 1H), 2.87 (m, 1H), 2.81 (m, 1H), 2.62 (m, 1H), 2.38 (m, 2H), 1.90 (m, 1H), 1.56 (m, 1H), 1.33 (m, 1H), 1.23 (m, 1H).

Example 95: Preparation of 1-(3-((2R,3S)-3-hydroxypiperidin-2-yl)-2-oxopropyl)-4-methyl-1H-pyrrolo[2,3-b]pyridin-5-carbonitrile

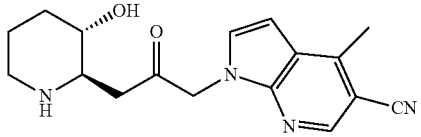 [SMILES: Cc1c(C#N)cnc2c1ccn2CC(=O)C[C@H]1NCCC[C@@H]1O]

The reaction was carried out in the same manner as in Step 1-1 and Step 1-2 of Example 1, except that 4-methyl-1H-pyrrolo[2,3-b]pyridin-5-carbonitrile was used instead of 1H-benzo[d]imidazole, thereby obtaining the title compound (29 mg, yield: 78%).

$^1$H-NMR (500 MHz, DMSO-$d_6$): δ 8.50 (s, 1H), 7.54 (d, 1H), 6.76 (d, 1H), 5.27 (d, 2H), 4.72 (d, 1H), 2.93 (m, 2H), 2.77 (m, 1H), 2.69 (s, 3H), 2.61 (m, 1H), 2.35 (m, 2H), 1.87 (d, 1H), 1.54 (d, 1H), 1.32 (d, 1H), 1.20 (m, 1H).

Example 96: Preparation of 1-(5-chloro-1H-indazol-1-yl)-3-((2R,3S)-3-hydroxypiperidin-2-yl)propan-2-one

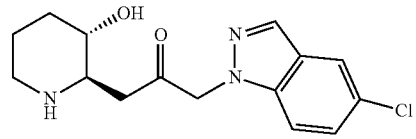 [SMILES: O=C(C[C@H]1NCCC[C@@H]1O)Cn1ncc2cc(Cl)ccc21]

The reaction was carried out in the same manner as in Step 1-1 and Step 1-2 of Example 1, except that 5-chloro-1H-indazole was used instead of 1H-benzo[d]imidazole, thereby obtaining the title compound (15 mg, yield: 29%).

$^1$H-NMR (500 MHz, DMSO-$d_6$): δ 8.08 (s, 1H), 7.86 (s, 1H), 7.60 (d, 1H), 7.39 (d, 1H), 5.55 (s, 2H), 5.40 (s, 1H), 3.03 (m, 5H), 2.66 (m, 3H), 1.88 (m, 1H), 1.73 (d, 1H), 1.53 (m, 1H), 1.34 (m, 1H).

Example 97: Preparation of 1-(4-bromo-5-methyl-1H-indazol-1-yl)-3-((2R,3S)-3-hydroxypiperidin-2-yl)propan-2-one

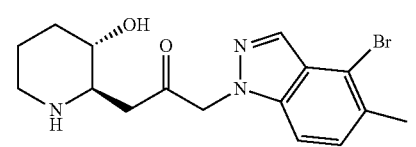 [SMILES: Cc1ccc2c(cnn2CC(=O)C[C@H]2NCCC[C@@H]2O)c1Br]

The reaction was carried out in the same manner as in Step 1-1 and Step 1-2 of Example 1, except that 4-bromo-5-methyl-1H-indazole was used instead of 1H-benzo[d]imidazole, thereby obtaining the title compound (28 mg, yield: 61%).

$^1$H-NMR (500 MHz, DMSO-$d_6$): δ 7.94 (s, 1H), 7.44 (d, 1H), 7.30 (d, 1H), 5.44 (d, 2H), 4.74 (d, 1H), 2.95-2.93 (m, 1H), 2.87 (dd, 1H), 2.84 (d, 1H), 2.53 (d, 1H), 2.39-2.28 (m, 1H), 1.96 (s, 1H), 1.85 (d, 1H), 1.53 (d, 1H), 1.33-1.28 (m, 1H), 1.19 (t, 1H).

Example 98: Preparation of 1-(5-chloro-1H-pyrazolo[3,4-b]pyridin-1-yl)-3-((2R,3S)-3-hydroxypiperidin-2-yl)propan-2-one

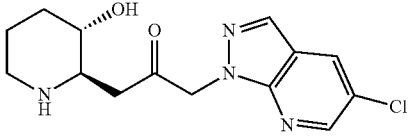 [SMILES: O=C(C[C@H]1NCCC[C@@H]1O)Cn1ncc2cc(Cl)cnc21]

The reaction was carried out in the same manner as in Step 1-1 and Step 1-2 of Example 1, except that 5-chloro-1H-pyrazolo[3,4-b]pyridine was used instead of 1H-benzo[d]imidazole, thereby obtaining the title compound (10 mg, yield: 17%).

$^1$H-NMR (500 MHz, DMSO-$d_6$): δ 8.55 (s, 1H), 8.43 (s, 1H), 8.19 (s, 1H), 5.49 (s, 2H), 3.12 (m, 1H), 2.95 (dd, 1H), 2.83 (d, 1H), 2.68 (m, 3H), 1.87 (m, 1H), 1.38 (d, 1H), 1.36 (m, 1H), 1.23 (m, 1H).

Example 99: Preparation of 1-(5-chloro-1H-benzo[d][1,2,3]triazol-1-yl)-3-((2R,3S)-3-hydroxypiperidin-2-yl)propan-2-one

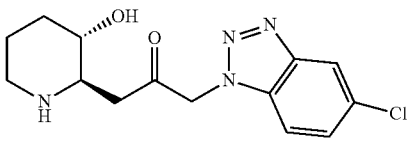 [SMILES: O=C(C[C@H]1NCCC[C@@H]1O)Cn1nnc2cc(Cl)ccc21]

The reaction was carried out in the same manner as in Step 1-1 of Example 1, except that 5-chloro-1H-benzo[d][1,2,3]triazole was used instead of 1H-benzo[d]imidazole, and then separated by column chromatography (hexane:ethyl acetate=1:1), thereby obtaining an intermediate. Subsequently, the reaction was carried out in the same manner as in Step 1-2 of Example 1, thereby obtaining the title compound (12 mg, yield: 64%).

$^1$H-NMR (500 MHz, DMSO-$d_6$): δ 8.06 (d, 1H), 7.90 (d, 1H), 7.38 (d, 1H), 5.80 (d, 2H), 4.90 (m, 1H), 3.02 (m, 1H), 2.92 (m, 1H), 2.78 (m, 1H), 2.65 (m, 1H), 2.37 (m, 1H), 2.12 (m, 1H), 1.88 (m, 1H), 1.55 (m, 1H), 1.35 (m, 1H), 1.22 (m, 1H).

Example 100: Preparation of 1-(6-chloro-1H-benzo[d][1,2,3]triazol-1-yl)-3-((2R,3S)-3-hydroxypiperidin-2-yl)propan-2-one

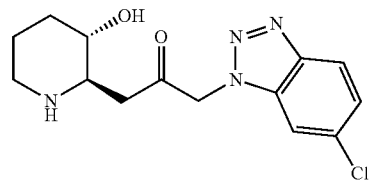 [SMILES: O=C(C[C@H]1NCCC[C@@H]1O)Cn1nnc2ccc(Cl)cc21]

The reaction was carried out in the same manner as in Step 1-1 of Example 1, except that 5-chloro-1H-benzo[d][1,2,3]triazole was used instead of 1H-benzo[d]imidazole, and then separated by column chromatography (hexane:

ethyl acetate=1:1), thereby obtaining an intermediate. Subsequently, the reaction was carried out in the same manner as in Step 1-2 of Example 1, thereby obtaining the title compound (10 mg, yield: 69%).

$^1$H-NMR (500 MHz, DMSO-$d_6$): δ 8.15 (s, 1H), 7.71 (d, 1H), 7.53 (d, 1H), 5.84 (s, 2H), 4.85 (m, 1H), 3.05 (m, 1H), 2.97 (m, 1H), 2.77 (m, 1H), 2.65 (m, 1H), 2.37 (m, 1H), 2.02 (m, 1H), 1.88 (m, 1H), 1.50 (m, 1H), 1.31 (m, 1H), 1.17 (m, 1H).

Experimental Example 1: In Vitro PRS Enzyme Activity Inhibition Experiment

In order to confirm the biological activities of the compounds prepared in Examples, % inhibition or $IC_{50}$ values of PRS enzyme (phosphoribosylpyrophosphate synthetase enzyme) activities were calculated.

Specifically, the portion corresponding to PRS in cDNA of EPRS was subcloned, and the obtained high-purity PRS protein was purified and used in the experiment. The compounds (1 μM) prepared in Examples were added into the reaction buffer (20 mM $KPO_4$ (pH 7.4), 6 mM MgAc, 5 mM ATP, 400 mg/mL tRNA, 0.5 mM DTT, 20 mCi[$^3$H]proline (1 mCi/mL)) and allowed to react at 37° C. for 5 to 10 minutes. The reaction was terminated with 3M paper that was previously dried by addition of 5% TCA. The radioactivity was measured using a liquid scintillation counter.

$IC_{50}$ values of the respective compounds were calculated and analyzed using Microsoft Excel or Sigma Plot 8.0. The results are shown in Table 1 below. In Table 1, the results are divided into A, B and C according to the range of $IC_{50}$. The case where the derived $IC_{50}$ is 100 nM or less is represented by "A", the case where the $IC_{50}$ is 100 to 500 nM is represented by "B", and the case where the $IC_{50}$ is 500 nM or higher is represented by "C".

TABLE 1

| Example No. | PRS $IC_{50}$ |
| --- | --- |
| 1 | C |
| 2 | A |
| 3 | A |
| 4 | A |
| 5 | A |
| 6 | B |
| 7 | A |
| 8 | A |
| 9 | A |
| 10 | B |
| 11 | B |
| 12 | A |
| 13 | A |
| 14 | A |
| 15 | A |
| 16 | A |
| 17 | A |
| 18 | A |
| 19 | A |
| 20 | A |
| 21 | B |
| 22 | A |
| 23 | A |
| 24 | A |
| 25 | A |
| 26 | A |
| 27 | A |
| 28 | A |
| 29 | C |
| 30 | C |
| 31 | C |
| 32 | B |

TABLE 1-continued

| Example No. | PRS $IC_{50}$ |
| --- | --- |
| 33 | A |
| 34 | B |
| 35 | A |
| 36 | A |
| 37 | A |
| 38 | B |
| 39 | A |
| 40 | A |
| 41 | A |
| 42 | A |
| 43 | C |
| 44 | C |
| 45 | B |
| 46 | A |
| 47 | C |
| 48 | C |
| 49 | C |
| 50 | C |
| 51 | C |
| 52 | C |
| 53 | C |
| 54 | C |
| 55 | C |
| 56 | A |
| 57 | B |
| 58 | A |
| 59 | A |
| 60 | C |
| 61 | C |
| 62 | C |
| 63 | C |
| 64 | C |
| 65 | C |
| 66 | C |
| 67 | C |
| 68 | B |
| 69 | C |
| 70 | B |
| 71 | A |
| 72 | C |
| 73 | C |
| 74 | C |
| 75 | C |
| 76 | C |
| 77 | C |
| 78 | A |
| 79 | B |
| 80 | C |
| 81 | C |
| 82 | C |
| 83 | C |
| 84 | C |
| 85 | C |
| 86 | C |
| 87 | A |
| 88 | B |
| 89 | A |
| 90 | C |
| 91 | B |
| 92 | C |
| 93 | B |
| 94 | C |
| 95 | C |
| 96 | C |
| 97 | B |
| 98 | C |
| 99 | B |
| 100 | C |

Experimental Example 2: Cancer Cell Growth Inhibition Experiment

NCI-H460 cells, lung cancer cell lines, were cultured in 5% $CO_2$, 37° C. incubator using a flask for 75 cm$^2$ tissue culture. 96-well plates were used for the evaluation. These were prepared by differently applying at concentrations in the range of 6,000 to 12,000 cells/well according to the growth rate of the cell lines. The medium containing 5% FBS were dispensed in 200 μL/well and used. The medium were cultured for 24 hours. After confirming the cell status and dispensing form of a 96-well plate under a microscope, they were used for subsequent experiments. The compounds were evaluated at concentrations of 100, 30, 10, 3, 1, 0.3, 0.03, 0.01 μM. After removing the existing medium, the compounds with various concentrations were treated in an amount of 200 μL/well. The compounds-treated plates were further cultured for 48 hours, and the cell viabilities were measured by MTT assay to calculate $IC_{50}$ values.

% Inhibition and $IC_{50}$ values of the respective compounds were calculated and analyzed using Sigma Plot 8.0. The results are represented by A, B and C in Table 2 below. The case where the derived $IC_{50}$ is 5 μM or less is represented by "A", the case where the $IC_{50}$ is 5 to 30 μM is represented by "B", and the case where the $IC_{50}$ is 30 μM or higher is represented by "C".

TABLE 2

| Example No. | NCI-H460 $IC_{50}$ |
| --- | --- |
| 1 | C |
| 2 | B |
| 3 | B |
| 4 | B |
| 5 | B |
| 6 | C |
| 7 | B |
| 8 | B |
| 9 | C |
| 10 | B |
| 11 | B |
| 12 | A |
| 13 | A |
| 14 | A |
| 15 | A |
| 16 | B |
| 17 | B |
| 18 | B |
| 19 | B |
| 20 | A |
| 21 | B |
| 22 | A |
| 23 | B |
| 24 | B |
| 25 | A |
| 26 | A |
| 27 | B |
| 28 | C |
| 30 | C |
| 32 | C |
| 33 | B |
| 35 | B |
| 36 | B |
| 37 | A |
| 38 | C |
| 39 | A |
| 40 | A |
| 42 | A |
| 46 | C |
| 48 | C |
| 50 | C |
| 51 | C |
| 52 | C |
| 56 | C |
| 57 | B |
| 58 | B |
| 59 | B |
| 60 | C |
| 61 | C |
| 62 | C |
| 69 | C |

TABLE 2-continued

| Example No. | NCI-H460 $IC_{50}$ |
| --- | --- |
| 70 | B |
| 71 | B |
| 78 | C |
| 80 | C |
| 81 | C |
| 82 | C |
| 83 | C |
| 84 | C |
| 87 | A |
| 88 | C |
| 89 | C |
| 90 | C |
| 92 | C |
| 93 | C |
| 94 | C |
| 95 | C |
| 99 | C |
| 100 | C |

Experimental Example 3: Therapeutic Effect Against Cardiac Fibrosis in a Mouse Model Model of cardiac fibrosis used Transverse Aorta Constriction (TAC) method. The right innominate artery and the left carotid artery of C57BL/6 mice (n=8-10) were subjected to a partial ligation, thereby inducing the left ventricular hypertrophy and fibrosis due to the pressure overload. All medications were orally administered at 10 mg/kg one a day for two weeks following TAC induction. Numbers of local lytic and necrotic cardiac muscle fibers per unit numbers of myofibers of the left ventricle of mouse were measured after H&E staining with histopathological image analysis techniques at the finish time of the experiment, thereby assessing the degree of damage to the cardiac muscle (FIG. 1). The percentages of collagen fibers per unit area of mouse were measured after Sirius red staining, thereby assessing the degree of perivascular localized fibrosis (FIGS. 2 and 3). In addition, mRNA of the heart tissue was extracted at the finish time of the experiment, and mRNA expression level of mouse transforming growth factor-beta1 (TGF-ß1), a fibrous factor, was measured (FIG. 4).

The invention claimed is:
1. A compound represented by the following Chemical Formula 1, or a pharmaceutically acceptable salt thereof:

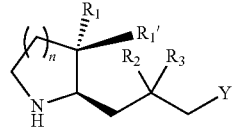

[Chemical Formula 1]

in Chemical Formula 1,
n is 1, or 2,
$R_1$ is hydrogen, or hydroxy,
$R_1'$ is hydrogen,
$R_2$ is hydroxy, halogen, amino, $C_{1-4}$ alkylamino, di($C_{1-4}$ alkyl)amino or $C_{1-4}$ alkoxy; $R_3$ is hydrogen, halogen, $C_{1-4}$ alkyl, or $C_{1-4}$ haloalkyl; or $R_2$ and $R_3$ together form an oxo (=O), hydroxyimino (=N—OH), or $C_{1-4}$ alkoxyimino (=N—O—($C_{1-4}$ alkyl));

Y is

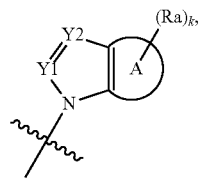

Y1 is N, CH, or CR$_4$,
wherein R$_4$ is C$_{1-4}$ alkyl, C$_{1-4}$ hydroxyalkyl, C$_{1-4}$ alkyl substituted with C$_{1-4}$ alkoxy, C$_{1-4}$ haloalkyl, or —(CH$_2$)$_m$ NR$_9$R$_{10}$, wherein m is an integer of 1 to 4, and R$_9$ and R$_{10}$ are each independently hydrogen, or C$_{1-4}$ alkyl,
Y2 is N, or CH,
A is benzene, heteroaryl having 1 to 4 nitrogen atoms, or cyclohexene, as a six-membered ring,
k is an integer of 0 to 4, and
each of Ra is independently C$_{1-4}$ alkyl, C$_{1-4}$ alkoxy, C$_{1-4}$ haloalkyl, C$_{1-4}$ haloalkoxy, halogen, cyano, or carboxy.

2. The compound or a pharmaceutically acceptable salt thereof according to claim 1, wherein R$_2$ is hydroxy, fluoro, amino, methylamino, dimethylamino or methoxy; R$_3$ is hydrogen, fluoro, methyl, or trifluoromethyl; or R$_2$ and R$_3$ together form oxo (=O), hydroxyimino (=N—OH), or methoxyimino (=N—OCH$_3$).

3. The compound or a pharmaceutically acceptable salt thereof according to claim 1, wherein A is benzene, pyridine, pyrimidine, or cyclohexene.

4. The compound or a pharmaceutically acceptable salt thereof according to claim 1, wherein R$_4$ is methyl, ethyl, hydroxymethyl, hydroxyethyl, 1-hydroxyethyl, trifluoromethyl, methoxymethyl, aminomethyl, or (dimethylamino)methyl.

5. The compound or a pharmaceutically acceptable salt thereof according to claim 1, wherein
Y is

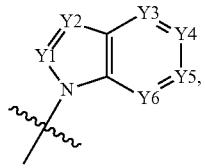

Y3 is N, or C—R$_5$;
Y4 is N, or C—R$_6$;
Y5 is N, or C—R$_7$;
Y6 is N, or C—R$_8$,
R$_5$ is hydrogen, C$_{1-4}$ alkyl, C$_{1-4}$ haloalkyl, or halogen;
R$_6$ is hydrogen, C$_{1-4}$ alkyl, C$_{1-4}$ alkoxy, C$_{1-4}$ haloalkyl, C$_{1-4}$ haloalkoxy, halogen, cyano, or carboxy;
R$_7$ is hydrogen, C$_{1-4}$ alkyl, C$_{1-4}$ alkoxy, C$_{1-4}$ haloalkyl, C$_{1-4}$ haloalkoxy, halogen, or cyano; and
R$_8$ is hydrogen, C$_{1-4}$ alkyl, C$_{1-4}$ haloalkyl, C$_{1-4}$ haloalkoxy, or halogen.

6. The compound or a pharmaceutically acceptable salt thereof according to claim 5, wherein
R$_5$ is hydrogen, methyl, trifluoromethyl, fluoro, chloro, or bromo;
R$_6$ is hydrogen, methyl, trifluoromethyl, trifluoromethoxy, fluoro, chloro, bromo, cyano, or carboxy;
R$_7$ is hydrogen, methyl, trifluoromethyl, fluoro, chloro, or bromo; and
R$_8$ is hydrogen, methyl, trifluoromethyl, trifluoromethoxy, chloro, or bromo.

7. The compound or a pharmaceutically acceptable salt thereof according to claim 1, wherein

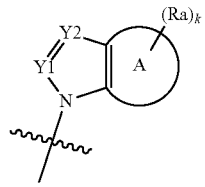

is selected from the group consisting of

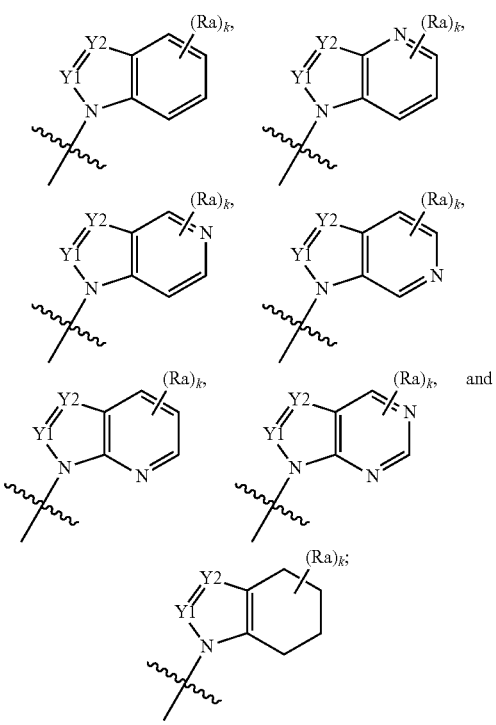

and k is an integer of 0 to 2.

8. The compound or a pharmaceutically acceptable salt thereof according to claim 7, wherein each of Ra is independently C$_{1-4}$ alkyl, C$_{1-4}$ haloalkyl, C$_{1-4}$ haloalkoxy, halogen, cyano, or carboxy.

9. The compound or a pharmaceutically acceptable salt thereof according to claim 8, wherein each of Ra is independently methyl, trifluoromethyl, trifluoromethoxy, fluoro, chloro, bromo, cyano, or carboxy.

10. The compound or a pharmaceutically acceptable salt thereof according to claim 1, wherein
n is an integer of 1 or 2,
R$_1$ is hydrogen or hydroxy,
R$_1$' is hydrogen,
R$_2$ is hydroxy, halogen, C$_{1-4}$ alkylamino, or C$_{1-4}$ alkoxy;
R$_3$ is hydrogen, halogen, C$_{1-4}$ alkyl, or C$_{1-4}$ haloalkyl; or
R$_2$ and R$_3$ together form an oxo (=O), hydroxyimino (=N—OH), or C$_{1-4}$ alkoxyimino (=N—O—(C$_{1-4}$ alkyl));

Y is

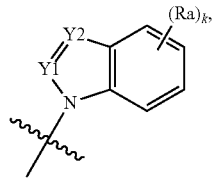

Y1 is CH, or CR$_4$,
wherein R$_4$ is C$_{1-4}$ alkyl, C$_{1-4}$ hydroxyalkyl, C$_{1-4}$ alkyl substituted with C$_{1-4}$ alkoxy, C$_{1-4}$ haloalkyl, C$_{1-4}$ alkyl substituted with amino, or C$_{1-4}$ alkyl substituted with di(C$_{1-4}$ alkyl)amino,
Y2 is N,
k is an integer of 0 to 2, and
each of Ra is independently C$_{1-4}$ alkyl, C$_{1-4}$ haloalkyl, C$_{1-4}$ haloalkoxy, or halogen.

11. The compound or a pharmaceutically acceptable salt thereof according to claim 1, wherein
n is 2,
R$_1$ is hydroxy,
R$_1$' is hydrogen,
R$_2$ is hydroxy; R$_3$ is hydrogen; or R$_2$ and R$_3$ together form an oxo (=O);
Y is

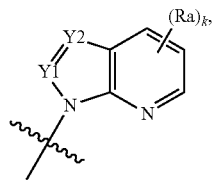

Y1 is CH,
Y2 is N,
k is an integer of 0 to 2,
each of Ra is independently C$_{1-4}$ alkyl, C$_{1-4}$ haloalkyl, halogen, or cyano.

12. The compound or a pharmaceutically acceptable salt thereof according to claim 1, wherein the compound represented by Chemical Formula 1 is any one selected from the group consisting of:
1) 1-(1H-benzo[d]imidazol-1-yl)-3-((2R,3S)-3-hydroxypiperidin-2-yl)propan-2-one,
2) 1-(5-chloro-1H-benzo[d]imidazol-1-yl)-3-((2R,3S)-3-hydroxypiperidin-2-yl)propan-2-one,
3) 1-(6-chloro-1H-benzo[d]imidazol-1-yl)-3-((2R,3S)-3-hydroxypiperidin-2-yl)propan-2-one,
4) 1-(5-bromo-1H-benzo[d]imidazol-1-yl)-3-((2R,3S)-3-hydroxypiperidin-2-yl)propan-2-one,
5) 1-(6-bromo-1H-benzo[d]imidazol-1-yl)-3-((2R,3S)-3-hydroxypiperidin-2-yl)propan-2-one,
6) 1-((2R,3S)-3-hydroxypiperidin-2-yl)-3-(5-(trifluoromethyl)-1H-benzo[d]imidazol-1-yl)propan-2-one,
7) 1-((2R,3S)-3-hydroxypiperidin-2-yl)-3-(6-(trifluoromethyl)-1H-benzo[d]imidazol-1-yl)propan-2-one,
8) 1-((2R,3S)-3-hydroxypiperidin-2-yl)-3-(7-(trifluoromethyl)-1H-benzo[d]imidazol-1-yl)propan-2-one,
9) 1-(5,6-dimethyl-1H-benzo[d]imidazol-1-yl)-3-((2R,3S)-3-hydroxypiperidin-2-yl)propan-2-one,
10) 1-(5,6-difluoro-1H-benzo[d]imidazol-1-yl)-3-((2R,3S)-3-hydroxypiperidin-2-yl)propan-2-one,
11) 1-(4,5-difluoro-1H-benzo[d]imidazol-1-yl)-3-((2R,3S)-3-hydroxypiperidin-2-yl)propan-2-one,
12) 1-(4,5-dichloro-1H-benzo[d]imidazol-1-yl)-3-((2R,3S)-3-hydroxypiperidin-2-yl)propan-2-one,
13) 1-(5-fluoro-4-methyl-1H-benzo[d]imidazol-1-yl)-3-((2R,3S)-3-hydroxypiperidin-2-yl)propan-2-one,
14) 1-(5-chloro-4-methyl-1H-benzo[d]imidazol-1-yl)-3-((2R,3S)-3-hydroxypiperidin-2-yl)propan-2-one,
15) 1-(5-bromo-4-methyl-1H-benzo[d]imidazol-1-yl)-3-((2R,3S)-3-hydroxypiperidin-2-yl)propan-2-one,
16) 1-(4,5-dimethyl-1H-benzo[d]imidazol-1-yl)-3-((2R,3S)-3-hydroxypiperidin-2-yl)propan-2-one,
17) 1-(5-fluoro-4-(trifluoromethyl)-1H-benzo[d]imidazol-1-yl)-3-((2R,3S)-3-hydroxypiperidin-2-yl)propan-2-one,
18) 1-(5-bromo-4-(trifluoromethyl)-1H-benzo[d]imidazol-1-yl)-3-((2R,3S)-3-hydroxypiperidin-2-yl)propan-2-one,
19) 1-(4-bromo-5-methyl-1H-benzo[d]imidazol-1-yl)-3-((2R,3S)-3-hydroxypiperidin-2-yl)propan-2-one,
20) 1-(5-bromo-4-fluoro-1H-benzo[d]imidazol-1-yl)-3-((2R,3S)-3-hydroxypiperidin-2-yl)propan-2-one,
21) 1-(4-chloro-5-fluoro-1H-benzo[d]imidazol-1-yl)-3-((2R,3S)-3-hydroxypiperidin-2-yl)propan-2-one,
22) 1-(5-bromo-4-chloro-1H-benzo[d]imidazol-1-yl)-3-((2R,3S)-3-hydroxypiperidin-2-yl)propan-2-one,
23) 1-(6-bromo-4-methyl-1H-benzo[d]imidazol-1-yl)-3-((2R,3S)-3-hydroxypiperidin-2-yl)propan-2-one,
24) 1-(6-chloro-4-methyl-1H-benzo[d]imidazol-1-yl)-3-((2R,3S)-3-hydroxypiperidin-2-yl)propan-2-one,
25) 1-(5,6-dichloro-1H-benzo[d]imidazol-1-yl)-3-((2R,3S)-3-hydroxypiperidin-2-yl)propan-2-one,
26) 1-(6-bromo-5-fluoro-1H-benzo[d]imidazol-1-yl)-3-((2R,3S)-3-hydroxypiperidin-2-yl)propan-2-one,
27) 1-(5,6-dibromo-1H-benzo[d]imidazol-1-yl)-3-((2R,3S)-3-hydroxypiperidin-2-yl)propan-2-one,
28) 1-(6-chloro-7-methyl-1H-benzo[d]imidazol-1-yl)-3-((2R,3S)-3-hydroxypiperidin-2-yl)propan-2-one,
29) 1-(5-bromo-1H-imidazo[4,5-b]pyridin-1-yl)-3-((2R,3S)-3-hydroxypiperidin-2-yl)propan-2-one,
30) 1-((2R,3S)-3-hydroxypiperidin-2-yl)-3-(5-(trifluoromethyl)-1H-imidazo[4,5-b]pyridin-1-yl)propan-2-one,
31) 1-(6-bromo-1H-imidazo[4,5-b]pyridin-1-yl)-3-((2R,3S)-3-hydroxypiperidin-2-yl)propan-2-one,
32) 1-(6-chloro-1H-imidazo[4,5-c]pyridin-1-yl)-3-((2R,3S)-3-hydroxypiperidin-2-yl)propan-2-one,
33) 1-(7-bromo-1H-imidazo[4,5-c]pyridin-1-yl)-3-((2R,3S)-3-hydroxypiperidin-2-yl)propan-2-one,
34) 1-((2R,3S)-3-hydroxypiperidin-2-yl)-3-(3H-imidazo[4,5-b]pyridin-3-yl)propan-2-one,
35) 1-(5-bromo-3H-imidazo[4,5-b]pyridin-3-yl)-3-((2R,3S)-3-hydroxypiperidin-2-yl)propan-2-one,
36) 1-((2R,3S)-3-hydroxypiperidin-2-yl)-3-(5-(trifluoromethyl)-3H-imidazo[4,5-b]pyridin-3-yl)propan-2-one,
37) 1-(6-bromo-3H-imidazo[4,5-b]pyridin-3-yl)-3-((2R,3S)-3-hydroxypiperidin-2-yl)propan-2-one,
38) 3-(3-((2R,3S)-3-hydroxypiperidin-2-yl)-2-oxopropyl)-3H-imidazo[4,5-b]pyridine-6-carbonitrile,
39) 1-(6-chloro-7-methyl-3H-imidazo[4,5-b]pyridin-3-yl)-3-((2R,3S)-3-hydroxypiperidin-2-yl)propan-2-one,
40) 1-(6-bromo-7-methyl-3H-imidazo[4,5-b]pyridin-3-yl)-3-((2R,3S)-3-hydroxypiperidin-2-yl)propan-2-one, 41) 1-(5,7-dichloro-3H-imidazo[4,5-b]pyridin-3-yl)-3-((2R,3S)-3-hydroxypiperidin-2-yl)propan-2-one,
42) 1-(6-bromo-7-chloro-3H-imidazo[4,5-b]pyridin-3-yl)-3-((2R,3S)-3-hydroxypiperidin-2-yl)propan-2-one,
43) 3-(3-((2R,3S)-3-hydroxypiperidin-2-yl)-2-oxopropyl)-3H-imidazo[4,5-c]pyridine-6-carboxylic acid hydrochloride salt,
44) 1-(6-chloro-9H-purin-9-yl)-3-((2R,3S)-3-hydroxypiperidin-2-yl)propan-2-one hydrochloride salt,
45) 1-((2R,3S)-3-hydroxypiperidin-2-yl)-3-(4,5,6,7-tetrahydro-1H-benzo[d]imidazol-1-yl)propan-2-one,
46) 1-(5,6-dichloro-2-methyl-1H-benzo[d]imidazol-1-yl)-3-((2R,3S)-3-hydroxypiperidin-2-yl)propan-2-one,
47) 1-(4,5-difluoro-2-methyl-1H-benzo[d]imidazol-1-yl)-3-((2R,3S)-3-hydroxypiperidin-2-yl)propan-2-one,
48) 1-(5,6-dichloro-2-ethyl-1H-benzo[d]imidazol-1-yl)-3-((2R,3S)-3-hydroxypiperidin-2-yl)propan-2-one,
49) 1-((2R,3S)-3-hydroxypiperidin-2-yl)-3-(2-methyl-1H-imidazo[4,5-b]pyridin-1-yl)propan-2-one,
50) 1-(5,6-dichloro-2-(trifluoromethyl)-1H-benzo[d]imidazol-1-yl)-3-((2R,3S)-3-hydroxypiperidin-2-yl)propan-2-one,
51) 1-(5,6-dichloro-2-((dimethylamino)methyl)-1H-benzo[d]imidazol-1-yl)-3-((2R,3S)-3-hydroxypiperidin-2-yl)propan-2-one,
52) 1-(2-(aminomethyl)-5,6-dichloro-1H-benzo[d]imidazol-1-yl)-3-((2R,3S)-3-hydroxypiperidin-2-yl)propan-2-one,
53) 1-(6-fluoro-2-(2-hydroxyethyl)-1H-benzo[d]imidazol-1-yl)-3-((2R,3S)-3-hydroxypiperidin-2-yl)propan-2-one,
54) 1-(2-((R)-1-hydroxyethyl)-1H-benzo[d]imidazol-1-yl)-3-((2R,3S)-3-hydroxypiperidin-2-yl)propan-2-one,
55) 1-(2-((S)-1-hydroxyethyl)-1H-benzo[d]imidazol-1-yl)-3-((2R,3S)-3-hydroxypiperidin-2-yl)propan-2-one,
56) 1-(2-(hydroxymethyl)-1H-benzo[d]imidazol-1-yl)-3-((2R,3S)-3-hydroxypiperidin-2-yl)propan-2-one,
57) 1-(5-bromo-2-(hydroxymethyl)-1H-benzo[d]imidazol-1-yl)-3-((2R,3S)-3-hydroxypiperidin-2-yl)propan-2-one,
58) 1-(6-bromo-2-(hydroxymethyl)-1H-benzo[d]imidazol-1-yl)-3-((2R,3S)-3-hydroxypiperidin-2-yl)propan-2-one,
59) 1-(2-(hydroxymethyl)-6-(trifluoromethyl)-1H-benzo[d]imidazol-1-yl)-3-((2R,3S)-3-hydroxypiperidin-2-yl)propan-2-one,
60) 1-(2-(hydroxymethyl)-5-(trifluoromethoxy)-1H-benzo[d]imidazol-1-yl)-3-((2R,3S)-3-hydroxypiperidin-2-yl)propan-2-one,
61) 1-(2-(hydroxymethyl)-7-(trifluoromethoxy)-1H-benzo[d]imidazol-1-yl)-3-((2R,3S)-3-hydroxypiperidin-2-yl)propan-2-one,
62) 1-(2-(hydroxymethyl)-4,5-dimethyl-1H-benzo[d]imidazol-1-yl)-3-((2R,3S)-3-hydroxypiperidin-2-yl)propan-2-one,
63) 1-(5,6-dichloro-2-(methoxymethyl)-1H-benzo[d]imidazol-1-yl)-3-((2R,3S)-3-hydroxypiperidin-2-yl)propan-2-one,
64) 1-(5,6-dichloro-1H-benzo[d]imidazol-1-yl)-3-((2R,3S)-3-hydroxypiperidin-2-yl)propan-2-one oxime,
65) 1-(5,6-dichloro-2-(hydroxymethyl)-1H-benzo[d]imidazol-1-yl)-3-((2R,3S)-3-hydroxypiperidin-2-yl)propan-2-one oxime,
66) 1-(6-bromo-1H-imidazo[4,5-b]pyridin-1-yl)-3-((2R,3S)-3-hydroxypiperidin-2-yl)propan-2-one oxime,
67) 1-(5,6-dichloro-1H-benzo[d]imidazol-1-yl)-3-((2R,3S)-3-hydroxypiperidin-2-yl)propan-2-one O-methyl oxime,
68) 1-(2-(hydroxymethyl)-1H-imidazo[4,5-b]pyridin-1-yl)-3-((2R,3S)-3-hydroxypiperidin-2-yl)propan-2-one,
69) (2R,3S)-2-(3-(1H-benzo[d]imidazol-1-yl)-2-hydroxypropyl)piperidin-3-ol,
70) (2R,3S)-2-(3-(5,6-dichloro-1H-benzo[d]imidazol-1-yl)-2-hydroxypropyl)piperidin-3-ol,
71) (2R,3S)-2-(3-(5-bromo-4-chloro-1H-benzo[d]imidazol-1-yl)-2-hydroxypropyl)piperidin-3-ol,
72) (2R,3S)-2-(3-(5-bromo-4-(trifluoromethyl)-1H-benzo[d]imidazol-1-yl)-2-hydroxypropyl)piperidin-3-ol,
73) (2R,3S)-2-(3-(4-bromo-5-methyl-1H-benzo[d]imidazol-1-yl)-2-hydroxypropyl)piperidin-3-ol,
74) (2R,3S)-2-(3-(5-bromo-4-fluoro-1H-benzo[d]imidazol-1-yl)-2-hydroxypropyl)piperidin-3-ol,
75) (2R,3S)-2-(3-(4,5-dichloro-1H-benzo[d]imidazol-1-yl)-2-hydroxypropyl)piperidin-3-ol,
76) (2R,3S)-2-(3-(5-chloro-4-methyl-1H-benzo[d]imidazol-1-yl)-2-hydroxypropyl)piperidin-3-ol,
77) (2R,3S)-2-(3-(6-chloro-7-methyl-3H-imidazo[4,5-b]pyridin-3-yl)-2-hydroxypropyl)piperidin-3-ol,
78) (2R,3S)-2-(3-(6-bromo-7-methyl-3H-imidazo[4,5-b]pyridin-3-yl)-2-hydroxypropyl)piperidin-3-ol,
79) (2R,3S)-2-(3-(6-bromo-7-chloro-3H-imidazo[4,5-b]pyridin-3-yl)-2-hydroxypropyl)piperidin-3-ol,
80) (2R,3S)-2-(3-(1H-benzo[d]imidazol-1-yl)-2-hydroxy-2-methylpropyl)piperidin-3-ol,
81) (2R,3S)-2-(3-(5,6-dichloro-1H-benzo[d]imidazol-1-yl)-2-fluoropropyl)piperidin-3-ol,
82) (2R,3S)-2-(3-(5,6-dichloro-1H-benzo[d]imidazol-1-yl)-2,2-difluoropropyl)piperidin-3-ol,
83) (2R,3S)-2-(3-(5,6-dichloro-1H-benzo[d]imidazol-1-yl)-2-methoxypropyl)piperidin-3-ol,
84) (2R,3S)-2-(3-(5,6-dichloro-1H-benzo[d]imidazol-1-yl)-2-hydroxy-2-methylpropyl)piperidin-3-ol,
85) (2R,3S)-2-(2-((5-bromo-4-methyl-1H-benzo[d]imidazol-1-yl)methyl)-3,3,3-trifluoro-2-hydroxypropyl)piperidin-3-ol,
86) (2R,3S)-2-(3-(5,6-dichloro-1H-benzo[d]imidazol-1-yl)-2-(methylamino)propyl)piperidin-3-ol,
87) 1-(5,6-dichloro-2-(hydroxymethyl)-1H-benzo[d]imidazol-1-yl)-3-((2R,3S)-3-hydroxypiperidin-2-yl)propan-2-one,
88) (2R,3S)-2-(3-(5,6-dichloro-2-(hydroxymethyl)-1H-benzo[d]imidazol-1-yl)-2-hydroxypropyl)piperidin-3-ol,
89) (2R,3S)-2-(3-(5-bromo-4-methyl-1H-benzo[d]imidazol-1-yl)-2-hydroxypropyl)piperidin-3-ol,
90) (S)-1-(5,6-dichloro-1H-benzo[d]imidazol-1-yl)-3-(pyrrolidin-2-yl)propan-2-one,
91) 1-(5-chloro-1H-pyrrolo[2,3-b]pyridin-1-yl)-3-((2R,3S)-3-hydroxypiperidin-2-yl)propan-2-one,
92) 1-(6-bromo-1H-pyrrolo[2,3-b]pyridin-1-yl)-3-((2R,3S)-3-hydroxypiperidin-2-yl)propan-2-one,
93) 1-(7-chloro-1H-pyrrolo[2,3-c]pyridin-1-yl)-3-((2R,3S)-3-hydroxypiperidin-2-yl)propan-2-one,
94) 1-(6-bromo-1H-pyrrolo[3,2-b]pyridin-1-yl)-3-((2R,3S)-3-hydroxypiperidin-2-yl)propan-2-one,
95) 1-(3-((2R,3S)-3-hydroxypiperidin-2-yl)-2-oxopropyl)-4-methyl-1H-pyrrolo[2,3-b]pyridine-5-carbonitrile,
96) 1-(5-chloro-1H-indazol-1-yl)-3-((2R,3S)-3-hydroxypiperidin-2-yl)propan-2-one,
97) 1-(4-bromo-5-methyl-1H-indazol-1-yl)-3-((2R,3S)-3-hydroxypiperidin-2-yl)propan-2-one, 98) 1-(5-chloro-1H-pyrazolo[3,4-b]pyridin-1-yl)-3-((2R, 3S)-3-hydroxypiperidin-2-yl)propan-2-one,
99) 1-(5-chloro-1H-benzo[d][1,2,3]triazol-1-yl)-3-((2R, 3S)-3-hydroxypiperidin-2-yl)propan-2-one, and
100) 1-(6-chloro-1H-benzo[d][1,2,3]triazol-1-yl)-3-((2R, 3S)-3-hydroxypiperidin-2-yl)propan-2-one.

13. A method for preparing a compound represented by the following Chemical Formula 1 comprising the steps of:
   1) reacting a compound represented by the following Chemical Formula 1-1 with a compound represented by the following Chemical Formula 1-2 to prepare a compound represented by the following Chemical Formula 1-3; and
   2) subjecting a compound represented by the following Chemical Formula 1-3 to a deprotection reaction to prepare a compound represented by the following Chemical Formula 1:

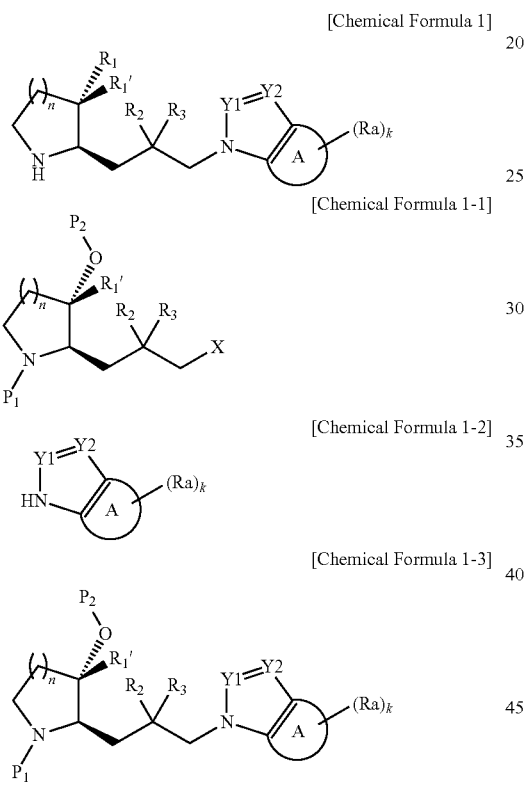

[Chemical Formula 1]

[Chemical Formula 1-1]

[Chemical Formula 1-2]

[Chemical Formula 1-3]

In Chemical Formulae 1, 1-1, 1-2 and 1-3,
n, $R_1$, $R_1'$, $R_2$, $R_3$, Y1, Y2, A, k and Ra are as defined in claim 1,
X is halogen,
$P_1$ is any one protecting group selected from the group consisting of carbobenzyloxy, para-methoxybenzyl carbonyl, tert-butyloxycarbonyl, 9-fluorenyl methyloxy carbonyl, acetyl, benzoyl, benzyl and para-methoxybenzyl,
$P_2$ is any one protecting group selected from the group consisting of acetyl, benzoyl, benzyl, beta-methoxyethoxy methyl ether, methoxymethyl ether, para-methoxybenzyl ether, methylthiomethyl ether, pivaloyl, tetrahydropyranyl, trityl, tert-butyldimethylsilyl, triisopropylsilyl ether, and ethoxyethyl ether,
provided that when $R_1$ is hydrogen, hydrogen is substituted instead of O—$P_2$ in Chemical Formulae 1-1 and 1-3.

14. A pharmaceutical composition for the inhibition of PRS enzyme activity, comprising a compound of claim 1, or a pharmaceutically acceptable salt thereof, and a carrier.

15. A compound represented by Chemical Formula 2-9 or a compound represented by Chemical Formula 2-13:

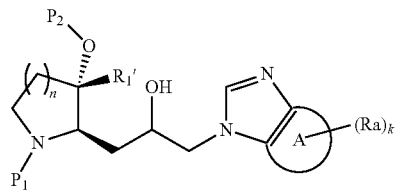

[Chemical Formula 2-9]

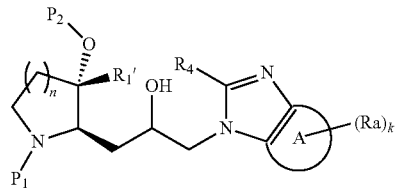

[Chemical Formula 2-13]

in Chemical Formulae 2-9 and 2-13,
$P_1$ and $P_2$ are each independently a protecting group,
n is 1 or 2,
$R_1'$ is hydrogen,
$R_4$ is $C_{1-4}$ alkyl, $C_{1-4}$ hydroxyalkyl, $C_{1-4}$ alkyl substituted with $C_{1-4}$ alkoxy, $C_{1-4}$ haloalkyl, or —$(CH_2)_m NR_9 R_{10}$, wherein m is an integer of 1 to 4, $R_9$ and $R_{10}$ are each independently hydrogen or $C_{1-4}$ alkyl,
A is benzene, heteroaryl having 1 to 4 nitrogen atoms, or cyclohexene, as a six-membered ring,
k is an integer of 0 to 4,
each of Ra is independently $C_{1-4}$ alkyl, $C_{1-4}$ alkoxy, $C_{1-4}$ haloalkyl, $C_{1-4}$ haloalkoxy, halogen, cyano, or carboxy.

16. A method for preparing a compound represented by the following Chemical Formula 2-9 according to claim 15 comprising the steps of:
   1) reacting a compound represented by the following Chemical Formula 2-5 with a compound represented by the following Chemical Formula 2-6 in the presence of a base to prepare a compound represented by the following Chemical Formula 2-7;
   2) reacting the compound represented by Chemical Formula 2-7 in the presence of hydrogen and metal to prepare a compound represented by the following Chemical Formula 2-8; and
   3) reacting a compound represented by the following Chemical Formula 2-8 i) in the presence of trimethyl orthoformate or triethyl orthoformate, and para toluenesulfonic acid or pyridinium para toluenesulfonate, or ii) in the presence of formic acid, to prepare a compound represented by the following Chemical Formula 2-9:

[Chemical Formula 2-5]

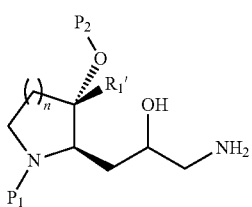

[Chemical Formula 2-6]

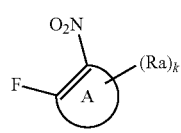

[Chemical Formula 2-7]

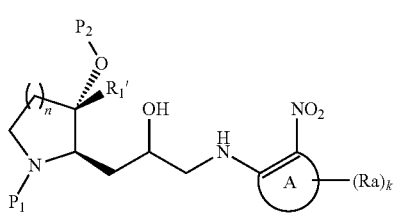

[Chemical Formula 2-8]

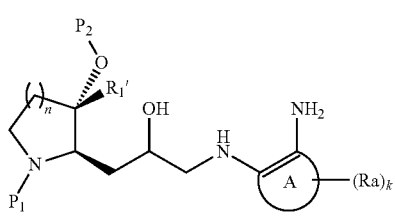

[Chemical Formula 2-9]

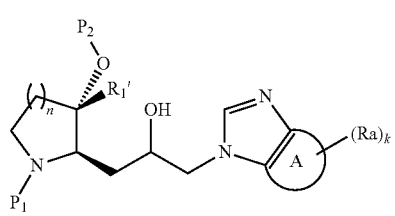

in Chemical Formulae 2-5 to 2-9,
P$_1$, P$_2$, n, R$_1$', A, k and Ra are as defined in claim 15.

17. A method for preparing a compound represented by the following Chemical Formula 2-13 according to claim 15 comprising the steps of:

1) reacting a compound represented by the following Chemical Formula 2-5 with a compound represented by the following Chemical Formula 2-6 in the presence of a base to prepare a compound represented by the following Chemical Formula 2-7;

2) reacting the compound represented by the following Chemical Formula 2-7 in the presence of hydrogen and metal to prepare a compound represented by the following Chemical Formula 2-8;

3) reacting the compound represented by Chemical Formula 2-8 and R$_4$-substituted carboxylic acid (R$_4$—COOH) in the presence of an amide coupling reagent of bis-(2-oxo-3-oxazolydinyl)phosphoryl hydrochloride, 1-ethyl-(3-(3-dimethylamino)propyl)-carbodiimide hydrochloride, benzotriazol-1-yloxy-tris-(pyrrolidino) phosphonium hexafluorophosphate, benzotriazole-ol, (benzotriazol-1-yloxy) tris(dimethylamino)phosphonium hexafluorophosphate or O-(benzotriazol-1-yl)-N,N,N,N'-tetramethyluronium hexafluorophosphate, and a base of triethylamine, diisopropyl ethylamine, pyridine, dimethylaniline, dimethylaminopyridine or sodium hydroxide to prepare a compound represented by Chemical Formula 2-12; and:

[Chemical Formula 2-5]

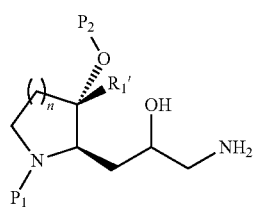

[Chemical Formula 2-6]

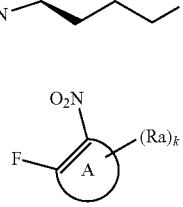

[Chemical Formula 2-7]

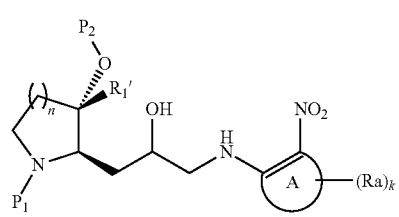

[Chemical Formula 2-8]

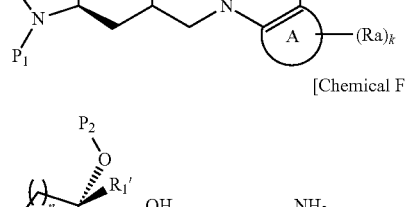

[Chemical Formula 2-12]

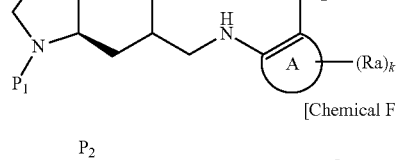

[Chemical Formula 2-13]

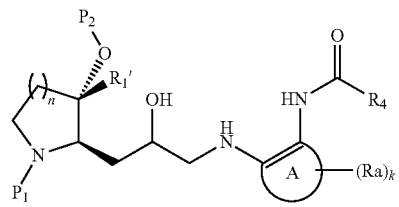

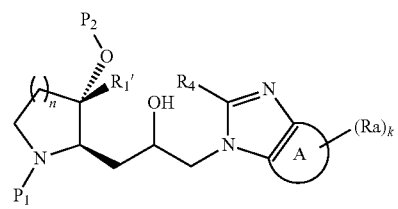

In Chemical Formulae 2-5 to 2-8, 2-12 and 2-13,
P$_1$, P$_2$, n, R$_1$', R$_4$, A, k and Ra are as defined in claim 15.

* * * * *